(12) United States Patent
Fensome et al.

(10) Patent No.: US 6,583,145 B1
(45) Date of Patent: Jun. 24, 2003

(54) THIO-OXINDOLE DERIVATIVES

(75) Inventors: Andrew Fensome, Wayne, PA (US); Puwen Zhang, Audubon, PA (US); Marci C. Koko, Bethlehem, PA (US); Lin Zhi, San Diego, CA (US); Todd K. Jones, Solana Beach, CA (US); Jay E. Wrobel, Lawrenceville, NJ (US); Christopher M. Tegley, Thousand Oaks, CA (US); James P. Edwards, San Diego, CA (US); Edward G. Melenski, Woodlyn, PA (US)

(73) Assignees: Wyeth, Madison, NJ (US); Ligand Pharmaceuticals, San Diego, CA (US)

( * ) Notice: Subject to any disclaimer, the term of this patent is extended or adjusted under 35 U.S.C. 154(b) by 0 days.

(21) Appl. No.: 10/253,380

(22) Filed: Sep. 24, 2002

Related U.S. Application Data

(62) Division of application No. 10/022,467, filed on Oct. 30, 2001, now Pat. No. 6,521,657, which is a division of application No. 09/552,033, filed on Apr. 19, 2000, now Pat. No. 6,355,648.
(60) Provisional application No. 60/172,259, filed on May 4, 1999, now abandoned.

(51) Int. Cl.[7] ................... A61K 31/404; A61K 31/506; C07D 209/40; C07D 403/10
(52) U.S. Cl. ....................... 514/256; 548/483; 514/415; 544/333
(58) Field of Search ................ 514/256, 415; 544/333; 548/483

(56) References Cited

U.S. PATENT DOCUMENTS

| | | |
|---|---|---|
| 3,635,964 A | 1/1972 | Skorcz |
| 3,917,592 A | 11/1975 | Kobzina |
| 4,093,730 A | 6/1978 | Butti |
| 4,440,785 A | 4/1984 | Walsh |
| 4,617,302 A | 10/1986 | Robertson |
| 4,666,913 A | 5/1987 | Kuhla |
| 4,670,566 A | 6/1987 | Walsh |
| 4,721,721 A | 1/1988 | Kuhla |
| 4,822,794 A | 4/1989 | Spada |
| 4,831,027 A | 5/1989 | Narr |
| 4,853,473 A | 8/1989 | Fischer |
| 4,933,336 A | 6/1990 | Martin |
| 5,007,952 A | 4/1991 | Kume |
| 5,171,851 A | 12/1992 | Kim |
| 5,414,088 A | 5/1995 | Von Der Saal |
| 5,447,928 A | 9/1995 | Williams |
| 5,453,516 A | 9/1995 | Fischer |
| 5,475,020 A | 12/1995 | Johnson |
| 5,521,166 A | 5/1996 | Grubb |
| 5,552,412 A | 9/1996 | Cameron |
| 5,659,046 A | 8/1997 | Kameswaran |
| 5,681,817 A | 10/1997 | Hodgen |
| 5,688,808 A | 11/1997 | Jones |
| 5,688,810 A | 11/1997 | Jones |
| 5,693,646 A | 12/1997 | Jones |
| 5,693,647 A | 12/1997 | Jones |
| 5,696,127 A | 12/1997 | Jones |
| 5,696,130 A | 12/1997 | Jones |
| 5,696,133 A | 12/1997 | Jones |
| 5,719,136 A | 2/1998 | Chwalisz |
| 5,733,902 A | 3/1998 | Schneider |
| 5,808,139 A | 9/1998 | Pathirana |
| 5,874,430 A | 2/1999 | Christ |
| 6,077,840 A | 6/2000 | Kurihara |
| 6,153,622 A | 11/2000 | Cameron |
| 6,204,286 B1 | 3/2001 | Cameron |
| 6,306,851 B1 | 10/2001 | Santilli |
| 6,319,912 B1 | 11/2001 | Grubb |
| 6,329,416 B1 | 12/2001 | Grubb |
| 6,339,098 B1 | 1/2002 | Collins |
| 6,355,648 B1 | 3/2002 | Fensome |
| 6,358,947 B1 | 3/2002 | Zhi et al. |
| 6,358,948 B1 | 3/2002 | Zhang |
| 6,369,056 B1 | 4/2002 | Zhang et al. |
| 6,380,178 B1 | 4/2002 | Grubb |
| 6,380,235 B1 | 4/2002 | Zhang |
| 6,391,907 B1 | 5/2002 | Fensome |
| 6,399,593 B1 | 6/2002 | Grubb |

(List continued on next page.)

FOREIGN PATENT DOCUMENTS

DE 3633861 4/1988

(List continued on next page.)

OTHER PUBLICATIONS

R. Evans, "The Steroid and Thyroid Hormone Receptor Superfamily", Science, 240:889 (May 13, 1988).

(List continued on next page.)

Primary Examiner—Joseph K. McKane
Assistant Examiner—Sonya Wright
(74) Attorney, Agent, or Firm—Howson and Howson

(57) ABSTRACT

This invention relates to compounds which are agonists of the progesterone receptor which have the general structure:

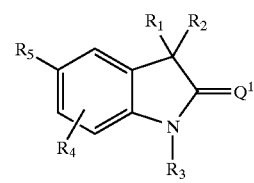

wherein:

$R_1$, $R_2$, $R_3$, $R_4$, $R_5$ and $Q^1$ are as defined herein, or a pharmaceutically acceptable salt thereof, as well as methods of using these compounds to induce contraception or treat progesterone-related carcinomas and adenocarcinomas.

11 Claims, No Drawings

U.S. PATENT DOCUMENTS

| | | |
|---|---|---|
| 6,407,101 B1 | 6/2002 | Collins |
| 6,417,214 B1 | 7/2002 | Ullrich |
| 6,423,699 B1 | 7/2002 | Grubb |
| 6,436,929 B1 | 8/2002 | Zhang . |
| 6,441,019 B2 | 8/2002 | Santilli |
| 6,441,193 B1 | 8/2002 | Cameron |
| 6,444,668 B1 | 9/2002 | Grubb |
| 6,462,032 B1 | 10/2002 | Grubb |
| 2001/0025051 A1 | 9/2001 | Cameron |

FOREIGN PATENT DOCUMENTS

| | | |
|---|---|---|
| DE | 4330234 | 3/1995 |
| DE | 4344463 | 6/1995 |
| EP | 022317 | 1/1981 |
| EP | 208510 | 1/1987 |
| EP | 311135 | 4/1989 |
| EP | 385850 | 9/1990 |
| EP | 483077 | 9/1991 |
| EP | 454330 | 10/1991 |
| EP | 535529 | 9/1992 |
| EP | 510235 | 10/1992 |
| EP | 947507 | 10/1999 |
| EP | 978279 | 2/2000 |
| JP | 63112584 | 5/1988 |
| WO | WO86/03749 A1 | 7/1986 |
| WO | WO91/04974 A1 | 4/1991 |
| WO | WO91/06545 A1 | 5/1991 |
| WO | WO93/12085 A1 | 6/1993 |
| WO | WO94/14434 A1 | 7/1994 |
| WO | WO94/29272 A1 | 12/1994 |
| WO | WO95/11013 A1 | 4/1995 |
| WO | WO95/20389 A1 | 8/1995 |
| WO | WO95/20972 A1 | 8/1995 |
| WO | WO95/33746 A1 | 12/1995 |
| WO | WO96/15794 A1 | 5/1996 |
| WO | WO96/19458 A1 | 6/1996 |
| WO | WO96/19997 A1 | 7/1996 |
| WO | WO97/13767 A1 | 4/1997 |
| WO | WO97/49407 A1 | 12/1997 |
| WO | WO98/14436 A1 | 4/1998 |
| WO | WO98/27059 A1 | 6/1998 |
| WO | WO98/55116 A1 | 12/1998 |
| WO | WO99/10325 A1 | 3/1999 |
| WO | WO99/11264 A1 | 3/1999 |
| WO | WO99/15500 A1 | 4/1999 |
| WO | WO99/44608 A1 | 9/1999 |

OTHER PUBLICATIONS

A. Ulmann et al., "Clinical Uses of Mifepristone (MFP)," Ann. N.Y. Acad. Sci., 261:248 (Jun. 12, 1995).

R. Kekkonen et al., "Sequential Regiment of the Antiprogesterone RU486 and Synthetic Progestin for Contraception", Fertility and Sterility, 60(4):610 (Oct., 1993).

K. Horwitz et al., "Progestin, Progesterone Receptors, and Breast Cancer", Horm. Cancer, publisher: Birkhaeuser, Boston, Mass., ed. Vedeckis, pp. 283–306 (1996) (abstract only).

A. Murphy et al, "Regression of Uterine Leiomyomata in Response to the Antiprogesterone RU486", J. Clin. Endo. Metab., 76(2):513 (Feb., 1993).

L. Kettel et al, "Endocrine Responses to Long–Term Administration of the Antiprogesterone RU486 in Patients with Pelvic Endometriosis", Fertility and Sterility, 56(3):402 (Sep., 1991).

H. Michna et al, "Differentiation Therapy with Progesterone Antagonists", Ann. N.Y. Acad. Sci., 761:224 (Jun., 1995).

L. Zhi et al, "5–Ary–1,2–Dihydrochromeno[3,4–f] quinolines: A Novel Class of Nonsteroidal Human Progesterone Receptor Agonists", J. Med. Chem., 41(3):291 (Oct. 22, 1998).

D. Combs et al, "Nonsteroidal Progesterone Receptor Ligands. 2. High–Affinity Ligands with Selectivity for Bone Cell Progesterone Receptors", J. Med. Chem., 38:4880 (Dec. 8, 1995).

K. Perlman et al, "20–Oxopregnacalciferols: Vitamin D Compounds that Bind the Progesterone Receptor", Tet. Letters, 35(15)2295 (1994).

L. Hamann et al, "Synthesis and Biological Activity of Novel Nonsteroidal Progesterone Receptor Antagonists", Ann. N.Y. Acad. Sci., 761:383 (Jun. 12, 1995).

R. Chen et al, "Synthesis and SAR of a Novel Series of Spirobenzothlzaepine Derivatives with Antiprogestin Activity", POI–37, $16^{th}$ Int. Cong. Het. Chem., Montana (1997).

B. Narr et al, "Preparation, Testing, and Formulation of Imidazobenzoxazinones as Cardiotonics", Chemical Abstracts, 109:22973 (1988).

R. Hartmann et al, "Effect of Brofoxine, A New Anxiolytic on Experimentally Induced Conflict in Rats", Proc. West. Pharmacol. Soc., 21:51–55 (1978).

B. Singh et al, "Novel cAMP PDE III Inhibitor Imidazo[4, 5–b]pyridin–2(3H)–ones and Thiazolo[4,5–b]pyridin–2(3H)–ones and their Analogs", J. Med. Chem., 37:248 (Jan. 21, 1994).

A. Andreani et al., "Potential Antitumor Agents XVII (1). Cytotoxic Agents from Indole Derivatives and their Intermediates", Acta. Pharm. Nord., 2(6):407 (1990).

Sakata et al, "Silver Halide Photographic Materials Useful for Platemaking", Chemical Abstracts, 123:301431 (1993).

P. Pflegel et al, "Polarografie con 7–Chlor–5–phenyl–2–thioxo–1H–2,3–dihydro–1,3,4–benzotriazepinen", Pharmazie, 37(10):714–717 (1982).

E. Barengolts et al, "Progesterone Antagonist RU486 has Bone–Sparing Effects in Ovariectomized Rats", Bone, 17(1):21 (Jul., 1995).

E. Gromachevskaya et al, "Studies of 4H–3, 1–Benzoxazines", Chem. Heterocycl. Cmpds, 33(10):1209–1214 (1997).

D. Chiarino et al, "2,1–Benzisothiazoline 2,2–Dioxide and Derivatives", J. Heterocycl. Chem., 23(6):1645–1649 (Nov.– Dec., 1986).

A. Turck et al, "On the Metabolism of 3–Substituted and 3,6–Disubstituted Pyridazines", Tetrahedron, 49(3):599–606 (1993).

V. Kumar et al, "Synthesis of 7–Azaindole and 7–Azaoxindole Derivatives through a Palladium–Catalyzed Cross–Coupling Reaction", J. Org. Chem., 57(25):6995–6998 (1992).

P. Canonne et al, "Spirocyclization of 1–(o–Aminophenyl-)cycloalkanols and 1–(2'–Amino–3'–pyridinyl)cycloalkanols", J Heterocyclic Chem., 26:113 (Jan.–Feb., 1989).

M–C. Forest et al, "A Novel Class of Cardiotonic Agents: Synthesis and Biological Evaluation of 5–Substituted 3,6–Dihydrothiadiazin–2–ones with Cyclic AMP Phosphodiesterase Inhibiting and Myofibrillar Calcium Sensitizing Properties", J. Med. Chem., 35:163–172 (Jan., 1992).

D. Combs et al, "Heteroatom Analogues of Bemoradan: Chemistry and Cardiotonic Activity of 1,4–Benzothiazinylpyridazinones", J. Med. Chem., 35:172–176 (Jan., 1992).

Kurihari et al., "Synthesis of ±-PF1092A, B, and C; New Nonsteroidal Progesterone Receptor Ligands", J. Antibiotics, 50(4):360 (Apr., 1997).

A. Kende et al., "Regioselective C–3 Alkylation of Oxindole Dianion", Synth. Commun. 12(1):1 (1982).

T. Tucker et al., "Synthesis of a Series of 4–(Arylethylnyl)–6–Chloro–4–Cyclopropyl–3, 4–dihydroquinazolin–2(1H)–ones as Novel Non–Nucleoside HIV–1 Reverse Transcriptase Inhibitors", J. Med. Chem., 37:2347–2444 (Jul. 22, 1994).

J. Edwards et al, "5–Aryl–1,2–Dihydro–5H–Chromeno[3, 4–f]Quinolines as Potent, Orally Active, Nonsteroidal Progesterone Receptor Agonists: The Effect of D–Ring Substituents", J. Med. Chem., 41:303–310 (Jan. 29, 1998).

Derwent WPI abstract, "New Imidazo–Pyridine Derivatives—Useful as Platelet Agglutination Inhibitor, Antiallergic, Antiinflammatory Sedative, Cardiac, and Cardiovascular Vasodilators", JP 63112584. (1988).

Derwent WPI abstract, N. Brumagniez et al., "Benzimidazole and Azabenzimidazole(s)—Having Cardiotonic, Vasodilating, Anti–Hypertensive, Anti–Aggregation, and Anti–Ulcer Activity", EP 385850. (1990).

Derwent WPI abstract, F. Arndt et al., "New Heterocycle substituted Benzo–Fused Azine and Azole Derivatives—Useful as Selective Herbicides for Pre or Post–Emergence Application", EP 311135. (1989).

K. Horwitz et al., "Progestin, Progesterone Receptors and Breast Cancer", "Hormones and Cancer", publisher: Birkhaeuser, Boston, Mass., ed. Vedeckis, p. 283–306 (1996).

V. Mamaev et al; "Synthesis of 4H–Thieno [3,2–B] Pyrrol–5(6H)–One" Bulletin of the Academy of Sciences of the USSR. Division of Chemical Science, US, Consultants Bureau. New York. vol. 9, p. 1549–1553, (1966).

Derwent WPI Abstract, K. Chwalisz et al. "Female Contraceptive Method Comprises Gestation Treatment with Intermittent Progesterone Antagonist Administration", DE 4,330, 234. (1995).

Derwent WPI Abstracts, K. Chwalisz et al. "Contraceptive Pack for Implantation Inhibitor—Contains Competitive Progesterone Antagonist and Gestagen for Sequential Oral Administration", DE 4,344, 463.

K. Kolasa et al., "Preliminary Pharmacological Studies of the Central Action of Phenyl and Piperidinomethyl Derivatives of 2–Benzoxazolone", Chemical Abstracts, vol. 99, No. 1, Abst. No. 157a (Jul. 4, 1983).

N. Meanwell et al., "Regiospecific Functionalization of 1,3–dihydro–2H–Benzimidazol–2–One and Structurally Related Cyclic Urea Derivatives", J. Organic Chem., 60(6):1565–82 (Mar. 24, 1995).

B. Singh et al., "An Efficient and Novel Synthesis of Fused Thiazol–2(3H)–ones" Heterocycles, 36(1):133–134, p. 136, compounds 16a, 18a (Jan. 1993).

G. Vernin et al., "Etude Dans la Serie des Radicaux Heterocycliques. Partie XV. Decomposition aprotique de 1' amino–6–ethyl–2–benzothiazole dans des substrats aromatiques et heteroaromatiques: preparation des mesityl–6–et furyl–6–ethyl–2–benzothiazoles, des sels quaternaires et des spiropyrannes correspondants", Helvetica Chimica Acta, 62(1/3):21–30 (Jan. 24, 1979).

A. Fensome et al, "Thio–Oxindole Derivatives", U.S. Patent Publication No. US–2002–0103248–A1, published Aug. 1, 2002 (division of (BBA) cited above).

P. Zhang et al, "Cyclocarbamate Derivatives as Progesterone Receptor Modulators", U.S. Patent Publication No. US–2002–0049204–A1, published Apr. 25, 2002.

A. Fensome et al, "Indoline Derivatives", U.S. Patent Publication No. US–2002–0086874–A1, published Jul. 4, 2002 (division of (BBE) cited above).

P. Zhang et al, "Quinazolinone and Benzoxazine Derivatives as Progesterone Receptor Modulators", U.S. Patent Publication No. US–2002–0094983–A1, published Jul. 18, 2002 (division of (BBB) cited above).

P. Zhang et al, "Cyclic Urea and Cyclic Amide Derivatives", U.S. Patent Publication No. US–2002–0111355–A1, published Aug. 15, 2002 (division of (BBD) cited above).

M. Collins et al, "Cyanopyrroles", U.S. Patent Publication No. US–2002–0068735–A1, published Jun. 6, 2002 (division of (BBI) cited above).

G. Grubb et al, "Combination Regimens Using 3,3–Substituted Indoline Derivatives", U.S. Patent Publication No. US–2002–0025099–A1, published Mar. 21, 2002 (division of (BI) cited above).

P. Zhang et al, "Benzimidazolones and Analogues", U.S. Patent Publication No. US–2002–0115853–A1, published Aug. 22, 2002 (division of (BBF) cited above).

G. Grubb et al, "Contraceptive Methods Using Benzimadazolones", U.S. Patent Publication No. US–2002–0151531–A1, published Oct. 17, 2002 (division of (CC) cited above).

A. Fensome et al, "Thio–Oxindole Derivatives", U.S. Patent Publication No. US–2002–0169198–A1, published Nov. 14, 2002 (continuation of (CW) cited above).

W–Y. Leung et al, Lipophilic Sulfophenylcarbocyanine Dyes: Synthesis of a New Class of Fluorescent Cell Membrane Probes, Bioorganic & Medicinal Chemistry Letters, 6(13):1479–1482 (1996), STN International ®CAPLUS Database, Accession No. 1996:466516 (Abstract only).

I. Koveman et al, "Condensed Heterocyclic Ring Structure Compounds Used Organic Luminophores, etc.", Russian Federation Patent No. 2100359, published Dec. 27, 1997 (Abstract only).

THIO-OXINDOLE DERIVATIVES

CROSS-REFERENCE TO RELATED APPLICATIONS

This application is a divisional of U.S. patent application Ser. No. 10/022,467 now U.S. Pat. No. 6,521,657, filed Oct. 30, 2001, which is a divisional of U.S. patent application Ser. No. 09/552,033, filed Apr. 19, 2000, now U.S. Pat. No. 6,355,648, which claims the benefit of the priority of U.S. Provisional Patent Application No. 60/172,259, filed May 4, 1999, now abandoned.

BACKGROUND OF THE INVENTION

This invention relates to compounds which are agonists of the progesterone receptor, their preparation and utility.

Intracellular receptors (IR) form a class of structurally related gene regulators known as "ligand dependent transcription factors" (R. M. Evans, Science, 240, 889, 1988). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control formulations, typically in the presence of an ER agonist, alternatively they may be used in conjunction with a PR antagonist. ER agonists are used to treat the symptoms of menopause, but have been associated with a proliferative effect on the uterus which can lead to an increased risk of uterine cancers. Co-administration of a PR agonist reduces/ablates that risk.

Jones, et al, described in U.S. Pat. No. 5,688,810 the PR antagonist dihydroquinoline A.

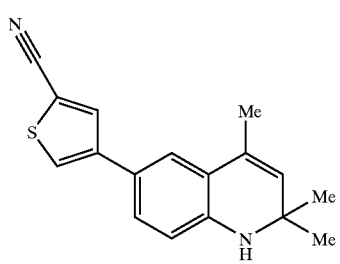

A

Jones, et al, described the enol ether B (U.S. Pat. No. 5,693,646) as a PR ligand.

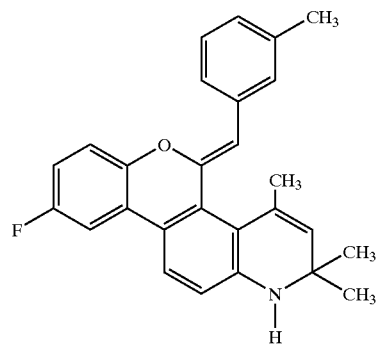

B

Jones, et al, described compound C (U.S. Pat. No. 5,696,127) as a PR ligand.

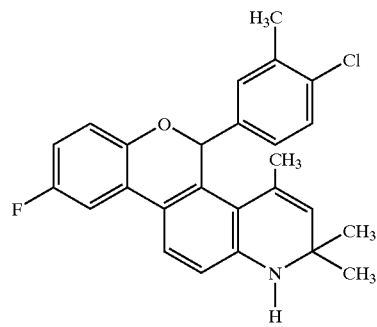

C

Zhi, et al, described lactones D, E and F as PR antagonists (J. Med. Chem., 41, 291, 1998).

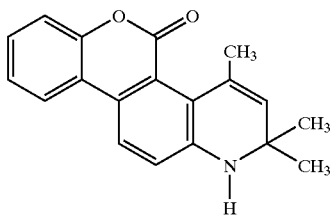

D

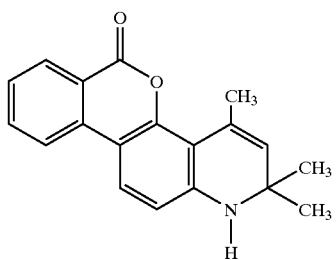

E

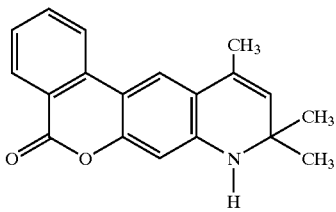

F

Zhi, et al, described the ether G as a PR antagonist (J. Med. Chem., 41, 291, 1998).

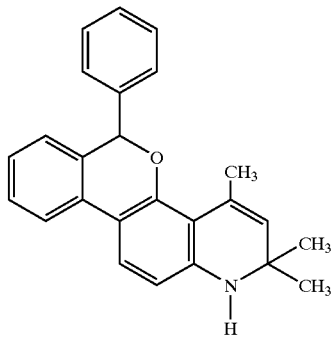

G

Combs, et al., disclosed the amide H as a ligand for the PR (J. Med. Chem., 38, 4880, 1995).

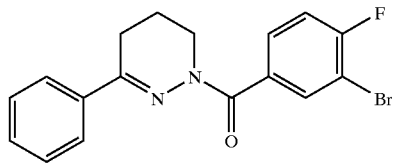

H

Perlman, et. al., described the vitamin D analog I as a PR ligand (Tet. Letters, 35, 2295, 1994).

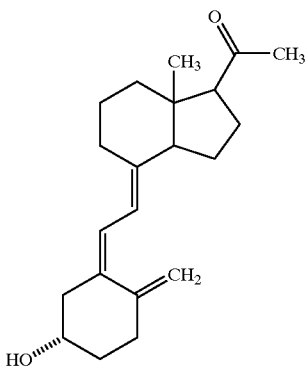

I

Hamann, et al, described the PR antagonist J (Ann. N.Y. Acad. Sci., 761, 383, 1995).

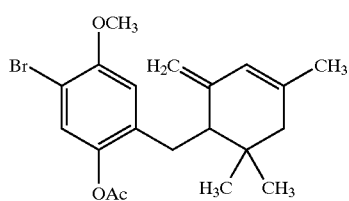

J

Chen, et al, described the PR antagonist K (Chen, et al, POI-37, 16$^{th}$ Int. Cong. Het. Chem., Montana, 1997).

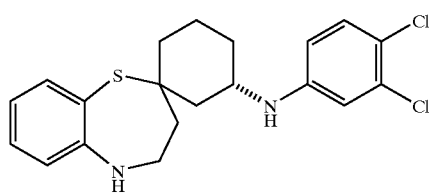

K

Kurihari, et. al., described the PR ligand L (J. Antibiotics, 50, 360, 1997).

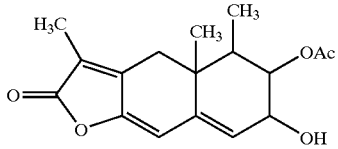

L

Kuhla, et al, taught the oxindole M as a cardiotonic (WO 86/03749).

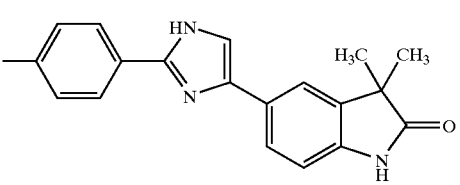

M

Weber, described the oxindole N for cardiovascular indications (WO 91/06545).

N

Fischer, et as, claim a preparation for making compounds which include the generic structure O (U.S. Pat. No. 5,453,516).

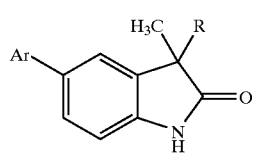

O

Singh, et al, described the PDE III inhibitor P (J. Med. Chem., 37, 248, 1994).

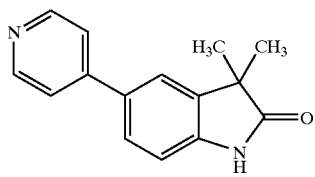

P

Andreani, et al, described the cytotoxic agent Q (*Acta. Pharn. Nord.*, 2, 407, 1990).

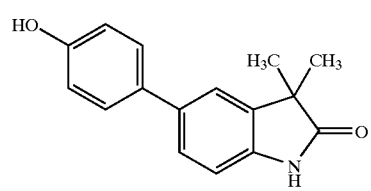

Q

Binder, et al, described structure R which is an intermediate for preparing COX II inhibitors (WO 97/13767).

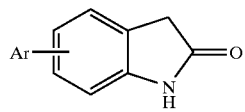

R

Walsh (A. H. Robins) described the oxindole S as an intermediate (U.S. Pat. No. 4,440,785, U.S. Pat. No. 4,670, 566).

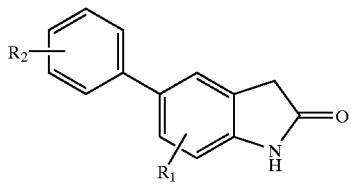

S $R_1$ = F, Cl, Br, alkyl, $NH_2$
$R_2$ = alkyl, alkoxy, F, Cl, $NH_2$, $CF_3$

Bohm, et al, claim the oxindole T as cardiovascular agents (WO 91/06545).

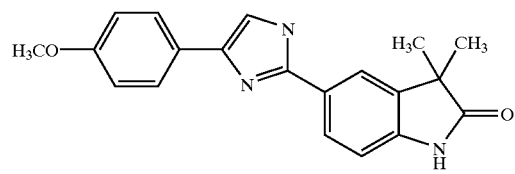

T

Bohm, et al, include the generic structure U (WO 91/04974).

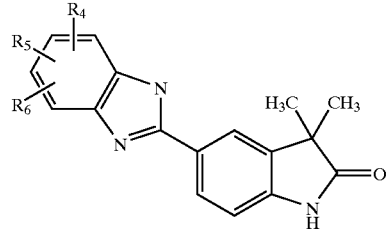

U

JP 63112584 A contains the generic structure V:

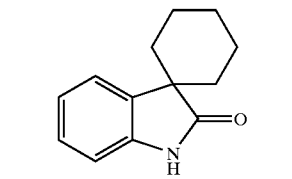

V

Boar, et al, described the dioxolane W as an intermediate for preparation of acetyl-cholinesterase inhibitors (WO 93/12085 A1).

W

Kende, et al, described methodology for preparing 3,3-substituted oxindoles, e.g. X, that was utilized in the present invention (*Synth. Commun.*, 12, 1, 1982).

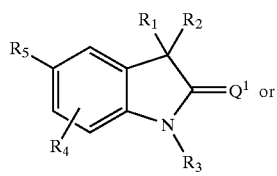

X

DESCRIPTION OF THE INVENTION

This invention provides compounds of the formulae 1 or 2:

1

-continued

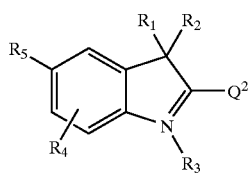
2 wherein:
R$_1$ and R$_2$ are chosen independently from the group of H, alkyl, substituted alkyl; OH; O(alkyl); O(substituted alkyl); OAc; aryl; optionally substituted aryl; heteroaryl; optionally substituted heteroaryl; alkylaryl; alkylheteroaryl; 1-propynyl; or 3-propynyl:
or R$_1$ and R$_2$ are joined to form a ring comprising one of the following: —CH$_2$(CH$_2$)$_n$CH$_2$—; —CH$_2$CH$_2$CMe$_2$CH$_2$CH$_2$—; —O(CH$_2$)$_m$CH$_2$—; O(CH$_2$)$_p$O—; —CH$_2$CH$_2$OCH$_2$CH$_2$—; or —CH$_2$CH$_2$N(H or alkyl)CH$_2$CH$_2$—;
m is an integer from 1 to 4;
n is an integer from 1 to 5;
p is an integer from 1 to 4;
or R$_1$ and R$_2$ together comprise a double bond to one of the following: CMe$_2$; C(cycloalkyl), O, C(cyloether).
R$_3$ is selected from H, OH, NH$_2$, C$_1$ to C$_6$ alkyl, substituted C$_1$ to C$_6$ alkyl, C$_3$ to C$_6$ alkenyl, alkynyl or substituted alkynyl, or COR$^A$;
R$^A$ is selected from H, Cl to C$_3$ alkyl, substituted C$_1$ to C$_3$ alkyl, C$_1$ to C$_3$ alkoxy, substituted C$_1$ to C$_3$ alkoxy, C$_1$ to C$_3$ aminoalkyl, or substituted C$_1$ to C$_3$ aminoalkyl;
R$_4$ is selected from H, halogen, CN, NH$_2$, C$_1$ to C$_6$ alkyl, substituted C$_1$ to C$_6$ alkyl, C$_1$ to C$_6$ alkoxy, substituted C$_1$ to C$_6$ alkoxy, C$_1$ to C$_6$ aminoalkyl, or substituted C$_1$ to C$_6$ aminoalkyl;
R$_5$ is selected from the groups a), b) or c):
  a) R$_5$ is a trisubstituted benzene ring containing the substituents X, Y and Z as shown below:

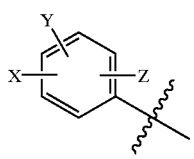

X is selected from halogen, OH, CN, C$_1$ to C$_3$ alkyl, substituted C$_1$ to C$_3$ alkyl, C$_1$ to C$_3$ alkoxy, substituted C$_1$ to C$_3$ alkoxy, C$_1$ to C$_3$ thioalkyl, substituted C$_1$ to C$_3$ thioalkyl, S(O)alkyl, S(O)$_2$alkyl, C$_1$ to C$_3$ aminoalkyl, substituted C$_1$ to C$_3$ aminoalkyl, NO$_2$, C$_1$ to C$_3$ perfluoroalkyl, 5 or 6 membered heterocyclic ring containing 1 to 3 heteroatoms, CONH$_2$, CSNH$_2$, CONHalkyl, CSNHalkyl, CON(alkyl)$_2$, CSN(alkyl)$_2$, COR$^B$, OCOR$^B$, NR$^C$COR$^B$;
  R$^B$ is selected from H, C$_1$ to C$_3$ alkyl, substituted C$_1$ to C$_3$ alkyl, aryl, substituted aryl, C$_1$ to C$_3$ alkoxy, substituted C$_1$ to C$_3$ alkoxy, C$_1$ to C$_3$ aminoalkyl, or substituted C$_1$ to C$_3$ aminoalkyl;
  R$^C$ is H, C$_1$ to C$_3$ alkyl, or substituted C$_1$ to C$_3$ alkyl;
Y and Z are independently selected from H, halogen, CN, NO$_2$, C$_1$ to C$_3$ alkoxy, C$_1$ to C$_3$ alkyl, or C$_1$ to C$_3$ thioalkyl; or b) R$_5$ is a five or six membered heterocyclic ring with 1, 2, or 3 heteroatoms selected from O, S, SO, SO$_2$ or NR$^6$ and containing one or two independent substituents from the group of H, halogen, CN, NO$_2$ and C$_1$ to C$_3$ alkyl, C$_1$ to C$_3$ alkoxy, C$_1$ to C$_3$ aminoalkyl, COR$^D$, or NR$^E$COR$^D$;
    R$^D$ is H, C$_1$ to C$_3$ alkyl, substituted C$_1$ to C$_3$ alkyl, aryl, substituted aryl, C$_1$ to C$_3$ alkoxy, substituted C$_1$ to C$_3$ alkoxy, C$_1$ to C$_3$ aminoalkyl, or substituted C$_1$ to C$_3$ aminoalkyl;
    R$^E$ is H, C$_1$ to C$_3$ alkyl, or substituted C$_1$ to C$_3$ alkyl;
    R$^6$ is H, or C$_1$ to C$_3$ alkyl; or
  c) R$_5$ is an indol-4-yl, indol-7-yl or benzo-2-thiophene moiety, the moiety being optionally substituted by from 1 to 3 substituents selected from halogen, lower alkyl, CN, NO$_2$, lower alkoxy, or CF$_3$;
Q$^1$ is S, NR$_7$, CR$_8$R$_9$;
R$_7$ is selected from the group including CN, C$_1$ to C$_6$ alkyl, substituted C$_1$ to C$_6$ alkyl, C$_3$ to C$_8$ cycloalkyl, substituted C$_3$ to C$_8$ cycloalkyl, aryl, substituted aryl, heterocyclic, substituted heterocyclic, acyl, substituted acyl, aroyl, substituted aroyl, SO$_2$CF$_3$, OR$^{11}$ or NR$^{11}$R$^{12}$;
R$_8$ and R$_9$ are independent substituents selected from the group of H, C$_1$ to C$_6$ alkyl, substituted C$_1$ to C$_6$ alkyl, C$_3$ to C$_8$ cycloalkyl, substituted C$_3$ to C$_8$ cycloalkyl, aryl, substituted aryl, heterocyclic, substituted heterocyclic, NO$_2$, CN, or CO$_2$R$_{10}$,
R$_{10}$ is C$_1$ to C$_3$ alkyl; or
CR$_8$R$_9$ comprises a six membered ring as shown by the structure below

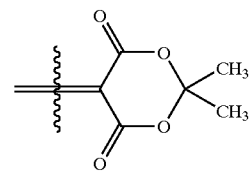

Q$^2$ is selected from the moieties:

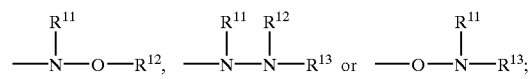

R$^{11}$, R$^{12}$ and R$^{13}$ are independently selected from H, C$_1$ to C$_6$ alkyl, substituted C$_1$ to C$_6$ alkyl, aryl, substituted aryl, heteroaryl, substituted heteroaryl, acyl, substituted acyl, aroyl or substituted aroyl or sulfonyl;

or a pharmaceutically acceptable salt thereof

A preferred list of substituents represented by R$^{11}$, R$^{12}$ and R$^{13}$ in groups of the compounds described herein are H, C$_1$ to C$_6$ alkyl, substituted C$_1$ to C$_6$ alkyl, —C(O)—(C$_1$ to C$_6$ alkyl), —S(O)$_2$—(C$_1$ to C$_6$ alkyl), phenyl or benzyl.

It will be understood that this invention includes all tautomeric forms of the compounds, chemical formulae and substituents described herein.

Two preferred sets of compounds of this invention is depicted by structures 2 and 3, respectively:

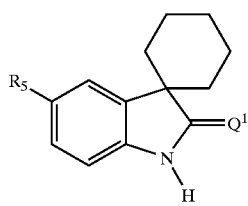

2

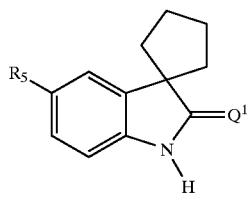

3 each wherein $R_5$ is a disubstituted benzene ring containing the substituents X and Y as shown below

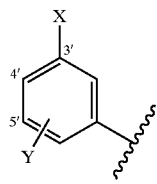

X is selected from halogen, CN, $CONH_2$, $CSNH_2$, CONHalkyl, CSNHalkyl, $CONalkyl_2$, $CSNalkyl_2$ $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, or $C_1$ to $C_3$ thioalkoxy;

Y is a substituent on the 4' or 5'position from the group including H, halogen, CN, $NO_2$, $C_1$ to $C_3$ alkoxy, $C_1$ to $C_4$ alkyl, or $C_1$ to $C_3$ thioalkyl;

or a pharmaceutically acceptable salt thereof.

Another preferred group of formula 2 are those wherein $R_5$ is a five membered ring with the structure shown below

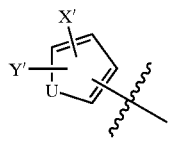

wherein:

U is O, S, or $NR_6$;

$R_6$ is H, or $C_1$ to $C_3$ alkyl, or $C_1$ to $C_4$ $CO_2$alkyl;

X' is selected from halogen, CN, $NO_2$, $CONH_2$, $CSNH_2$, CONHalkyl, CSNHalkyl, $CONalkyl_2$, $CSNalkyl_2$, $C_1$ to $C_3$ alkyl, or $C_1$ to $C_3$ alkoxy;

Y' is from the group of H, F or $C_1$ to $C_4$ alkyl;

or a pharmaceutically acceptable salt thereof

A further preferred subgroup of the compounds above are those in which $R_5$ is a thiophene or furan ring substituted by X' and Y', as described above.

A further preferred subgroup group of compounds of formulas 2 and 3 are those wherein $R_5$ is a six membered ring with the structure:

wherein $X^1$ is N or $CX^2$, $X^2$ is halogen, CN, $CONH_2$, $CSNH_2$, CONHalkyl, CSNHalkyl, $CONalky_2$, $CSNalkyl_2$ or $NO_2$;

$Q^1$ is S, $NR_7$, $CR_8R_9$;

$R_7$ is from the group including CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;

$R_8$ and $R_9$ are independent substituents from the group including H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN $CO_2R_{10}$, $R_{10}$ is $C_1$ to $C_3$ alkyl;

$CR_8R_9$ are within a six membered ring as shown by the structure below

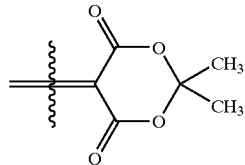

or pharmaceutically acceptable salt thereof.

Still another preferred group of these compounds includes those having the general formulae:

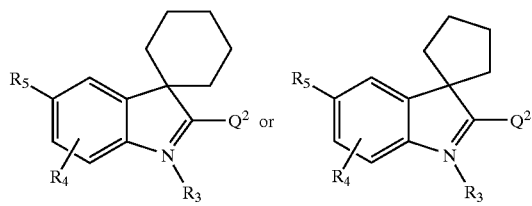

each wherein $R_5$ is a disubstituted benzene ring containing the substituents X and Y as shown below

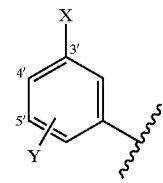

X is selected from halogen, CN, $CONH_2$, $CSNH_2$, CONHalkyl, CSNHalkyl, $CONalkyl_2$, $CSNalkyl_2$, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, or $C_1$ to $C_3$ thioalkoxy;

Y is a substituent on the 4' or 5'position from the group including H, halogen, CN, $NO_2$, $C_1$ to $C_3$ alkoxy, $C_1$ to $C_4$ alkyl, or $C_1$ to $C_3$ thioalkyl;

or a pharmaceutically acceptable salt thereof.

A further preferred subgroup group of compounds of formulae:

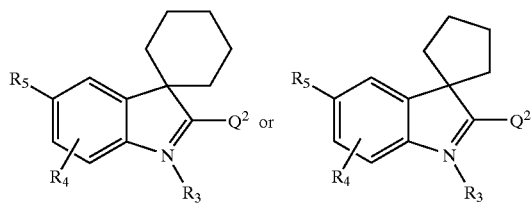

are those wherein $R_5$ is a six membered ring with the structure:

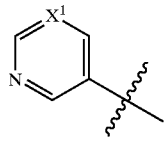

wherein $X^1$ is N or $CX^2$, $X^2$ is halogen, CN, $CONH_2$, $CSNH_2$, CONHalkyl, CSNHalkyl, $CONalkyl_2$, $CSNalkyl_2$ or $NO_2$;

$Q^2$ is as defined above;

$R_7$ is from the group including CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;

$R_8$ and $R_9$ are independent substituents from the group including H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN $CO_2R_{10}$, $R_{10}$ is $C_1$ to $C_3$ alkyl;

$CR_8R_9$ are within a six membered ring as shown by the structure below

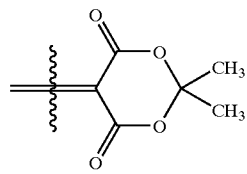

or pharmaceutically acceptable salt thereof.

A further preferred set of compounds of this invention is depicted by structure 4,

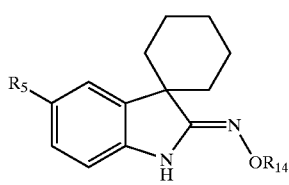

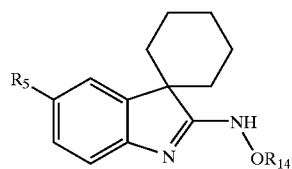

Wherein $R_{14}$ is chosen from the group H, acyl, substituted acyl, aroyl, substituted aroyl, sulfonyl, substituted sulfonyl.

Wherein $R_5$ is a disubstituted benzene ring containing the substituents X and Y as shown below

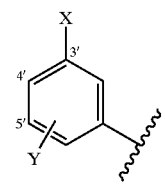

X is selected from halogen, CN, $CONH_2$, $CSNH_2$, CONHalkyl, CSNHalkyl, $CON(alkyl)_2$, $CSN(alkyl)_2$. CNHNHOH, $CNH_2NOH$, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, or $C_1$ to $C_3$ thioalkoxy;

Y is a substituent on the 4' or 5'position from the group including H, halogen, CN, $NO_2$, $C_1$ to $C_3$ alkoxy, $C_1$ to $C_4$ alkyl, or $C_1$ to $C_3$ thioalkyl;

or a pharmaceutically acceptable salt thereof.

Another preferred group of formula 4 are those wherein $R_5$ is a five membered ring with the structure shown below

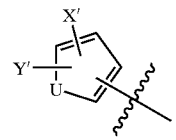

wherein:

U is O, S, or $NR_6$;

$R_6$ is H, or $C_1$ to $C_3$ alkyl, or $C_1$ to $C_4$ $CO_2$alkyl;

X' is selected from halogen, CN, $NO_2$, $CONH_2$, CNHNHOH, $CNH_2NOH$, $CSNH_2$, CONHalkyl, CSNHalkyl, $CONalkyl_2$, $CSNalkyl_2$, $C_1$ to $C_3$ alkyl, or $C_1$ to $C_3$ alkoxy;

Y' is from the group of H, F or $C_1$ to $C_4$ alkyl;

or a pharmaceutically acceptable salt thereof.

A further preferred subgroup of the compounds above are those in which $R_5$ is a thiophene or furan ring substituted by X' and Y', as described above.

A further preferred subgroup group of compounds of formula 4 are those wherein $R_5$ is a six membered ring with the structure:

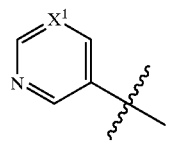

wherein

X¹ is N or CX²,

X² is halogen, CN, $CONH_2$, $CSNH_2$, CONHalkyl, CSNHalkyl, $CONalkyl_2$, $CSNalkyl_2$ or $NO_2$;

$R_7$ is from the group including CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;

$R_8$ and $R_9$ are independent substituents from the group including H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN $CO_2R_{10}$, $R_{10}$ is $C_1$ to $C_3$ alkyl;

or pharmaceutically acceptable salt thereof.

A further preferred set of compounds of this invention is depicted by structure 5,

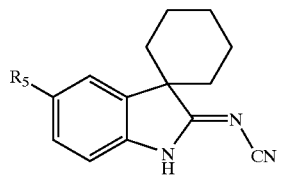

Wherein $R_5$ is a disubstituted benzene ring containing the substituents X and Y as shown below

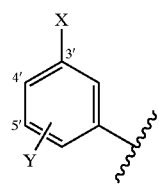

X is selected from halogen, CN, $CONH_2$, $CSNH_2$, CONHalkyl, CSNHalkyl, $CONalkyl_2$, $CSNalkyl_2$, CNHNOH, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, or $C_1$ to $C_3$ thioalkoxy;

Y is a substituent on the 4' or 5'position from the group including H, halogen, CN, $NO_2$, $C_1$ to $C_3$ alkoxy, $C_1$ to $C_4$ alkyl, or $C_1$ to $C_3$ thioalkyl;

or a pharmaceutically acceptable salt thereof.

Another preferred group of formula 5 are those wherein $R_5$ is a five membered ring with the structure shown below

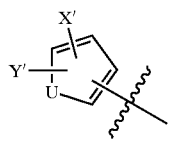

wherein:

U is O, S, or $NR_6$;

$R_6$ is H, or $C_1$ to $C_3$ alkyl, or $C_1$ to $C_4$ $CO_2$alkyl;

X' is selected from halogen, CN, $NO_2$, $CONH_2$, $CSNH_2$, CONHalkyl, CSNHalkyl, $CONalkyl_2$, $CSNalkyl_2$, $C_1$ to $C_3$ alkyl, or $C_1$ to $C_3$ alkoxy;

Y' is from the group of H, F or $C_1$ to $C_4$ alkyl;

or a pharmaceutically acceptable salt thereof.

A further preferred subgroup of the compounds above are those in which $R_5$ is a thiophene or furan ring substituted by X' and Y', as described above.

A further preferred subgroup group of compounds of formula 5 are those wherein $R_5$ is a six membered ring with the structure:

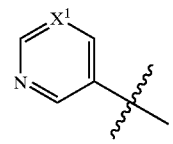

wherein

X¹ is N or CX²,

X² is halogen, CN, $CONH_2$, $CSNH_2$, CONHalkyl, CSNHalkyl, $CONalkyl_2$, $CSNalkyl_2$ or $NO_2$;

$R_7$ is from the group including CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;

$R_8$ and $R_9$ are independent substituents from the group including H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN $CO_2R_{10}$, $R_{10}$ is $C_1$ to $C_3$ alkyl;

or pharmaceutically acceptable salt thereof.

A further preferred set of compounds of this invention is depicted by structure 6,

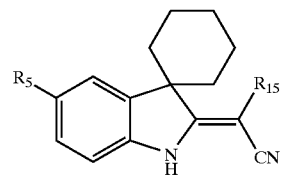

Wherein $R_{15}$ is selected from the group H, Me, $CO_2R$, acyl, substituted acyl, aroyl, substituted aroyl, alkyl, substituted alkyl, CN.

Wherein $R_5$ is a disubstituted benzene ring containing the substituents X and Y as shown below

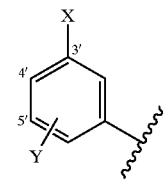

X is selected from halogen, CN, $CONH_2$, $CSNH_2$, CONHalkyl, CSNHalkyl, $CONalkyl_2$, $CSNalkyl_2$, CNHNOH, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, or $C_1$ to $C_3$ thioalkoxy;

Y is a substituent on the 4' or 5'position from the group including H, halogen, CN, $NO_2$, $C_1$ to $C_3$ alkoxy, $C_1$ to $C_4$ alkyl, or $C_1$ to $C_3$ thioalkyl;

or a pharmaceutically acceptable salt thereof.

Another preferred group of formula 6 are those wherein $R_5$ is a five membered ring with the structure shown below

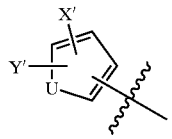

wherein:

U is O, S, or $NR_6$;

$R_6$ is H, or $C_1$ to $C_3$ alkyl, or $C_1$ to $C_4$ $CO_2$alkyl;

X' is selected from halogen, CN, $NO_2$, $CONH_2$, $CSNH_2$, CONHalkyl, CSNHalkyl, $CONalkyl_2$, $CSNalkyl_2$, $C_1$ to $C_3$ alkyl, or $C_1$ to $C_3$ alkoxy;

Y' is from the group of H, F or $C_1$ to $C_4$ alkyl;

or a pharmaceutically acceptable salt thereof.

A further preferred subgroup of the compounds above are those in which $R_5$ is a thiophene or furan ring substituted by X' and Y', as described above.

A further preferred subgroup group of compounds of formula 6 are those wherein $R_5$ is a six membered ring with the structure:

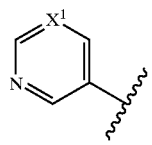

wherein $X^1$ is N or $CX^2$, $X^2$ is halogen, CN, $CONH_2$, $CSNH_2$, CONHalkyl, CSNHalkyl, $CONalkyl_2$, $CSNalkyl_2$ or $NO_2$;

$R_7$ is from the group including CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;

$R_8$ and $R_9$ are independent substituents from the group including H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN $CO_2R_{10}$, $R_{10}$ is $C_1$ to $C_3$ alkyl;

or pharmaceutically acceptable salt thereof.

A further preferred set of compounds of this invention is depicted by structure 7,

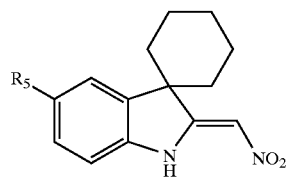

7

Wherein $R_5$ is a disubstituted benzene ring containing the substituents X and Y as shown below

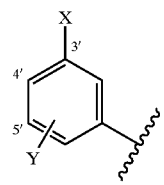

X is selected from halogen, CN, $CONH_2$, $CSNH_2$, CONHalkyl, CSNHalkyl, $CONalkyl_2$, $CSNalkyl_2$, CNHNOH, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, or $C_1$ to $C_3$ thioalkoxy;

Y is a substituent on the 4' or 5'position from the group including H, halogen, CN, $NO_2$, $C_1$ to $C_3$ alkoxy, $C_1$ to $C_4$ alkyl, or $C_1$ to $C_3$ thioalkyl;

or a pharmaceutically acceptable salt thereof.

Another preferred group of formula 7 are those wherein $R_5$ is a five membered ring with the structure shown below

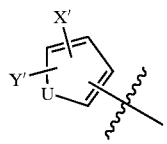

wherein:

U is O, S, or $NR_6$;

$R_6$ is H, or $C_1$ to $C_3$ alkyl, or $C_1$ to $C_4$ $CO_2$alkyl;

X' is selected from halogen, CN, $NO_2$, $CONH_2$, $CSNH_2$, CONHalkyl, CSNHalkyl, $CONalkyl_2$, $CSNalkyl_2$, $C_1$ to $C_3$ alkyl, or $C_1$ to $C_3$ alkoxy;

Y' is from the group of H, F or $C_1$ to $C_4$ alkyl;

or a pharmaceutically acceptable salt thereof.

A further preferred subgroup of the compounds above are those in which $R_5$ is a thiophene or furan ring substituted by X' and Y', as described above.

A further preferred subgroup group of compounds of formula 7 are those wherein $R_5$ is a six membered ring with the structure:

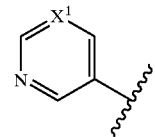

wherein $X^1$ is N or $CX^2$, $X^2$ is halogen, CN, $CONH_2$, $CSNH_2$, CONHalkyl, CSNHalkyl, $CONalkyl_2$, $CSNalkyl_2$ or $NO_2$;

$R_7$ is from the group including CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;

$R_8$ and $R_9$ are independent substituents from the group including H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN, or $CO_2R_{10}$, $R_{10}$ is $C_1$ to $C_3$ alkyl;

or pharmaceutically acceptable salt thereof.

The compounds of this invention may contain an asymmetric carbon atom and some of the compounds of this invention may contain one or more asymmetric centers and may thus give rise to optical isomers and diastereomers. While shown without respect to stereochemistry in Formula 1 and 2 the present invention includes such optical isomers and diastereomers; as well as the racemic and resolved, enantiomerically pure R and S stereoisomers; as well as other mixtures of the R and S stereoisomers and pharmaceutically acceptable salts thereof.

The term "alkyl" is used herein to refer to both straight- and branched-chain saturated aliphatic hydrocarbon groups having 1 to 8 carbon atoms, preferably 1 to 6 carbon atoms; "alkenyl" is intended to include both straight- and branched-chain alkyl group with 1 or 2 carbon-carbon double bonds and containing 2 to 8 carbon atoms, preferably 2 to 6 carbon atoms; "alkynyl" group is intended to cover both straight- and branched-chain alkyl group with at least 1 or 2 carbon-carbon triple bonds and containing 2 to 8 carbon atoms, preferably 2 to 6 carbon atoms.

The term "acyl" refers to a carbonyl substituent, including both straight- and branched-chain saturated aliphatic hydrocarbon groups having 1 to 8 carbon atoms, preferably 1 to 6 carbon atoms. The term "substituted acyl" refers to an acyl group as just described optionally substituted with from 1 to 6 groups chosen from the list halogen, CN, OH, and $NO_2$.

The term "aroyl" also refers to a carbonyl substituent carrying a phenyl group or a heteroaromatic group. The heteroaromatic groups of this include 2-, 3- or 4-pyridinyl, 2- and 3-furanyl, 2- or 3-thiophenyl, or 2- or 4-pyrimidinal. The term "substituted aroyl" also refers to an aroyl group as just described optionally substituted with from 1 to 6 groups chosen from the list halogen, CN, OH, and $NO_2$.

The terms "substituted alkyl", "substituted alkenyl", and "substituted alkynyl" refer to alkyl, alkenyl, and alkynyl as just described having one or more substituents from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamnino, arylthio. These substituents may be attached to any carbon of alkyl, alkenyl, or alkynyl group provided that the attachment constitutes a stable chemical moiety.

The term "aryl" is used herein to refer to an aromatic system which may be a single ring or multiple aromatic rings fused or linked together as such that at least one part of the fused or linked rings forms the conjugated aromatic system. The aryl groups include, but are not limited to, phenyl, naphthyl, biphenyl, anthryl, tetrahydronaphthyl, and phenanthryl.

The term "substituted aryl" refers to aryl as just defined having 1 to 4 substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, or arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicychic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe the heterocyclic group just defined having 1 to 4 substituents selected from the group which includes halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio.

The term "thioalkyl" is used herein to refer to the SR group, where R is alkyl or substituted alkyl, containing 1 to 8 carbon atoms, preferably 1 to 6 carbon atoms. The term "alkoxy" is used herein to refer to the OR group, where R is alkyl or substituted alkyl, containing 1 to 8 carbon atoms, preferably 1 to 6 carbon atoms. The term "aryloxy" is used herein to refer to the OR group, where R is aryl or substituted aryl, as defined above. The term "alkylcarbonyl" is used herein to refer to the RCO group, where R is alkyl or substituted alkyl, containing 1 to 8 carbon atoms, preferably 1 to 6 carbon atoms. The term "alkylcarboxy" is used herein to refer to the COOR group, where R is alkyl or substituted alkyl, containing 1 to 8 carbon atoms, preferably 1 to 6 carbon atoms. The term "aminoalkyl" refers to both secondary and tertiary amines wherein the alkyl or substituted alkyl groups, containing 1 to 8 carbon atoms, preferably 1 to 6 carbon atoms, which may be either the same or different and the point of attachment is on the nitrogen atom The term "halogen" refers to Cl, Br, F, or I.

The compounds of this invention may be prepared according to the methods described below.

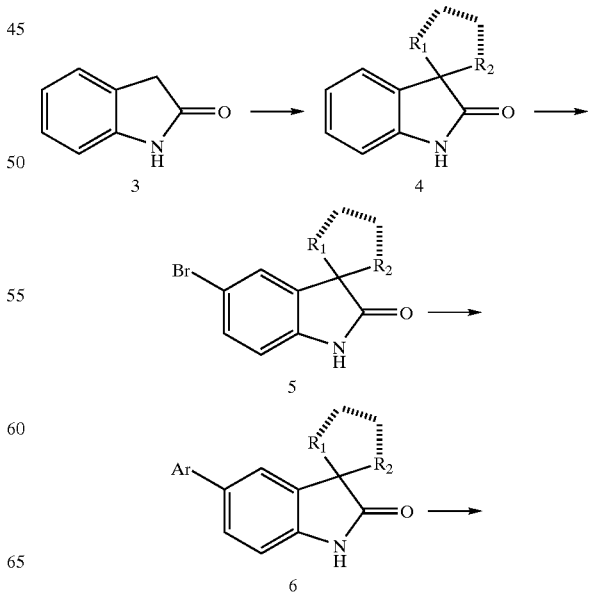

Scheme 1

-continued

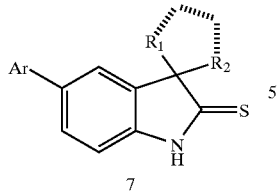

7

-continued

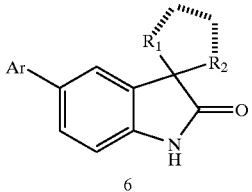

6

According to scheme 1, commercially available oxindole 3 is treated with a strong organo-metallic base (e.g. butyl lithium, lithium diisopropylamide, potassium hexamethyldisilazide) in an inert solvent (e.g. THF, diethyl ether) under nitrogen at reduced temperature (ca. −20° C.) (Kende, et al, Synth. Commun., 12, 1, 1982) in the presence of lithium chloride or N,N,N',N'-tetramethylethylenediamine. The resulting di-anion is then treated with excess electrophile such as an alkyl halide, preferably an iodide. If $R_1$ and $R_2$ are to be joined such as the product 4 contains a spirocycle at position 3, then the electrophile should be bifunctional, i.e. a diiodide. Subsequent bromination of 4 proceeds smoothly with bromine in acetic acid (an organic co-solvent such as dichloromethane may be added as required) in the presence of sodium acetate, to afford the aryl bromide 5. The bromide 5 is reacted with a palladium salt (e.g. tetrakis(triphenylphoshine)palladium(0) or palladium acetate), in a suitable solvent (e.g. THF, dimethoxyethane, acetone, ethanol or toluene) at room temperature under an inert atmosphere (argon, nitrogen). The mixture is then treated with an aryl or heteroaryl boronic acid or boronic acid ester and a base (sodium carbonate, triethylamine, potassium phosphate) in water or fluoride source (cesium fluoride) under anhydrous conditions. The required product 6 is then isolated and purified by standard means.

Reaction of the indoline-2-one derivative 6 with either Lawesson's reagent or phosphorous pentasulfide in a suitable organic solvent (pyridine, THF, dioxane, dimethoxyethane, dichloromethane, benzene, toluene, xylene) at a temperature between room temperature and the reflux temperature of the solvent provides access to the thiocarbonyl derivative 7. An additive such as sodium hydrogen carbonate may also be useful.

If $R_1$ and $R_2$ are different then the intermediate 4 is prepared by reacting the dianion of 3 with one equivalent of the electrophile $R_1$—X (X=leaving group e.g. iodine). The resultant mono-alkylated compound may then be isolated and re-subjected to the reaction conditions using $R_2$—X, or alternatively used in-situ for the second alkylation with $R_2$—X. Alternatively if the desired product 7 is to contain $R_2$=H, then the isolated mono-alkylated intermediate is taken though the subsequent steps.

Other methodologies are also available for coupling the pendant aryl or heteroaryl group, Ar, to the oxindole platform, for example reaction of compound 5 with an aryl or heteroaryl stannane, aryl or heteroaryl zinc, or aryl or heteroaryl magnesium halide in the presence of a palladium or nickel catalyst (scheme 2). The required aryl or heteroaryl-metallic species described above are formed through standard techniques.

Other functionalities can also be installed into the 3-position of the indoline platform according to scheme 3. Oxidation of the unsubstituted indoline 8, preferably under neutral or acidic conditions (e.g. selenium dioxide in dry dioxane at reflux) affords the isatin 9. Compound 9 may be further functionalized to provide a ketal 11 by treatment with an alcohol and acid catalyst under dehydrating conditions. Alternatively reaction of 9 with a second ketone under suitable conditions (piperidine in toluene at reflux; or $TiCl_4$/Zn in THF at reflux) affords alkylidene derivatives 11. Reaction of the isatin 9 with a grignard reagent or organo-lithium affords tertiary alcohols 12 (R=H). These alcohols may then be further functionalized by alkylation or acylation procedures.

Scheme 3

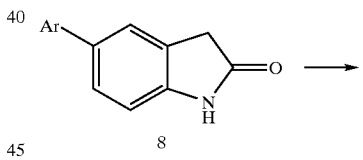

8

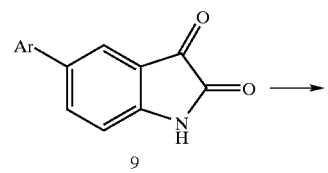

9

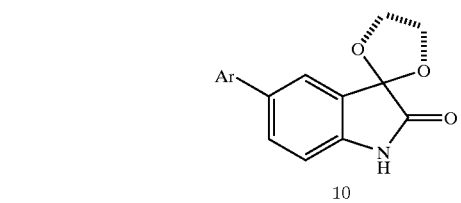

10

Scheme 2

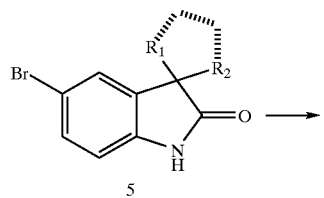

5

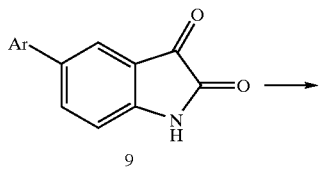

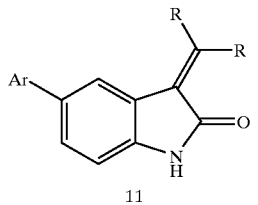

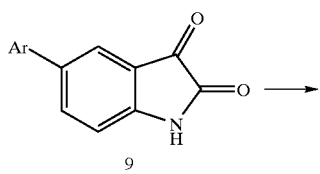

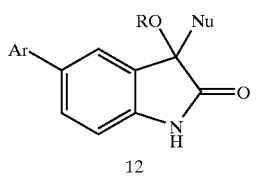

Reaction of the indoline-2-one derivative 6 with either Lawessen's reagent or phosphorous pentasulfide in a suitable organic solvent (pyridine, THF, dioxane, dimethoxyethane, dichloromethane, benzene, toluene, xylene) at a temperature between room temperature and the reflux temperature of the solvent provides access to the thiocarbonyl derivative 7. An additive such as sodium hydrogen carbonate may also be useful.

An alternative mode of preparation is to react compound 5 with either Lawessen's reagent or phosphorous pentasulfide in a suitable organic solvent (pyridine, THF, dioxane, dimethoxyethane, dichloromethane, benzene, toluene, xylene) at a temperature between room temperature and the reflux temperature of the solvent, under an inert atmosphere (nitrogen or argon) providing access to the thiocarbonyl derivative 13. Then reaction of bromide 13 in an anhydrous solvent (e.g. THF, Et$_2$O) with a strong base (sodium hydride preferred, sodium hexamethyldisilazide, potassium hydride) followed by reaction at reduced temperature (−50 to −20° C.) with n-butyllithium and N,N,N',N'-tetramethylethylenediamine followed after a suitable period of time by a trialkylborate (trimethyl or triisopropylborate) gives after acidic work-up the boronic acid 14 (scheme 4). Compound 14 may then be reacted under palladium catalyzed conditions (tetrakis(triphenylphosphine)palladium(0) or palladium acetate, base (NaHCO$_3$, Na$_2$CO$_3$, K$_2$CO$_3$, triethylamine, CsF) solvent (toluene/EtOH/water, THF/water, dimethoxyethane/water, anhydrous dimethoxyethane)) with an aryl or heteroaryl bromide, aryl or heteroaryl iodide, aryl or heteroaryl trifluoromethane sulfonate or aryl or heteroaryl fluorosulfonate, to provide the desired compounds 7.

Alternatively reaction of compound 13 under palladium catalyzed conditions (tetrakis(triphenylphosphine)palladium (0) or palladium acetate, base (NaHCO$_3$, Na$_2$CO$_3$, K$_2$CO$_3$, triethylamine, CsF) solvent (acetone/water, toluene/EtOH/water, THF/water, dimethoxyethane/water, anhydrous dimethoxyethane)) with an aryl or heteroaryl bromide, aryl or heteroaryl iodide, aryl or heteroaryl trifluoromethane sulfonate or aryl or heteroaryl fluorosulfonate, to provide the desired compounds 7.

Scheme 4

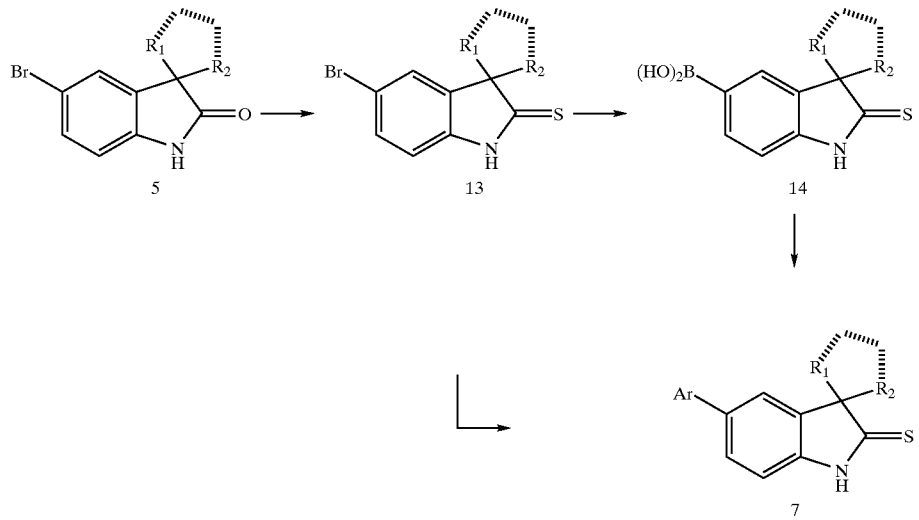

Scheme 5

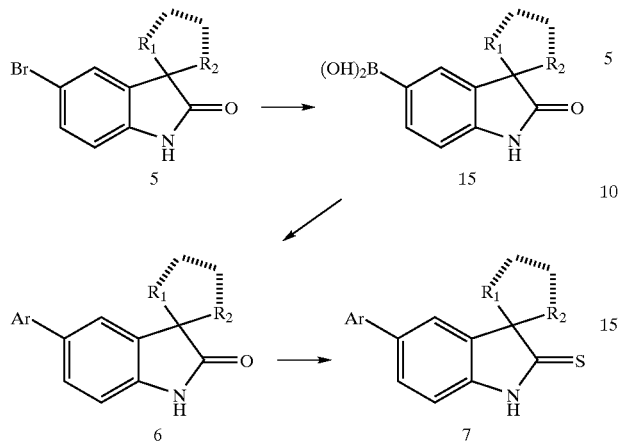

Scheme 6

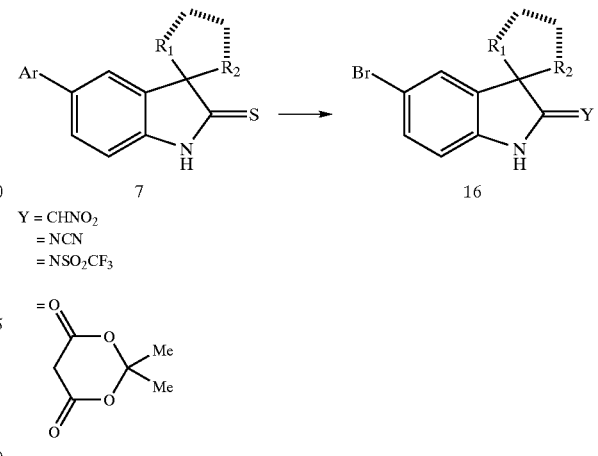

Y = CHNO₂
  = NCN
  = NSO₂CF₃

Treatment of the bromide 5 in an anhydrous solvent (e.g. THF, Et₂O) with a strong base (sodium hydride preferred, sodium hexamethyldisdazide, potassium hydride) followed by reaction at reduced temperature (−50 to −20° C.) with n-butyllithium and N,N,N',N'-tetramethylethylenediamine followed after a suitable period of time by a trialkylborate (trimethyl or triisopropylborate) gives after acidic work-up the boronic acid 15 (scheme 5). Compound 15 may then be reacted under palladium catalyzed conditions (tetrakis (triphenylphosphine)palladium(0), base (NaHCO₃, Na₂CO₃, K₂CO₃, triethylamine, CsF) solvent (toluene/ EtOH/water, THF/water, dimethoxyethane/water, anhydrous dimethoxyethane)) with an aryl or heteroaryl bromide, aryl or heteroaryl iodide, aryl or heteroaryl trifluoromethane sulfonate or aryl or heteroaryl fluorosulfonate, to provide the desired compounds 6.

An alternative strategy would be to prepare an organo zinc or magnesium reagent from compound 5 and react it in-situ with an aryl or heteroaryl bromide, aryl or heteroaryl iodide, aryl or heteroaryl trifluoromethane sulfonate of aryl or heteroaryl fluorosulfonate, under palladium catalyzed conditions to afford compound 6. Such an organo zinc or magnesium species could be prepared by treatment of the bromide 5 in an anhydrous solvent (e.g. THF, Et₂O) with a strong base (sodium hydride preferred, sodium hexamethyldisilazide, potassium hydride) followed by reaction at reduced temperature (−50 to −20° C.) with n-butyllithium and N,N,N',N'-tetramethylethylenediamine followed after a suitable period of time by reaction with anhydrous zinc chloride or magnesium bromide.

Reaction of the indoline-2-one derivative 6 with either Lawesson's reagent or phosphorous pentasulfide in a suitable organic solvent (pyridine, THF, dioxane, dimethoxyethane, dichloromethane, benzene, toluene, xylene) at a temperature between room temperature and the reflux temperature of the solvent, under an inert atmosphere (nitrogen or argon) provides access to the thiocarbonyl derivative 15. An additive such as sodium hydrogen carbonate may also be useful.

According to scheme 6 thioamide derivatives 7 may be converted into enamine derivatives 16 (Wrobel, et al, J. Med. Chem., 1989, 2493).

Thus reaction of thioamide 7 (Pg=H, 2-(trimethylsilyl)-ethoxymethyl, benzyl, etc) with triethyloxonium tetrafluoroborate followed by reaction with a nucleophile (nitromethane, cyanamide, trifluoromethanesulfonamide, Meldrum's acid, etc) followed by removal of the protecting group under appropriate conditions (e.g. tetrabutylammonium fluoride in THF for Pg=2-(trimethylsilyl)-ethoxymethyl) then gives the enamine derivatives 16. Appropriate solvents for the two steps are selected from dichloromethane, THF, dioxane, 1,2-dichloroethane, and the reaction is conducted at a temperature from −78° C. to the boiling point of the solvent under an inert atmosphere (nitrogen or argon).

Scheme 7

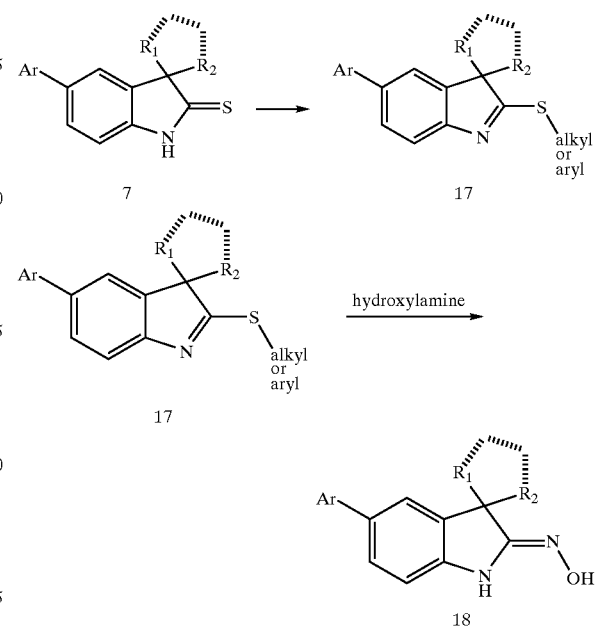

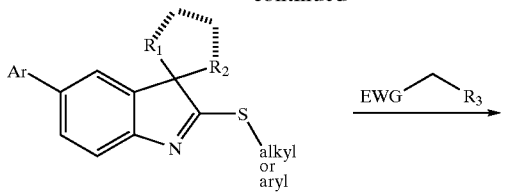

17

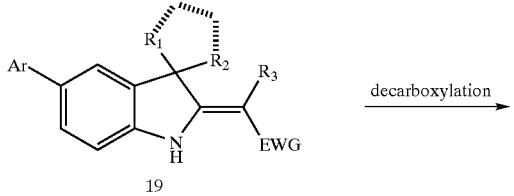

19

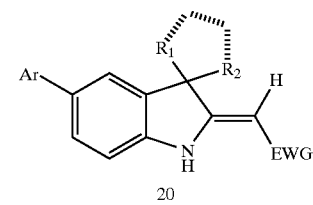

20

According to Scheme 7, treatment of intermediate 7 with an alkylating agent, e.g., methyl iodide, ethyl iodide, 2,4-dinitrofluoro benzene, or 4-nitro fluorobenzene, in the presence of a suitable base (e.g. an amine base such as pyridine, triethylamine or di-iso-propylethylamine or lithium, sodium, potassium or cesium carbonate) in a suitable organic solvent (e.g. DMF, THF, DMSO, dioxane or acetonitrile) at a temperature between −78° C. and the boiling point of the solvent, would then afford thioimino ethers 17. Subsequent reaction of intermediates 17 with hydroxylamine or an acid salt of hydroxylamine (e.g., the hydrochloride) in a suitable solvent (for example but not limited to pyridine methanol, ethanol, iso-propanol, DMF, THF or DMSO and optionally in the presence of an additive such as a tertiary amine base or sodium or potassium acetate) at a temperature between −78° C. and the boiling point of the solvent would then afford the N-hydroxyamidines 18.

Similarly treatment of intermediates 17 with a carbon nucleophile such as a malonate derivative (e.g., malononitrile, a cyano acetate ester, a nitro acetate ester or a malonate) in the presence of a suitable base (e.g. an amine base such as pyridine, triethylamine or di-iso-propylethylamine or lithium, sodium, potassium or cesium carbonate) or a Lewis acid (e.g. boron trifluoride etherate, a lead II salt, titanium tetrachloride, a magnesium II salt, or a silver salt) in a solvent compatible with the chosen base or Lewis acid (e.g. DMF, THF, DMSO, dioxane or acetonitrile, chloroform, benzene, toluene or dichloromethane) would then afford the adduct 19. If the group R₃ in adduct 19 is an ester of a carboxylic acid, then it may be decarboxylated directly to give the enamine derivative 20 by treatment with, e.g. sodium iodide in DMSO at a temperature between room temperature and the boiling point of the solvent. Alternatively the ester may be first hydrolysed to the carboxylic acid (by treatment with an aqueous base (e.g. lithium, sodium, or potassium hydroxide) in a suitable solvent (e.g. THF, dioxane acetonitrile, methanol or ethanol)), followed by decarboxylation in the presence of an acid (e.g. hydrochloric or sulfuric acid) in a suitable solvent (e.g. acetonitrile, THF, dioxane) to afford the derivatives 20. Alternatively the xanthate ester of the carboxylic acid may be prepared by reaction with a base such as sodium or potassium hydride in THF, followed by treatment with carbon disulfide. Subsequent reaction with tributyl tin hydride at elevated temperatures in a solvent such as benzene or toluene under an inert nitrogen or argon atmosphere in the presence of a radical initiator such as benzoyl peroxide or azo-bis-iso-butyronitrile would then give the product 20.

Scheme 8

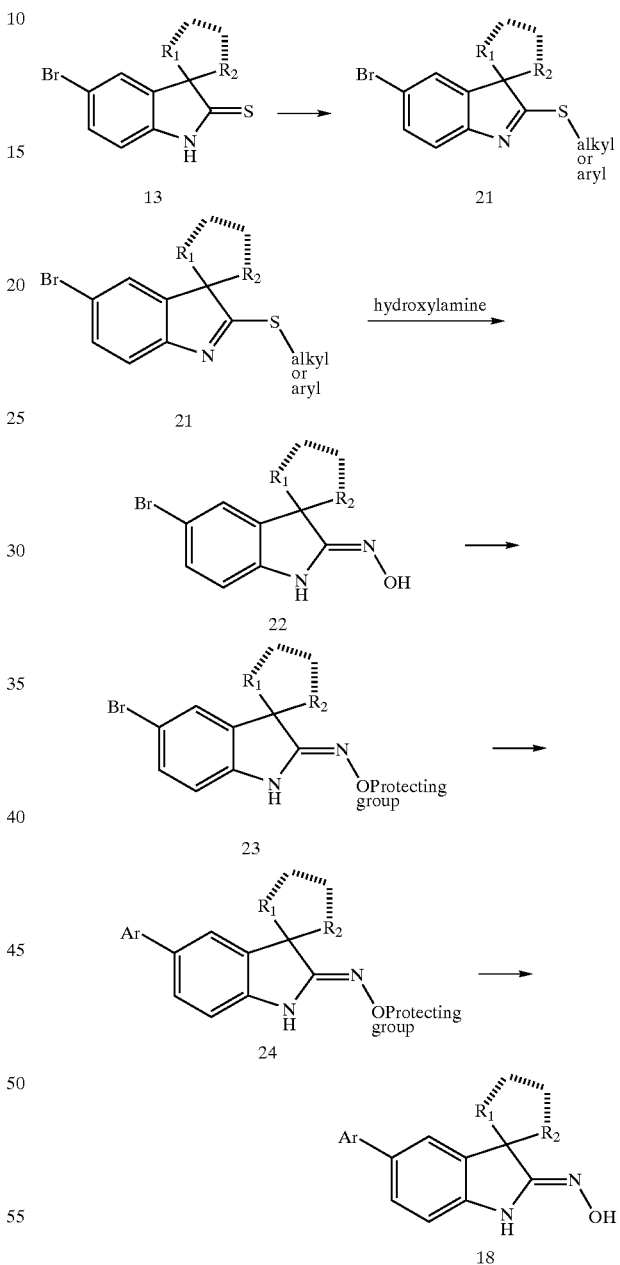

An alternative strategy for synthesizing the product 18 is illustrated by Scheme 8. Thus the bromide 13 (the corresponding chloride, iodide or triflate ester may also be employed) is treated with an alkylating agent, eg methyl iodide, ethyl iodide, 2,4-dinitrofluoro benzene, or 4-nitro fluorobenzene, in the presence of a suitable base (e.g. an amine base such as pyridine, triethylamine or di-iso-propylethylamine or lithium, sodium, potassium or cesium carbonate) in a suitable organic solvent (e.g. DMF, THF, DMSO, dioxane or acetonitrile) at a temperature between −78° C. and the boiling point of the solvent, would then afford thioimino ethers 21. Subsequent reaction of intermediate 21 with hydroxylamine or an acid salt of hydroxylanine (e.g. the hydrochloride, hydrobromide) in a suitable solvent (for example but not limited to pyridine methanol, ethanol, iso-propanol, DMF, THF or DMSO and optionally in the presence of an additive such as a tertiary amine base or sodium or potassium acetate) at a temperature between −78° C. and the boiling point of the solvent, would then afford the N-hydroxyamidine 22. Intermediate 22 could then be protected with a compatible group (e.g. benzyl ether, acyl derivative, tetrahydropyranyl ether, methoxy methyl ether, silyl ether) to give the derivative 23. Alternately compound 21 could be reacted directly with a protected hydroxylamine derivative (chosen, but not limited to the protecting groups described above) to directly afford derivative 23. Compound 23 may then be reacted with a palladium salt (e.g. tetrakis (triphenylphoshine)palladium(0) or palladium acetate), in a suitable solvent (e.g. THF, dimethoxyethane, acetone, ethanol or toluene) at room temperature under an inert atmosphere (argon, nitrogen). The mixture is then treated with an aryl or heteroaryl boronic acid or boronic acid ester and a base (sodium carbonate, triethylamine, potassium phosphate) in water or fluoride source (cesium fluoride) under anhydrous conditions, and the reaction may then be heated to the boiling point of the solvent. The required product 24 is then isolated and purified by standard means.

Compound 24 may then be de-protected under the conditions prescribed by the nature of the protecting group. For example if the protecting group is a benzyl ether then treatment with boron tribromide or trimethylsilyl iodide in a suitable solvent (dichloromethane for example) would afford the compound 18. Other methods to remove the benzyl ether would involve hydrogenation (hydrogen gas or other hydrogen source such as cyclohexadiene or ammonium formate) in the presence of a palladium catalyst. Solvents suitable for such a process include methanol, ethanol, THF, ethyl acetate and dioxane, at a temperature between room temperature and the boiling point of the solvent. If the protecting group was an acetal derivative (tetrahydropyranyl or methoxymethyl ethers) then hydrolysis could be effected under acidic conditions (hydrochloric acid, sulfuric acid, p-toluene sulfonic acid or acidic ion exchange resin) in a solvent such as methanol, ethanol, THF dioxane or acetonitrile. If the protecting group was an acyl derivative (acetate, or benzoate for example) then hydrolysis could be effected under acidic conditions as described above or under basic conditions (lithium, sodium or potassium hydroxide) in a solvent such as an alcohol, THF, dioxane or acetonitrile at a temperature between room temperature and the boiling point of the solvent. If the protecting group was a silyl ether then compound 18 may be prepared by hydrolysing intermediate 24 under the acidic conditions described above or alternately by exposing compound 24 to a fluoride source (eg potassium fluoride, cesium fluoride or tetra butyl ammonium fluoride) in a solvent such as an alcohol, THF, dioxane or acetonitrile at a temperature between room temperature and the boiling point of the solvent. An inert atmosphere of nitrogen or argon may be necessary.

Another method of synthesizing compound 18 would be to convert the protected N-hydroxy amidine 23 into a boronic acid or boronic acid ester (by lithium halogen exchange followed by quench with tri-isopropyl borate, or palladium catalyzed coupling with diboron pinacolate) and then couple this boronic acid or ester derivative with an aryl chloride, bromide, iodide or triflate under a suitable palladium catalysis system as described previously. Subsequent deprotection as described for Scheme 8 would afford the desired compounds 18.

Scheme 9

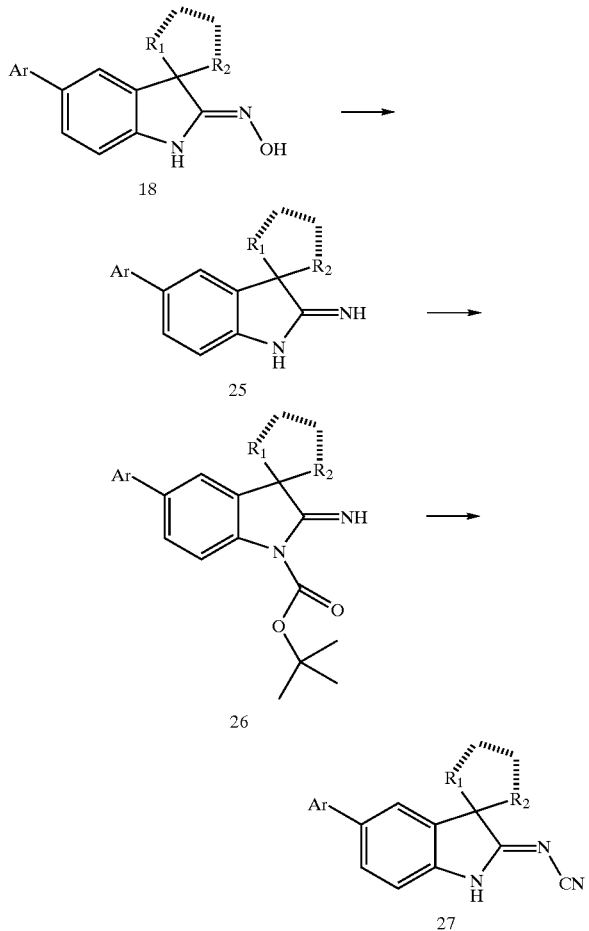

According to Scheme 9, treatment of the N-hydroxyamidine 18 under reducing conditions (e.g. catalytic hydrogenation, iron in acetic acid or hydrazine-raney nickel) would then afford intermediate 25. Solvents suitable for such a process include methanol, ethanol, THF, ethyl acetate and dioxane, at a temperature between room temperature and the boiling point of the solvent. Protection of the secondary nitrogen (a tertiary butyl carbamate is shown as a non-limiting example) under standard conditions would then give compound 26. Reaction of compound 26 with an electrophilic cyanating agent (e.g. cyanogen bromide, N-cyanobenzotriazole or cyanogen bromide/4-dimethylaminopyridine complex) in a suitable solvent (THF acetonitrile or DMF, optionally in the presence of a base such as pyridine or sodium hydride or potassium tert-butoxide) may then afford the desired compound 27. In some cases the cyanation step may occur with concomitant removal of the secondary nitrogen protecting group, if this deprotection does not occur in-situ then a further hydrolysis step would be required.

An alternate synthesis of compound 27 may follow that of compound 18, Scheme 8, where an N-cyanoamidine bromide 28, prepared from compound 22 adopting a similar strategy to the reactions shown in scheme 9, could be coupled with a suitable functionalised aryl boronic acid or boronic acid ester to give compound 27. In another strategy intermediate 28 may be converted into the corresponding boronic acid or boronic acid ester and coupled in a Suzuki or Suzuki type palladium coupling with a suitable functionalised aryl bromide.

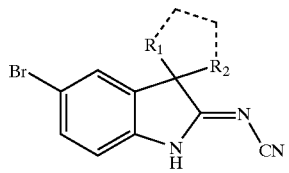

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "prodrug" forms, which, when administered in such form, convert to the active moiety in vivo.

This invention includes pharmaceutical compositions and treatments which comprise administering to a mammal a pharmaceutically effective amount of one or more compounds as described above, or a pharmaceutically acceptable salt thereof, as agonists of the progesterone receptor.

The compounds of this invention have been shown to act as competitive inhibitors of progesterone binding to the PR and act as agonists. These compounds may be used for contraception and post menopausal hormone replacement therapy.

The progesterone receptor agonists of this invention, used alone or in combination, can be utilized in methods of contraception and the treatment and/or prevention of dysfunctional bleeding, uterine leiomyomata, endometriosis; polycystic ovary syndrome, carcinomas and adenocarcinomas of the endometrium, ovary, breast, colon, prostate. Additional uses of the invention include stimulation of food intake.

When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form For most large mammals, the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvents customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

This invention is further understood by the following non-limiting examples.

EXAMPLE 1

5'-(3-Chlorophenyl)spiro[cyclohexane-1,3'-[3H]indole]-2'(1'H)-thione

Spiro[cyclohexane-1,3'-[3H]indol]-2'-(1'H)one

A solution of oxindole (25 g, 0.19 mol) in anhydrous tetrahydrofuran (800 cm$^3$) was cooled to −20° C., then n-butyllithium (2.5M in hexanes, 152 cm$^3$, 0.38 mol) was added slowly followed by N,N,N',N'-tetramethylethylenediamine (51 cm$^3$, 0.38 mol,). After 15 min. 1,5-diiodopentane (174 g, 0.54 mol) was added slowly and the mixture was allowed to warm to room temperature. After stirring for 16 h. saturated aqueous ammonium chloride solution (1 L) and EtOAc (1 L) were added. After 15 min., the layers were separated and the aqueous phase was extracted with EtOAc (×2). The combined organic layers were extracted with hydrochloric acid (1N), then washed with brine (500 cm³), dried (MgSO₄), and concentrated to obtain an oil. The oil was triturated with hexane (200 cm³) and benzene (20 cm³). The precipitate was collected and dried in vacuo to obtain the subtitled compound (26.3 g, 69.6%) as colorless crystals: mp 110–114° C.; $^1$H NMR (DMSO-d₆) δ 1.67 (m, 10H), 6.84 (d, 1H, J=8 Hz), 6.94 (t, 1H, J=8 Hz), 7.17 (t, 1H, J=8 Hz), 7.44 (d, 1H, J=8 Hz), 10.3 (s, 1H).

5'-Bromospiro[cyclohexane-1,3'-[3H]indol]-2'(1'H)-one

To a solution of spiro[cyclohexane-1,3'-[3H]indol]-2'(1'H)-one (17.6 g, 0.09 mol) in acetic acid (300 cm³) was added sodium acetate (8.0 g, 0.1 mol) and bromine (14.6 g, 0.091 mol) with stirring. After 30 min. at room temperature, the reaction mixture was partitioned between water and EtOAc. The aqueous phase was extracted twice with EtOAc. The combined organic layers were washed with water, dried (MgSO₄) and evaporated and the residue was triturated with hexane. The precipitate was collected, and dried in vacuo to obtain the subtitled compound (16.5 g, 67%) as off-white crystals: mp 196–199° C.; $^1$H NMR (DMSO-d₆) δ 1.62 (m, 10H), 6.8 (d, 1H, J=6.8 Hz), 7.36 (d, 1H, J=8.2, 1.8 Hz), 7.58 (dd, 1H, J=8.2, 1.8 Hz), 10.44 (s, 1H).

5-(3-Chlorophenyl)spiro[cyclohexane-1,3-[3H]indol]-2(1H)-one

A solution of 5'-bromospiro[cyclohexane-1,3'-[3H]indol]-2'(1'H)-one (0.32 g, 1.14 mmol) and tetrakis(triphenylphosphine)palladium(0) (0.14 g, 0.12 mmol) in dimethoxyethane (6 cm³) was stirred under N₂ for 20 min. To this mixture was then added 3-chlorophenylboronic acid (0.21 g, 1.37 mmol) and sodium carbonate (0.36 g, 3.4 mmol) in water (3 cm³). The solution was brought to reflux for 6 h then cooled to RT, poured into water and extracted with EtOAc (×3). The combined organic extracts were washed with water, brine, dried (MgSO₄), and evaporated. The residue was purified by column chromatography (SiO₂, ethyl acetate:hexane 1:3) to afford the subtitled compound (0.28 g, 0.89 mmol, 80%) as a yellow solid: mp. 164–165° C., $^1$H NMR (CDCl₃) δ 1.60–1.78 (m, 6H), 1.81–1.99 (m, 4H), 7.04 (d, J=8.1 Hz, 1H), 7.22–7.47 (m, 4H), 7.53 (s, 1H), 7.61 (s, 1H), 9.28 (br s, 1H); $^{13}$C-NMR (CDCl₃) 20.17, 24.12, 31.92 (t), 47.22 (s), 109.21, 121.94, 124.06, 125.50, 125.79, 125.97, 126.38, 128.96 (d), 132.88, 133.59, 135.60, 139.14, 142.17, 182.89 (s); MS (EI) m/z 310, 312 (M–H)⁺; Anal. (C₁₉H₁₈ClNO) C, H, N.

To a solution of 5'-(3-Chlorophenyl)spiro[cyclohexane-1,3'-[3H]indol]-2'(1'H)-one (0.63 g, 2.0 mmol) in dry xylene (20 cm³) under nitrogen was added 2,4-bis(4-methoxyphenyl)-1,3-dithia-2,4-diphosphetane-2,4-disulfide (0.89 g, 2.2 mmol) and the mixture heated under reflux. After 72 h, the mixture was evaporated and the residue subjected to column chromatography (SiO₂, EtOAc:hexane, gradient elution) to afford a solid which was recrystallized from di-iso-propylether/hexane to afford the title compound as yellow crystals (0.17 g, 0.51 mmol, 26%): mp. 223–227° C.; $^1$H-NMR (CDCl₃) δ 1.53–1.66 (m, 8H), 1.83–2.05 (m, 4H), 2.07–2.17 (m, 2H), 7.11 (d, 1H, J=8.0 Hz), 7.31–7.53 (m, 3H), 7.54 (s, 1H), 7.86 (s, 1H), 9.93 (s, 1H, br): MS ((+)APCI) m/z 328 (M+H)⁺.

EXAMPLE 2

3-(1',2'-Dihydro-2'-thioxospiro[cyclohexane-1,3'-[3H]indol]-5'-yl)benzonitrile

To a solution of 5'-bromospiro[cyclohexane-1,3'-[3H]indol]-2'(1'H)-one (1.00 g, 3.57 mmol) in dimethoxyethane (20 cm³) was added tetrakis(triphenylphosphine)palladium (0.20 g, 0.17 mmol). After 15 min. 3-formylphenylboronic acid (1.00 g, 6.93 g) was added followed by potassium carbonate (2.90 g, 21 mmol) in water (10 cm³). After 20 h at reflux, the mixture was cooled poured into water and extracted with EtOAc (×3). The combined organic extract was washed with saturated brine, dried (MgSO₄) and evaporated. The residue was purified by column chromatography (SiO₂, EtOAc:hexane, gradient elution) to afford the title compound (0.66 g, 2.15 mmol, 60%) as a white solid, $^1$H NMR (CDCl₃) δ 1.65–1.85 (m, 6H), 1.86–2.08 (m, 4H), 7.22 (d, 1H, J=8 Hz), 7.48 (dd, 1H, J=8, 2 Hz), 7.61 (t, 1H, J=8 Hz), 7.66 (d, 1H, J=2 Hz), 7.81–7.88 (m, 2H), 8.06 (t, 1H, J=2 Hz), 8.30 (s, 1H, br); MS ((+)ESI) m/z 306 (M+H)⁺.

3-(1',2'-Dihydro-2'-oxospiro[cyclohexane-1,3'-[3H]indol]-5'-yl)benzaldehyde Oxime To a solution of 3-(1',2'-dihydro-2'-oxospirocyclohexane-1,3'-[3H]indol-5'-yl) benzaldehyde (0.59 g, 1.95 mmol) in EtOH: H₂O (10 cm³, 8:2) was added hydroxylamine hydrochloride (0.17 g, 2.5 mmol) and sodium acetate (0.20 g, 2.5 mmol). After 20 min. the mixture was concentrated water was added and the product extracted with EtOAc (×2). The combined organic layers were washed with sat. sodium hydrogen carbonate solution, water, sat. brine, dried (MgSO₄) and evaporated to afford the subtitled oxime (0.63 g, 1.95 mmol, 100%) which was used without further purification, $^1$H NMR (CDCl₃) δ 1.60–1.84 (m, 6H), 1.85–2.00 (m, 4H), 6.86 (d, 1H, J=8 Hz), 7.36 (dd, 1H, J=8, 2 Hz), 7.43–7.50 (m, 1H), 7.57–7.67 (m, 2H), 7.85 (s, 1H, br), 8.25 (s, 1H), 8.68 (s, 1H, br), 8.94 (s, 1H, br); MS ((–)ESI) m/z 319 (M–H)⁻.

3-(1',2'-Dihydro-2'-oxospiro[cyclohexane-1,3'-[3H]indol]-5'-yl)benzonitrile

A solution of 3-(1',2'-Dihydro-2'-oxospiro[cyclohexane-1,3'-[3H]indol-5'-yl) benzaldehyde oxime (0.48 g, 1.49 mmol) in chloroform (10 cm³) was treated with selenium dioxide (0.38 g, 3.50 mmol) and heated under reflux. After 16 h, the mixture was concentrated and the residue purified by column chromatography (SiO₂, EtOAc:hexane 1:4) and the product re-crystallized from EtOAc-hexane to afford the subtitled compound (0.161 g, 0.53 mmol, 35%) as a white solid: mp. 190–191° C.; $^1$H NMR (CDCl₃) δ 1.59–1.87 (m, 6H), 1.88–2.09 (m, 4H), 7.03 (d, 1H, J=8 Hz), 7.42 (dd, 1H, J=8, 2Hz), 7.54 (t, 1H, J=8 Hz), 7.58–7.65 (m, 2H), 7.78 (dt, 1H, J=7, 2 Hz), 7.83 (m, 1H), 8.26 (s, 1H, br); MS ((+) ESI) m/z 303 (M+H)⁺.

Reaction of 3-(1',2'-Dihydro-2'-oxospiro[cyclohexane-1,3'-[3H]indol]-5'-yl) benzonitrile and Lawesson's reagent according to the procedure in example 1 gave the title compound: mp.>231° C. (decomp.); $^1$H NMR (DMSO-d₆) δ 1.38–1.55 (m, 3H), 1.82–1.99 (m, 7H), 7.16 (d, 1H, J=8.1 Hz), 7.63–7.69 (m, 2H), 7.80 (d, 1H, J=7.7 Hz), 8.01 (d, 1H, J=8 Hz) and 12.76 (s, 1H); MS ((–)-APCI) m/z 317 [M–H]⁻.

EXAMPLE 3

4-(1',2'-Dihydro-2'-thioxospiro[cyclohexane-1,3'-[3H]indol]-5'-yl)-2-thiophenecarbonitrile 3-(Trimethylsilyl)-2-thiophenecarbonitrile A solution of 3-bromo-2-thiophenecarbonitrile (0.8 g, 4.3 mmol), tetrakis(triphenylphosphine)palladium(0) (0.25 g, 0.2 mmol) and hexamethylditin (1.4 g, 4.3 mmol) in dimethoxyethane (5 cm³) was heated under reflux for 14 h then cooled to RT. The reaction mixture was absorbed onto florisil and purified by column chromatography (SiO$_2$, methylene chloride:hexane 1:9) to afford the subtitled compound (1.04 g, 3.8 mmol, 90%) as a clear viscous oil: $^1$H NMR (CDCl$_3$) δ 0.35 (s, 9H), 7.56 (d, J=0.9 Hz, 1H), 7.66 (d, J=0.9 Hz, 1H).

4-(1,2-Dihydro-2-oxospiro[cyclohexane-1,3-[3H]indol]-5-yl)-2-thiophenecarbonitrile A solution of the 5'-bromospiro[cyclohexane-1,3'-[3H]indol]-2'(1'H)-one (0.53 g, 1.9 mmol), dichlorobis(triphenylphosphine) palladium(II) (0.1 g, 0.14 mmol) and triphenylarsine (0.14 g, 0.47 mmol) in dimethoxyethane (8 cm$^3$) was stirred under N$_2$ for 20 minutes. To this mixture was then added 3-(trimethylstannyl)-2-thiophenecarbonitrile (0.64 g, 2.35 mmol). The solution was brought to reflux for 32 h. After cooling to room temperature the reaction mixture was absorbed onto florisil and purified by column chromatography (SiO$_2$, ethyl acetate:hexane 2:3) to afford the subtitled compound (0.43 g, 1.39 mmol, 74%) as an off white solid: $^1$H NMR (CDCl$_3$) δ 1.56–2.1 (m, 10H), 6.97 (d, J=8.0 Hz, 1H), 7.39 (dd, J=8.03, 1.45 Hz, 1H), 7.57 (d, J=1.45 Hz, 1H), 7.59 (d, J=1.4 Hz, 1H), 7.84 (d, J=1.4 Hz, 1H), 8.32 (br s, 1H); $^{13}$C-NMR (CDCl$_3$) δ 22.07, 26.56, 34.4 (t), 48.13 (s), 110.18 (d), 111.3, 114.75 (s), 122.92, 126.76 (d), 128.44 (s), 137.55 (d), 138.11, 142.71, 144.49, 182.13 (s); MS (EI) m/z 307 (M–H)$^+$; Anal. (C$_{18}$H$_{16}$N$_2$OS) C, H, N.

A solution of 4-(1,2-dihydro-2-oxospiro[cyclohexane-1,3-[3H]indol]-5-yl)-2-thiophenecarbonitrile (1.0 g, 3.2 mmol) and Lawesson's Reagent (1.3 g, 3.2 mmol) in o-xylene (20 mL) was heated for two and a half hours. The reaction mixture was washed with distilled water (5×100 mL), dried over MgSO$_4$, and evaporated. The product was purified by column chromatography (SiO$_2$, EtOAc:Hexane 1:5) to afford the title compound (0.2 g, 20%) as a pale-yellow solid: m.p. 230–232° C.; $^1$H-NMR (DMSO-d$_6$) δ 12.72 (s, 1H), 8.52 (d, 1H, J=1.5 Hz), 8.36 (d, 1H, J=1.5 Hz), 8.00 (d, 1H, J=1.5 Hz), 7.69 (dd, 1H, J=6,4, 1.8 Hz), 7.10 (d, 1H, J=8.3 Hz), 1.98–1.77 (m, 7H), 1.43–1.33 (m, 3H); MS (EI) M$^+$ @ m/z 324.

EXAMPLE 4

3-(1,2-Dihydro-2-thioxospiro[cyclohexane-1,3-[3H]indol]-5-yl)-5-fluorobenzonitrile To a solution of 5'-bromospiro[cyclohexane-1,3'-[3H]indol]-2'-(1'H)-one (11 g, 0.04 mol) in dry tetrahydrofuran (200 cm$^3$) was added sodium hydride (60% dispersion in mineral oil, 1.6 g, 0.04 mol). After 30 min. stirring at room temperature, the mixture was cooled to −78° C. and butyl lithium (1.7M in hexanes, 23.2 cm$^3$, 0.04 mol) was added slowly. After 30 min. di-iso-propylborate (25 cm$^3$, 0.11 mol) was added and the mixture was allowed to warm to room temperature. After 2 hrs. hydrochloric acid (1N, 500 cm$^3$) and ethylacetate (500 cm$^3$) were added. The aqueous phase was extracted with ethylacetate, then the combined organic layers were washed with water, brine, dried (MgSO$_4$) and evaporated. The residue was triturated with hexane and the precipitate dried in vacuo to obtain (2'-oxo-2,3-dihydrospiro[cyclohexane-1,3'-[3H]indol]-5'-yl) boronic acid (8.3 g, 86%) as an off-white solid that was used without further purification. A sample that was further triturated with ethyl acetate had the following properties: mp. 255–260° C. dec.; $^1$H NMR (DMSO-d$_6$) δ 1.50 (m, 2H), 1.73 (m, 8H), 6.82 (d, 1H, J=7.72 Hz), 7.66 (d, 1H, J=7.72 Hz), 7.91 (s, 3H, br), 10.36 (s, 1H); MS ((−)ESI) m/z 244 [M–H].

3-(1,2-Dihydro-2-oxospiro[cyclohexane-1,3-[3H]indol]-5-yl)-5-fluorobenzonitrile To a solution of 3,5-dibromofluorobenzene in diethyl ether (100 cm$^3$) at −78° C. was added n-butyl lithium (2.5 M, 8 cm$^3$, 20 mmol) dropwise. After 30 min. the mixture was treated with DMF (20 cm$^3$ diethyl ether (10 cm$^3$ stirring was continued at −78° C. After 30 min. the mixture was quenched with dilute HCl aq., separated and the aqueous layer was extracted with EtOAc. The combined organic layers were combined, washed with water, brine, dried (MgSO$_4$) and evaporated to give 3-fluoro-5-bromobenzaldehyde (4.0 g, 19.7 mmol, 100%) as an oil: $^1$H NMR (CDCl$_3$) δ inter alia 7.50–7.53 (m, 2H), 7.82 (s, 1H) and 9.93 (m, 1H); MS (EI) m/z 202, 204 [M$^+$].

To a solution of the last cited compound (4.0 g, 19.7 mmol) in ethanol:water (8:2, 50 cm$^3$), was added sodium acetate (1.72 g, 21 mmol) and hydroxylamine hydrochloride (1.45 g, 21 mmol), and the mixture was heated under reflux. After 30 min., the mixture was cooled, evaporated and the residue partitioned between water and EtOAc. The aqueous layer was re-extracted with EtOAc and the combined organic layers were washed with water, saturated sodium hydrogen carbonate solution, brine, dried (MgSO$_4$) and evaporated to give 3-fluoro-5-bromobenzaldehyde oxime (3.76 g, 17.24 mmol, 87%) which was used without further purification: $^1$H NMR (CDCl$_3$) δ 7.24–7.27 (m, 2H), 7.50 (s, 1H), 7.68 (s, 1H) and 8.04 (s, 1H), MS (EI) m/z 217 [M$^+$].

The above oxime (3.76 g, 17.24 mmol) and copper (II) acetate (370 mg) were dissolved in acetonitrile (100 cm$^3$) under nitrogen and heated under reflux. After 5 h, the mixture was evaporated, the residue taken into EtOAc, washed with sulfuric acid (1N), water, brine, dried (MgSO$_4$) and evaporated to give 3-fluoro-5-bromobenzonitrile (3.08 g, 15.39 mmol, 89%) which was used without further purification.

The above bromide (3.0 g, 15 mmol) and tetrakis(triphenylphosphine)palladium (0) (0.86 g, 0.75 mmol) were dissolved in dimethoxyethane (130 cm$^3$) under nitrogen. After 15 min. (2'-oxo-2,3-dihydrospiro[cyclohexane-1,3'-[3H]indol]-5'-yl) boronic acid (2.82 g, 11.5 mmol) and sodium carbonate (3.1 g, 29.3 mmol) dissolved in water (40 cm$^3$) were added, and the mixture heated under reflux. After 8 h the mixture was cooled, poured into water and extracted with EtOAc (×3). The combined organic layers were then washed with water, dried (MgSO$_4$) and evaporated. The residue was then purified by column chromatography (EtOAc:hexane, gradient elution), and the product recrystallized from methanol to give 3-(1,2-Dihydro-2-oxospiro[cyclohexane-1,3-[3H]indol]-5-yl)-5-fluorobenzonitrile (1.78 g, 5.55 mmol, 48%): mp 199–205° C.; $^1$H NMR (CDCl$_3$) δ 1.64–2.03 (m, 10H), 7.03 (d, 1H, J=8 Hz), 7.31 (dt, 1H, J=7.7 and 1.6 Hz), 7.41 (dd, 1H, J=8, 1.7 Hz), 7.49 (dt, 1H, J=9.6, 2 Hz), 7.58 (d, 1H, J=2 Hz), 7.64 (s, 1H) and 8.37 (s, 1H): MS (EI) m/z 320 [M$^+$].

To a solution of 3-(1,2-Dihydro-2-oxospiro[cyclohexane-1,3-[3H]indol]-5-yl)-5-fluorobenzonitrile (0.32 g, 1.0 mmol) in xylenes (10 cm$^3$) under nitrogen was added Lawesson's reagent (0.89 g, 2.22 mmol) and the reaction was heated under reflux. After 4 h., the mixture was cooled, evaporated and the residue subjected to column chromatography (SiO$_2$, EtOAc:hexane, gradient elution) to afford (0.143 g, 0.42 mmol, 42%) as a white solid: mp. 236–250° C.; $^1$H NMR (CDCl$_3$) δ 1.54–1.66 (m, 3H), 1.86–2.18 (m, 7H), 7.16 (d, 1H, J=8.1 Hz), 7.33–7.36 (m, 1H), 7.46–7.52 (m, 2H), 7.65 (s, 1H), 7.85 (d, 1H, J=1 Hz), 10.05 (s, 1H); MS ((+)-APCI) m/z 337 [M+H]$^+$.

EXAMPLE 5

4-Methyl-5-(1,2-dihydro-2-thioxospiro[cyclohexane-1,3-[3H]-indol]-5-yl)-2-thiophene Thioamide 2'-oxo-2',3'-dihydrospiro[cyclohexane-1,3'-[3H]indol]-5'-yl)boronic acid (2.45 g, 10 mmol), 2-bromo-5-cyano-3-methylthiophene (2.4 g, 12 mmol), potassium (4 g, 29 mmol), and tetrakis(triphenylphosphine)palladium(0) (0.6 g, 0.5 mmol) in dimethoxyethane:water:ethanol (130 cm$^3$, 10:2:1) was heated to 80° C. for 16 h., then poured into 1 L of water, and extracted with EtOAc. The organic layer was washed with brine, dried (MgSO$_4$) and concentrated. The crude product was subjected to column chromatography (SiO$_2$, EtOAc:hexane,1:1) to obtain the title compound (0.9 g, 28%): m p. 200–203° C.; $^1$H NMR (DMSO-d$_6$) δ 1.63 (m, 8H), 1.87 (m, 2H), 2.27 (s, 3H), 6.95 (d, 1H, J=8.13 Hz), 7.34 (dd, 1H, J=8.13, 1.98 Hz), 7.54 (d, 1H, J=1.98 Hz), 7.82 (s, 1H), 10.50 (s, 1H); MS ((+)APCI) m/z 323 [M+H]$^+$.

A solution of 4-methyl-5-[2'-oxo-2'3'-dihydrospiro[cyclohexane-1,3'-[3H]indol]-5'-yl)-2-thiophenecarbonitrile (0.61 g, 1.9 mmol) and phosphorous pentasulfide (0.92 g, 2.1 mmol) in dioxane (17 mL) was heated to 85° C. for 30 minutes. The reaction mixture was poured into distilled water, and washed with aqueous NaHCO$_3$, distilled water, dried over MgSO$_4$, and evaporated to dryness. The residue was purified with column chromatography (2.5% MeOH/CH$_2$Cl$_2$) to afford the title compound (0.05 g, 8%) as a orange-brown solid: m.p. 244–249° C.; $^1$H-NMR (DMSO-d$_6$) δ 12.75 (s, 1H), 9.54 (s, 1H), 9.34 (s, 1H), 7.76 (d, 1H, J=1.5 Hz), 7.58 (s, 1H), 7.45 (dd, 1H, J=6.4, 1.8 Hz), 7.14 (d, 1H, J=7.9 Hz), 2.26 (s, 3H), 1.98–1.89 (m, 7H), 1.83–1.81 (m, 3H); MS ((+)APCI) [M+H]$^+$@m/z 373.

EXAMPLE 6

Pharmacology

The progestational activity for the compounds of the current invention was evaluated in the in-vitro and in-vivo assays described below. In-vitro potencies lie in the range 0.01 nM–10,000 nM, and in-vivo potencies in the range 1 μg/kg to 30 mg/kg.

A. In-vitro Biology

The in-vitro biology is determined by (1) competitive Radioligand Binding: using the A-form of the human progesterone receptor with progesterone as the radioligand; (2) co-transfection assay, which provides functional activity expressed as agonist EC50 and Antagonist IC50 values; (3) a T47D cell proliferation, which is a further functional assay which also provides agonist and antagonist data; and (4) T47D cell alkaline phosphatase assay, which is a further functional assay which also provides agonist and antagonist data.

1. hPR Binding Assay

This assay is carried out in accordance with: Pathirana, C.; Stein, R. B.; Berger, T. S.; Fenical, W.; Ianiro, T.; Mais, D. E.; Torres, A.; Glodman, M. E., *Nonsteroidal human progesterone receptor modulators from the marine alga cymoplia barbata*, J. Steroid Biochem. Mol. Biol., 1992, 41, 733–738.

2. PRE-luciferase Assay in CV-1 Cells

The object of this assay is to determine a compound's progestational or antiprogestational potency based on its effect on PRE-luciferase reporter activity in CV-1 cells co-transfected with human PR and PRE-luciferase plasmids.

The materials methods used in the assay are as follows.

a. Growth Medium:

DMEM (BioWhittaker) containing 10% (v/v) fetal bovine serum (heat inactivated), 0.1 mM MEM non-essential amino acids, 100 U/ml penicillin, 100 mg/ml streptonycin, and 2 mM GlutaMax (GIBCO, BRL). Experimental medium: DMEM (BioWhittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

b. Cell Culture, Transfection, Treatment, and Luciferase Assay

Stock CV-1 cells are maintained in growth medium Co-transfection is done using 1.2×10$^7$ cells, 5 mg pLEM plasmid with hPR-B inserted at Sph1 and BamH1 sites, 10 mg pGL3 plasmid with two PREs upstream of the luciferase sequence, and 50 mg sonicated calf thymus DNA as carrier DNA in 250 ml. Electroporation is carried out at 260 V and 1,000 mF in a Biorad Gene Pulser II. After electroporation, cells are resuspended in growth medium and plated in 96-well plate at 40,000 cells/well in 200 μl. Following overnight incubation, the medium is changed to experimental medium Cells are then treated with reference or test compounds in experimental medium. Compounds are tested for antiprogestational activity in the presence of 3 nM progesterone. Twenty-four hr. after treatment, the medium is discarded, cells are washed three times with D-PBS (GIBCO, BRL). Fifty μl of cell lysis buffer (Promega, Madison, Wis.) is added to each well and the plates are shaken for 15 min in a Titer Plate Shaker (Lab Line Instrument, Inc.). Luciferase activity is measured using luciferase reagents from Promega.

c. Analysis of Results:

Each treatment consists of at least 4 replicates. Log transformed data are used for analysis of variance and nonlinear dose response curve fitting for both agonist and antagonist modes. Huber weighting is used to downweight the effects of outliers. EC$_{50}$ or IC$_{50}$ values are calculated from the retransformed values. JMP software (SAS Institute, Inc.) is used for both one-way analysis of variance and non-linear response analyses.

d. Reference Compounds:

Progesterone and trimegestone are reference progestins and RU486 is the reference antiprogestin. All reference compounds are run in full dose-response curves and the EC$_{50}$ or IC$_{50}$ values are calculated.

TABLE 1

Estimated EC$_{50}$, standard error (SE), and 95% confidence intervals (CI) for reference progestins from three individual studies

| Compound | Exp. | EC50 (nM) | SE | 95% CI lower | 95% CI upper |
|---|---|---|---|---|---|
| Progesterone | 1 | 0.616 | 0.026 | 0.509 | 0.746 |
|  | 2 | 0.402 | 0.019 | 0.323 | 0.501 |
|  | 3 | 0.486 | 0.028 | 0.371 | 0.637 |
| Trimegestone | 1 | 0.0075 | 0.0002 | 0.0066 | 0.0085 |
|  | 2 | 0.0081 | 0.0003 | 0.0070 | 0.0094 |
|  | 3 | 0.0067 | 0.0003 | 0.0055 | 0.0082 |

TABLE 2

Estimated IC$_{50}$, standard error (SE), and 95% confident interval (CI) for the antiprogestin, RU486 from three individual studies

| Compound | Exp. | IC50 (nM) | SE | 95% CI lower | 95% CI upper |
|---|---|---|---|---|---|
| RU486 | 1 | 0.028 | 0.002 | 0.019 | 0.042 |
|  | 2 | 0.037 | 0.002 | 0.029 | 0.048 |
|  | 3 | 0.019 | 0.001 | 0.013 | 0.027 |

Progestational activity: Compounds that increase PRE-luciferase activity significantly ($p<0.05$) compared to vehicle control are considered active.

Antiprogestational activity: Compounds that decrease 3 nM progesterone induced PRE-luciferase activity significantly ($p<0.05$)

EC$_{50}$: Concentration of a compound that gives half-maximal increase PRE-luciferase activity (default-nM) with SE.

IC$_{50}$: Concentration of a compound that gives half-maximal decrease in 3 nM progesterone induced PRE-luciferase activity (default-nM) with SE.

3. T47D Cell Proliferation Assay

The objective of this assay is the determination of progestational and antiprogestational potency by using a cell proliferation assay in T47D cells. A compound's effect on DNA synthesis in T47D cells is measured. The materials and methods used in this assay are as follows.

a. Growth Medium:
DMEM:F12 (1:1) (GIBCO, BRL) supplemented with 10% (v/v) fetal bovine serum (not heat-inactivated), 100 U/ml penicillin, 100 mg/ml streptomyrcin, and 2 mM GlutaMax (GIBCO, BRL).

b. Treatment medium:
Minimum Essential Medium (MEM) (#51200-038GIBCO, BRL) phenol red-free supplemented with 0.5% charcoal stripped fetal bovine serum, 100 U/ml penicillin, 200 mg/ml streptomycin, and 2 mM GlutaMax (GIBCO, BRL).

c. Cell Culture
Stock T47 D cells are maintained in growth medium For BrdU incorporation assay, cells are plated in 96-well plates (Falcon, Becton Dickinson Labware) at 10,000 cells/well in growth medium. After overnight incubation, the medium is changed to treatment medium and cells are cultured for an additional 24 hr before treatment. Stock compounds are dissolved in appropriate vehicle (100% ethanol or 50% ethanol/50% DMSO), subsequently diluted in treatment medium and added to the cells. Progestin and antiprogestin reference compounds are run in full dose-response curves. The final concentration of vehicle is 0.1%. In control wells, cells receive vehicle only. Antiprogestins are tested in the presence of 0.03 nM trimegestone, the reference progestin agonist. Twenty-four hours after treatment, the medium is discarded and cells are labeled with 10 mM BrdU (Amersham Life Science, Arlington Heights, Ill.) in treatment medium for 4 hr.

d. Cell Proliferation Assay
At the end of BrdU labeling, the medium is removed and BrdU incorporation is measured using a cell proliferation ELISA kit (#RPN 250, Amersham Life Science) according to manufacturer's instructions. Briefly, cells are fixed in an ethanol containing fixative for 30 min, followed by incubation in a blocking buffer for 30 min to reduce background. Peroxidase-labeled anti-BrdU antibody is added to the wells and incubated for 60 min. The cells are rinsed three times with PBS and incubated with 3,3'5,5'-tetramethylbenzidine (TMB) substrate for 10–20 min depending upon the potency of tested compounds. Then 25 µl of 1 M sulfuric acid is added to each well to stop color reaction and optical density is read in a plate reader at 450 nm within 5 min.

e. Analysis of Results:
Square root-transformed data are used for analysis of variance and nonlinear dose response curve fitting for both agonist and antagonist modes. Huber weighting is used to downweight the effects of outliers. EC$_{50}$ or IC$_{50}$ values are calculated from the retransformed values. JMP software (SAS Institute, Inc.) is used for both one-way analysis of variance and non-linear dose response analyses in both single dose and dose response studies.

f. Reference Compounds:
Trimegestone and medroxyprogesterone acetate (MPA) are reference progestins and RU486 is the reference antiprogestin. All reference compounds are run in full dose-response curves and the EC$_{50}$ or IC$_{50}$ values are calculated.

TABLE 3

Estimated EC$_{50}$, standard error (SE), and 95% confidence intervals (CI) for individual studies

| Compound | Exp | EC$_{50}$ (nM) | SE | 95% CI lower | 95% CI upper |
|---|---|---|---|---|---|
| Trimegestone | 1 | 0.017 | 0.003 | 0.007 | 0.040 |
|  | 2 | 0.014 | 0.001 | 0.011 | 0.017 |
|  | 3 | 0.019 | 0.001 | 0.016 | 0.024 |
| MPA | 1 | 0.019 | 0.001 | 0.013 | 0.027 |
|  | 2 | 0.017 | 0.00I | 0.011 | 0.024 |

TABLE 4

Estimated IC$_{50}$, standard error, and 95% confident interval for the antiprogestin, RU486

| Compound | Exp | IC$_{50}$ (nM) | SE | 95% CI lower | 95% CI upper |
|---|---|---|---|---|---|
| RU486 | 1 | 0.011 | 0.001 | 0.008 | 0.014 |
|  | 2 | 0.016 | 0.001 | 0.014 | 0.020 |
|  | 3 | 0.018 | 0.001 | 0.014 | 0.022 |

EC$_{50}$: Concentration of a compound that gives half-maximal increase in BrdU incorporation with SE; IC$_{50}$: Concentration of a compound that gives half-maximal decrease in 0.1 trimegestone induced BrdU incorporation with SE 4. T47D Cell Alkaline Phosphatase Assay The purpose of this assay is to identify progestins or antiprogestins by determining a compound's effect on alkaline phosphatase activity in T47D cells. The materials and methods used in this assay are as follows.

a. Culture Medium:
DMEM:F12 (1:1) (GIBCO, BRL) supplemented with 5% (v/v) charcoal stripped fetal bovine serum (not heat-inactivated), 100 U/mil penicillin, 100 µg/ml streptomycin, and 2 mM GlutaMax (GIBCO, BRL).

b. Alkaline Phosphatase Assay Buffer:
I. 0.1 M Tris-HCl, pH 9.8, containing 0.2% Triton X-100;
II. 0.1 M Tris-HCl, pH 9.8 containing 4 mM p-nitrophenyl phosphate (Sigma).

c. Cell Culture and Treatment:
Frozen T47D cells were thawed in a 37° C. water bath and diluted to 280,000 cells/ml in culture medium. To each well in a 96-well plate (Falcon, Becton Dickinson Labware), 180 µl of diluted cell suspension was added. Twenty µl of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 hr.

d. Alkaline Phosphatase Enzyme Assay:

At the end of treatment, the medium was removed from the plate and fifty µl of assay buffer I was added to each well. The plates were shaken in a titer plate shaker for 15 min. Then 150 µl of assay buffer II was added to each well. Optical density measurements were taken at 5 min intervals for 30 min at a test wavelength of 405 nM.

e. Analysis of Results:

Analysis of dose-response data For reference and test compounds, a dose response curve is generated for dose (X-axis) vs. the rate of enzyme reaction (slope) (Y-axis). Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

f. Reference Compounds:

Progesterone and trimegestone are reference progestins and RU486 is the reference antiprogestin. All reference compounds are run in full dose response curves and the $EC_{50}$ or $IC_{50}$ values are calculated.

TABLE 5

Estimated $EC_{50}$, standard error (SE), and 95% confidence intervals (CI) for reference progestins from three independent experiments

| Compound | Exp. | EC50 (nM) | SE | 95% CI lower | 95% CI upper |
|---|---|---|---|---|---|
| Progesterone | 1 | 0.839 | 0.030 | 0.706 | 0.996 |
| | 2 | 0.639 | 0.006 | 0.611 | 0.669 |
| | 3 | 1.286 | 0029 | 1.158 | 1.429 |
| Trimegestone | 1 | 0.084 | 0.002 | 0.076 | 0.091 |
| | 2 | 0.076 | 0.001 | 0.072 | 0.080 |
| | 3 | 0.160 | 0.004 | 0.141 | 0.181 |

TABLE 6

Estimated $IC_{50}$, standard error, and 95% confident interval for the reference antiprogestin RU486 from three independent experiments

| Compound | Exp | IC50 (nM) | SE | 95% CI lower | 95% CI upper |
|---|---|---|---|---|---|
| RU486 | 1 | 0.103 | 0.002 | 0.092 | 0.115 |
| | 2 | 0.120 | 0.001 | 0.115 | 0.126 |
| | 3 | 0.094 | 0.007 | 0.066 | 0.134 |

B. In-vivo Biology

The primary in-vivo assay is the rat decidualization model which may be used to determine progestational effects of both agonists and antagonists. The secondary in-vivo assay is the rat ovulation inhibition model which is under development and hence the protocol is un-available.

1. Rat Decidualization Assay:

The objective of this procedure is used to evaluate the effect of progestins and antiprogestins on rat uterine decidualization and compare the relative potencies of various test compounds. The materials and methods used in this assay are as follows.

a. Methods:

Test compounds are dissolved in 100% ethanol and mixed with corn oil (vehicle). Stock solutions of the test compounds in oil (Mazola™) are then prepared by heating (~80° C.) the mixture to evaporate ethanol. Test compounds are subsequently diluted with 100% corn oil or 10% ethanol in corn oil prior to the treatment of animals. No difference in decidual response was found when these two vehicles were compared.

b. Animals (RACUC Protocol #5002)

Ovariectomized mature female Sprague-Dawley rats (~60-day old and 230 g) are obtained from Taconic (Taconic Farms, N.Y.) following surgery. Ovariectony is performed at least 10 days prior to treatment to reduce circulating sex steroids. Animals are housed under 12 hr light/dark cycle and given standard rat chow and water ad libitum.

c. Treatment

Rats are weighed and randomly assigned to groups of 4 or 5 before treatment. Test compounds in 0.2 ml vehicle are administered by subcutaneous injection in the nape of the neck or by gavage using 0.5 ml. The animals are treated once daily for seven days. For testing antiprogestins, animals are given the test compounds and a $EC_{50}$ dose of progesterone (5.6 mg/kg) during the first three days of treatment. Following decidual stimulation, animals continue to receive progesterone until necropsy four days later.

d. Dosing

Doses are prepared based upon mg/kg mean group body weight. In all studies, a control group receiving vehicle is included. Determination of dose-response curves is carried out using doses with half log increases (e.g. 0.1, 0.3, 1.0, 3.0 mg/kg . . . ).

e. Decidual Induction

Approximately 24 hr after the third injection, decidualization is induced in one of the uterine horns by scratching the antimesometrial luminal epithelium with a blunt 21 G needle. The contralateral horn is not scratched and serves as an unstimulated control. Approximately 24 hr following the final treatment, rats are sacrificed by $CO_2$ asphyxiation and body weight measured. Uteri are removed and trimmed of fat. Decidualized (D-horn) and control (C-horn) uterine horns are weighed separately.

f. Analysis of Results:

The increase in weight of the decidualized uterine horn is calculated by D-horn/C-horn and logarithmic transformation is used to maximize normality and homogeneity of variance. The Huber M-estimator is used to down weight the outlying transformed observations for both dose-response curve fitting and one-way analysis of variance. JMP software (SAS Institute, Inc.) is used for both one-way ANOVA and non-linear dose-response analyses.

g. Reference Compounds:

All progestin reference compounds were run in full dose-response curves and the $EC_{50}$ for uterine wet weight were calculated.

TABLE 7

Estimated $EC_{50}$, standard error (SE), and
95% confidence intervals for individual studies

| Compound | Exp | $EC_{50}$ (mg/kg, s.c.) | SE | 95% CI lower | 95% CI upper |
|---|---|---|---|---|---|
| Progesterone | 1 | 5.50 | 0.77 | 4.21 | 7.20 |
|  | 2 | 6.21 | 1.12 | 4.41 | 8.76 |
| 3-Ketodesogestrel | 1 | 0.11 | 0.02 | 0.07 | 0.16 |
|  | 2 | 0.10 | 0.05 | 0.11 | 0.25 |
|  | 3 | 0.06 | 0.03 | 0.03 | 0.14 |
| Levonorgestrel | 1 | 0.08 | 0.03 | 0.04 | 0.16 |
|  | 2 | 0.12 | 0.02 | 0.09 | 0.17 |
|  | 3 | 0.09 | 0.02 | 0.06 | 0.13 |
|  | 4 | 0.09 | 0.02 | 0.06 | 0.14 |
| MPA | 1 | 0.42 | 0.03 | 0.29 | 0.60 |
|  | 2 | 0.39 | 0.05 | 0.22 | 0.67 |
|  | 3 | 0.39 | 0.04 | 0.25 | 0.61 |

TABLE 8

Estimated average $EC_{50}$, standard error, and 95% confidence intervals
for dose-response curves of 3 reference compounds

| Compound | EC50 (mg/kg, s.c.) | SE | 95% CI lower | 95% CI upper |
|---|---|---|---|---|
| Progesterone | 5.62 | 0.62 | 4.55 | 7.00 |
| 3-Ketodesogestrel | 0.10 | 0.02 | 0.07 | 0.14 |
| Levonorgestrel | 0.10 | 0.01 | 0.08 | 0.12 |

TABLE 9

Estimated $IC_{50}$, standard error, and
95% confident interval for the antiprogestin, RU 486

| Compound | Exp. | $IC_{50}$ (mg/kg, p.o.) | SE | 95% CI lower | 95% CI upper |
|---|---|---|---|---|---|
| RU 486 | 1 | 0.21 | 0.07 | 0.05 | 0.96 |
|  | 2 | 0.14 | 0.02 | 0.08 | 0.27 |

Concentration: Compound concentration in assay (default-mg/kg body weight)

Route of administration: Route the compound is administered to the animals

Body weight: Mean total animal body weight (default-kg)

D-horn: Wet weight of decidualized uterine horn (default-mg)

C-horn: Wet weight of control uterine horn (default-mg)

Decidual response: [(D-C)/C]x100%

Progestational activity: Compounds that induce decidualization significantly (p<0.05) compared to vehicle control are considered active Antiprogestational activity: Compounds that decrease $EC_{50}$ progesterone induced decidualization significantly (p<0.05)

$EC_{50}$ for uterine weight: Concentration of compound that gives half-maximal increase in decidual response (default-mg/kg)

$IC_{50}$ for uterine weight: Concentration of compound that gives half-maximal decrease in $EC_{50}$ progesterone induced decidual response (default-mg/kg)

TABLE 10

Data for Representative Compounds

| Example # | Ki/nM | CV-1 EC50/nM | Ovulation inhibition IC100 mg/kg |
|---|---|---|---|
| 5 |  | 0.3 |  |
| 3 | 0.1 | 0.2 |  |
| 1 | 0.2 | 0.8 |  |
| 4 | 0.06 | 0.1 | 0.1 |

EXAMPLE 7

5-(1,2-Dihydro-2-thioxospiro[cyclopentane-1,3-[3H]indol]-5'-yl)-1H-pyrrole-2-carbonitrile 5-(2'-Oxo-2',3'-dihydrospiro[cyclopentane-1,3'-[3H]indol]-5'-yl-2-cyanopyrrole: A solution of 5'-bromospiro[cyclopentane-1,3'-[3H]indol]-2'(1'H)-one (2.0 g, 7.5 mmol) and tetrakis(triphenylphosphine)palladium(0) (430 mg, 0.3 mmol) in ethylene glycol dimethyl ether (50 mL) was stirred under a flow of nitrogen for 15 min. To the solution was added sequentially 1-t-butoxycarbonylpyrrole-2-boronic acid (2.1 g, 9.7 mmol) and potassium carbonate (2.4 g, 17 mmol) in water (10 mL). The mixture was heated to 80° C. for 3 h and allowed to cool. The reaction mixture was poured into water (50 mL) and extracted with ethyl acetate (3×50 mL). The organic layers were combined, washed with brine (30 mL) and dried over magnesium sulfate. The solution was filtered and concentrated in vacuo. Crystallization from 20% ethyl acetate/hexane gave 2-(1',2'-dihydro-2'-oxospiro[cyclopentane-1,3'-[3H]indol]-5'-yl)-1H-pyrrole-1-carboxylic acid, tert-butyl ester (2.2 g, 83%) as a white powder, mp 179–180.5° C. $^1$H NMR (DMSO-$d_6$, 400 MHz) δ 1.30 (s, 9H), 1.75–1.98 (m, 8 H), 6.16 (dd, 1H, J=1.8, 3.3 Hz), 6.22 ('t', 1H, J=3.3, 3.3 Hz), 6.79 (d, 1H, J=7.9 Hz), 7.08 (dd, 1H, J=1.8, 7.9 Hz), 7.14 ('d', 1H, J=1.5 Hz), 7.28 (dd, J=1.9, 3.3 Hz), 10.30 (s, 1H). MS (EI) m/z 352 [M$^+$]. Anal. Calcd for $C_{21}H_{24}N_2O_3$: C, 71.57; H, 6.86; N, 7.95. Found: C, 71.08; H, 6.83; N, 7.74.

To a solution of 2-(1',2'-dihydro-2'-oxospiro[cyclohexane-1,3'-[3H]indol]-5'-yl)-1H-pyrrole-1-carboxylic acid, tert-butyl ester (2.2 g, 6.0 mmol) in THF (anhydrous, 25 mL) was added at −78° C. chlorosulfonyl isocyanate (0.63 mL, 7.0 mmol). After 90 min, dimethylformamide (11 mL, 140 mmol) was added and the reaction was allowed to warm to room temperature. The reaction mixture was poured into water (50 mL) and extracted with ethyl acetate (2×50 mL). The organic layers were combined, washed with brine (50 mL), dried over magnesium sulfate, filtered and concentrated in vacuo. Purification via flash column chromatography on silica gel (30% ethyl acetate/hexane) gave 5-(2'-oxo-2',3'-dihydrospiro[cyclopentane-1,3'-[3H]indol]-5'-yl-2-cyanopyrrole-1-carboxylic acid, tert-butyl ester (1.7 g, 75%) as white crystals, mp 167–9° C. $^1$H NMR (DMSO-$d_6$, 400 MHz) δ 1.34 (s, 9H), 1,75–1.98 (m, 8H), 6.39 (d, 1H, J=3.7 Hz), 6.84 (d, 1H, J=7.9 Hz), 7.17 (dd, 1H, J=1.8, 7.9 Hz), 7.28 ('t', 2H), 10.41 (s, 1H). MS (ESI) m/z 376 [M−H]$^−$. Anal. Calcd. for $C_{22}H_{23}N_3O_3$: C70.01; H, 6.14; N, 11.13. Found: C, 69.67; H, 6.38; N, 11.04.

5-(2'-Oxo-2',3'-dihydrospiro[cyclopentane-1,3'-[3H]indol]-5'-yl-2-cyanopyrrole-1-carboxylic acid, tert-butyl ester (1 g, 2.7 mmol) was placed in a 25 mL round bottomed flask stoppered with a rubber septum and equipped with nitrogen inlet and a needle to allow gaseous outflow. A vigorous flow of nitrogen was maintained as the flask was placed in an oil bath and heated to 165° C. After 20 min at this temperature, the flask was removed from the oil bath and allowed to cool. Crystallization from ethyl ether gave the title compound (600 mg, 79%) as a yellow powder, mp 285–286° C. $^1$H NMR (DMSO-$d_6$, 400 MHz) δ 1.75–2.03 (m, 8H), 6.60 (dd, 1H, J=2.4, 3.7 Hz), 6.84 (d, 1H, J=8.1 Hz), 6.94 (dd, 1H, J=2.4, 3.7 Hz), 7.52 (dd, 1H, J=1.8, 8.1 Hz), 7.60 (d, 1H, J=1.8 Hz), 10.38 (s, 1H), 12.45 (s, 1H). MS (ESI) m/z 276 [M–H]$^-$. Anal. Calcd. For $C_{17}H_{15}N_3O$: C, 73.63; H, 5.45; N, 15.15. Found: C, 73.24; H, 5.34; N, 14.96.

To 5-(1,2-Dihydro-2-oxospiro[cyclopentane-1,3-[3H]indol]-5'-yl)-1H-pyrrole-2-carbonitrile (0.18 g, 0.7 mmol, 1 eq) in p-xylene (20 mL) was added Lawesson's reagent (0.14 g, 0.36 mmol, 0.5 eq) and the reaction was heated to reflux for 1 hour. The reaction was cooled to room temperature and adsorbed onto silica gel. Purification by flash column chromatography (20% ethyl acetate/hexane) on silica gel gave the product as an orange powder. Further purification by HPLC gave the title compound as a green solid (0.144 g, 70%), mp 275–276° C. (dec.). $^1$H NMR ($d_6$-DMSO, 300 MHz) δ 1.81–2.16 (m, 8H), 6.69 (dd, 1H, J=2.3, 3.7 Hz), 6.98 (dd, 1H, J=1.8, 3.7 Hz), 7.04 (d, 1H, J=8.2 Hz), 7.63 (dd, 1H, J=1.6, 8.2 Hz), 7.72 (d, 1H, J=1.3 Hz), 12.57 (s, 1H), 12.65 (s, 1H). MS (ESI) [M–H]$^-$=292. Anal. Calculated (cald.) for $C_{17}H_{15}N_3S$: C, 69.6; H, 5.15; N, 14.32. Found: C, 69; H, 5.31; N, 13.81.

EXAMPLE 8

5-(1,2-Dihydro-2-thioxospiro[cyclohexane-1,3-[3H]indol]-5-yl)-1-(tert-butoxycarbonyl)-pyrrole-2-carbonitrile To a solution of 5'-bromo-spiro[cyclohexane-1,3'-indolin]-2'-one (3.4 g, 12 mmol) in 1,2-DME (100 mL) under a nitrogen atmosphere was added tetrakis(triphenylphospine)palladium(0) (70 mg, 5 mol %). After 15 min, 2-borono-1H-pyrrole-1-carboxylic acid, 1-tert butyl ester (1.3 eq, 3.31 g, 15.6 mmol) and a solution of $K_2CO_3$ (2.3 eq, 3.83 g, 27.6 mmol) in water (5 mL) were added sequentially. The solution was heated to 80° C. for 3 h and allowed to cool. The reaction mixture was poured into water (200 mL) and extracted with EtOAc (2×100 mL). The organic layers were combined, washed with brine (150 mL) and dried over $MgSO_4$. The solution was filtered, concentrated in vacuo, and the residue was purified by flash column chromatography on silica gel (eluting with 30% EtOAc/hexane) to give 2-(1',2'-dihydro-2'-oxospiro[cyclohexane-1,3'-[3H]indol]-5'-yl)-1H-pyrrole-1-carboxylic acid, tert-butyl ester (3.4 g, 76%) as a white powder, mp 177° C. $^1$H NMR (CDCl$_3$; 300 MHz) δ 1.38 (s, 9H), 1.59–1.93 (m, 10H), 6.18 (m, 1H), 6.23 ('t', 1H, 3 Hz), 6.91 (d, 1H, J=8 Hz), 7.21 (d, 1H, J=8 Hz), 7.34 (m, 1H), 7.44 (s, 1H), 8.3 (br s, 1H, $D_2$Oex). MS ((+)-APCI) m/z 367 [(M+H)$^+$]. Anal. Calcd for $C_{22}H_{26}N_2O_3$: C, 72.11; H, 7.15; N, 7.64. Found: C, 71.7; H, 7.16; N, 7.5.

To a solution of 2-(1',2'-dihydro-2'-oxospiro[cyclohexane-1,3'-[3H]indol]-5-yl)-1H-pyrrole-1-carboxylic acid, tert-butyl ester (0.75 g, 2 mmol) in THF (anhydrous, 20 mL) at −78° C. was added chlorosulfonyl isocyanate (1.15 eq, 0.23 mL, 2.3 mmol). After 90 min, DMF (20 eq, 3.6 mL, 46 mmol) was added and the reaction was allowed to warm to room temperature. The reaction mixture was poured into water (50 mL) and extracted with ethyl acetate (2×50 mL). The organic layers were combined, washed with brine (50 mL), dried over magnesium sulfate, filtered and concentrated in vacuo. Purification via flash column chromatography on silica gel (30% ethyl acetate/hexane) gave 5-(2'-oxo-2',3'-dihydrospiro[cyclohexane-1,3'-[3H]indol]-5'-yl-2-cyanopyrrole-1-carboxylic, acid, tert-butyl ester (0.5 g, 63%) as an oil which crystallized from acetone to give white crystals, mp 156° C. $^1$H NMR ($d_6$-DMSO, 400 MHz) δ 1.32 (s, 9H), 1.50 (m, 3H), 1.60–1.70 (m, 5H), 1.75–1.85 (m, 2H), 6.3 (d, 1H, J=3.7 Hz), 6.87 (d, 1H, J=7.9 Hz), 7.18 (dd, 1H, J=1.5, 7.9 Hz), 7.27 (d, 1H, J=3.7 Hz), 7.48 (d, 1H, J=1.8 Hz), 10.42 (bs, 1H). MS (EI) m/z 391 (M$^+$). Anal. Calcd for $C_{23}H_{25}N_3O_3$: C, 70.57; H, 6.44; N, 10.73. Found: C, 69.82; H, 6.46; N, 10.43.

To a solution of 2-Cyano-5-(1,2-Dihydro-2-.oxospiro[cyclohexane-1,3-[3H]indol]-5-yl)-1H-pyrrole-1-carboxylic acid, tert-butyl ester (0.7 g, 1.8 mmol, 1 eq) in toluene (70 mL) was added Lawesson's reagent (0.47 g, 1.1 mmol, 0.65 eq) and the reaction was heated to reflux for 1 hour. The reaction was cooled to room temperature, poured into water (100 mL) and extracted with ethyl acetate (2×100 mL). The organic layers were combined, washed with brine (50 mL), dried over magnesium sulfate, filtered and concentrated in vacuo. Purification by flash column chromatography (20–30% ethyl acetate/hexane) on silica gel gave title compound as a yellow solid (0.7 g, 96%). $^1$H NMR ($d_6$-DMSO, 500 MHz) δ 1.30–1.98 (m, 19H), 6.45 (d, 1H, J=3.7 Hz), 7.09 (d, 1H, J=7.9 Hz), 7.31–7.34 (m, 2H), 7.81 (d, 1H, J=1.4 Hz), 12.74 (s, 1H). MS (ESI) [M–H]$^-$=406. Anal. calcd. for $C_{23}H_{25}N_3O_2S$: C, 67.79; H, 6.18; N, 10.31. Found: C, 67.86; H, 5.99; N, 10.25.

EXAMPLE 9

5-(1,2-Dihydro-2-thioxospiro[cyclohexane-1,3-[3H]indol]-5-yl)-1-H-pyrrole-2-carbonitrile To a solution of 5-(1,2-Dihydro-2-thioxospiro[cyclohexane-1,3-[3H]indol]-5-yl)-1-(tert-butoxycarbonyl)-pyrrole-2-carbonitrile (0.5 g, 1.2 mmol, 1 eq) in THF (5 mL) was added NaOEt (0.25 g, 3.6 mmol, 3 eq) in EtOH (5 mL) and the reaction was heated to 80° C. for 24 h. The solvents were removed in vacuo and the residue partitioned between ethyl acetate (50 mL) and water (50 mL). The layers were separated and the aqueous layer was extracted with ethyl acetate (50 mL). The organic layers were combined, washed with brine (50 mL), dried over magnesium sulfate, filtered and concentrated in vacuo. Purification by flash column chromatography (30% ethyl acetate/hexane) on silica gel gave the title compound (0.27 g, 68%) as a yellow powder. $^1$H NMR (d6-DMSO, 500 MHz) δ 1.32–1.99 (m, 10H), 6.71 (d, 1H, J=3.7 Hz), 7.00 (d, 1H, J=3.7 Hz), 7.09 (d, 1H, J=8.4 Hz), 7.70 (dd, 1H, J=1.6, 8.4 Hz), 8.05 (d, 1H, J=1.1 Hz), 12.67 (s, 1H), 12.73 (s, 1H). MS (ESI) [M–H]$^-$=306. Anal. calcd. for $C_{18}H_{17}N_3S$: C, 70.33; H, 5.57; N, 13.67. Found: C, 69.64; H, 5.79; N, 13.04.

EXAMPLE 10

5-(2'-Thioxospiro[cyclohexane-1,3'-[3H]indol]-5'-yl)-1-methylpyrrole-2-carbonitrile To a solution of 5-(2'-oxospiro[cyclohexane-1,3'-[3H]indol]-5'-yl)-1-methylpyrrole-2-carbonitrile (0.55 g, 1.8 mmol, 1 eq) in toluene (50 mL) was added Lawesson's reagent (0.47 g, 1.1 mmol, 0.65 eq) and the reaction was heated to 80° C. for 1 hour. The reaction was cooled to room temperature, poured into water (100 mL) and extracted with ethyl acetate (2×100 mL). The organic layers were combined, washed with brine (50 mL), dried over magnesium sulfate, filtered and concentrated in vacuo. Purification by flash column chromatography on silica gel gave the product as a white solid (0.32 g, 55%). $^1$H NMR (d$_6$-DMSO, 500 MHz) δ 1.36–1.99 (m, 10H), 3.7 (s, 3H), 6.35 (d, 1H, J=4.2 Hz), 7.05 (d, 1H, J=4.2 Hz), 7.16 (d, 1H, J=7.9 Hz), 7.44 (dd, 1H, J=1.6, 8.1 Hz), 7.83 (d, 1H, J=1.6 Hz), 12.75 (s, 1H). MS (ESI) [M−H]$^−$=320. Anal. calcd. for C$_{19}$H$_{19}$N$_3$S: C, 70.99; H, 5.96; N, 13.07. Found: C, 68.69; H, 5.36; N, 12.27.

EXAMPLE 11

5-(1,2-Dihydro-2-thioxospiro[cyclopentane-1,3-[3H]indol]-5-yl)-3-thiophenecarbonitrile 5-Bromo-2-thiophenecarbonitrile: A mixture of 5-bromo-2-thiophenecarboxaldehyde (96.0 g, 500 mmol), hydroxylamine hydrochloride (111.9 g, 500 mmol), pyridine (500 mL), and ethanol (500 mL) was heated under nitrogen at reflux for two hours. The reaction mixture was cooled to ambient temperature and concentrated in vacuo to give an oil. The crude product was triturated twice with ice water and the solid obtained was collected on a filter. A mixture of a portion of the above solid (44.31 g, 215 mmol), copper (II) acetate monohydrate (4.2 g, 21 mmol) in acetonitrile (1.4 L) was heated at reflux for three hours. The solvent was removed in vacuo and the residue was dissolved in ethyl acetate. The solution was washed with 5% aqueous sulfuric acid (2×30 mL), water (2×30 mL), brine (20 mL), and dried (MgSO$_4$). The solvent was removed in vacuo and the residue was dissolved in a minimum amount of chloroform (1 L) and allowed to crystallize. The crystal obtained was collected on a filter and the filtrate was concentrated and purified by a chromatography (silica gel, chloroform) to give the subtitled compound as an off-white solid (31.5 g combined, 58%). IR (film) 2200 cm$^{-1}$. $^1$H-NMR (CDCl$_3$) δ 7.39–7.38 (d, 1H, J=4. 1 Hz), 7.10 (d, 1H, J=4.0 Hz); MS (EI) m/z 187 (M$^+$, 98%) 189(M$^+$, 100%).

5-(1,2-dihydro-2-oxospiro [cyclopentane-1,3-[3H]indole]-5-yl)-3-thiophenecarbonitrile was prepared according to the procedure for Example 5 using 5-bromo-2-thiophenecarbonitrile and (2'-oxo-2',3'-dihydrospiro[cyclohexane-1,3'-[3H]indol]-5'-yl) boronic acid: mp. 225–228° C.; $^1$H NMR (DMSO-d$_6$) δ 1.63 (m, 8H), 1.90 (m, 2H), 6.91 (d, 1H, J=8.13 Hz), 7.55 (dd, 1H, J=8.13, 1.76 Hz), 7.60 (d, 1H, J=4.17 Hz), 7.75 (d, 1H, J=1.76 Hz), 7.93 (d, 1H, J=4.17 Hz), 10.51 (s, 1H); MS ((+)APCl) m/z 309 [M+H]$^+$.

A solution of 5-(1,2-dihydro-2-oxospiro[cyclopentane-1,3-[3H]indole]-5-yl)-3-thiophenecarbonitrile (0.66 g, 2.4 mmol), and 2,4-bis(4-methoxyphenyl)-1,3-dithia-2,4-diphosphetane-2,4-disulfide (0.97 g, 2.4 mmol) in toluene (250 ml) was stirred at 80° C. for 2 hours. The solution was concentrated in vacuo. The residue was extracted with ethylacetate, the ethylacetate solution was washed with water, dried over magnesium sulfate, and concentrated. The residue was purified by column chromatography (silica gel, ethylacetate, hexane 20/80) to afford the title compound, mp. 269–272° C. (0.24 g, 32%). $^1$H-NMR (DMSO-d$_6$) δ 2.09 (m, 8H), 7.05 (d, J=8.1 Hz, 1H), 7.55 (dd, J=8.1, 1.7 Hz, 1H), 7.7 (d, J=1.7 Hz, 1H), 7.95 (d, J=1.3 Hz, 1H), 8.49 (d, J=1.3 Hz, 1H), 8.49 (d, J=1.3 Hz, 1H), 12.68 (s, 1H); MS (EI NEG) m/z 309 (M−H)$^−$.

EXAMPLE 12

5-(1,2-Dihydro-thioxospiro(cyclopentane-1,3-[3H]indol)-5-yl)-2-thiophenecarbonitrile The title compound was prepared from 5-(1,2-dihydro-oxospiro(cyclopentane-1,3-[3H]indol)-5-yl)-2-thiophenecarbonitrile (2 g, 6.8 mmol) and Lawesson's reagent (3.32 g, 8.2 mmol) heated to reflux in toluene (150 mL) for 3 hours. Yield 1.5 g (48.3%). m.p. 250–253° C. $^1$H NMR (DMSO-d$_6$) δ 12.75 (s, 1H), 7.98–7.97 (d, 1H, J=3.9 Hz), 7.71–7.70 (d, 1H, J=5.2 Hz), 7.65–7.62 (d, 1H, J=8.1 Hz), 7.09–7.07 (d, 1H, J=8.1 Hz), 2.13–2.08 (m, 6H), 1.99–1.85 (m, 2H); MS. [M−H]$^−$=309 IR (SP ATR) 1430, 1620, 2220 cm$^{-1}$. Anal. calc. for C$_{17}$H$_{14}$N$_2$S$_2$. C, 65.77; H, 4.55; N, 9.02. obs'd C, 65.27; H, 4.41; N, 8.84.

EXAMPLE 13

5-(3-Fluoro-4-methoxyphenyl)spiro[cyclohexane-1,3-[3H]indole]-2(1H)-thione 5-(3-Fluoro-4-methoxyphenyl)spiro[cyclohexane-1,3-[3H]indol]-2(1H)-one: Prepared from 4-bromo-2-fluoroanisole and (2'-oxo-2',3'-dihydrospiro[cyclohexane-1,3'-[3H]indol]-5'-yl) boronic acid according to the procedure for example 5 to afford the subtitled compound as a white solid, mp. 178–180° C.; $^1$H-NMR (DMSO-d$_6$) δ 10.4 (s, 1H), 7.65 (d, 1H, J=1.1 Hz), 7.5–7.4 (m, 3H), 7.2 (t, 1H, J=8.8 Hz), 3.9 (s, 3H), 1.9 (m, 2H), 1.7–1.6 (m, 8H); MS (APCl (−)) m/z 324 [M−H]$^−$; Anal. Calc. For C$_{20}$H$_{20}$FNO$_2$.: C, 73.83, H, 6.20, N, 4.30. Found: C, 73.55, H, 6.23, N, 4.40.

The title compound was prepared by refluxing overnight a mixture of 5-(3-Fluoro-4-methoxyphenyl)spiro[cyclohexane-1,3-[3H]indole]-2(1H)-one and an equal weight of phosphorus pentasulfide in pyridine. Removal of the pyridine in vacuo followed by treatment of the residue with 5N hydrochloric acid solution and subsequent recrystallization in ethanol gave a grey solid, mp 228–229° C.; $^1$H-NMR (DMSO-d$_6$) δ 12.7 (s, 1H), 7.9 (s, 1H), 7.6–7.5 (m, 2H), 7.5–7.4 (m, 1H), 7.2 (t, 1H, J=8.8 Hz), 7.1 (d, 1H, J=8.1 Hz), 3.9 (s, 3H), 1.9–1.8 (m, 7H), 1.4–1.3 (m, 3H); MS (APCl (−)) [M−H]$^−$ m/z 324. Anal. Cal. for C$_{20}$H$_{20}$FNOS. 0.25 H$_2$O C, 69.44; H, 5.97; N, 4.05. Found: C, 69.43; H, 5.75; N, 4.32.

EXAMPLE 14

5-(2-Amino-5-pyrimidinyl)spiro[cyclohexane-1,3-[3H]indole]-2(1H)-thione

Prepared by refluxing overnight a mixture of 5-(2-amino-5-pyrimidinyl)spiro[cyclohexane-1,3-[3H]-indole]-2(1H)-one and an equal weight of phosphorus pentasulfide in pyridine. Removal of the pyridine in vacuo followed by treatment of the residue with 5N hydrochloric acid solution and subsequent recrystallization in ethanol gave a grey solid; mp 274–277° C. (dec.); $^1$H-NMR (DMSO-d$_6$) δ 12.7 (s, 1H), 8.6 (s, 2H), 7.9 (s, 1H), 7.5 (d, 1H, J=8.1 Hz), 7.1 (d, 1H, J=8.1 Hz), 6.8 (s, 2H), 1.9–1.8 (m, 7H), 1.4–1.3 (m, 3H). MS (APCl (−)) [M−H]$^−$ m/z 309.

EXAMPLE 15

3-(1,2-Dihydro-2-thioxospiro[cyclopentane-1,3-[3H]indol]-5-yl)-5-fluorobenzonitrile Spiro[cyclopentane-1,3'-[3H]indol]-2'(1'H)-one To a −25° C. solution of oxindole (2.0 g, 15.0 mmol) in 40 (cm$^3$) of anhydrous THF under N$_2$ was added n-butyllithium (1.6 M in hexanes, 19.7 cm$^3$, 31.5 mmol) drop-wise. To the resulting milky solution was added N,N,N',N'-tetramethylethylenediamine (4.75 cm$^3$, 31.5 mmol). After 30 min. a solution of 1,4-diiodobutane (21.9 g, 70.6 mmol) in THF (3 cm$^3$) was added and the reaction mixture was allowed to warm to RT and stirred for 14 h. The reaction mixture was poured into water, extracted with EtOAc (×2), the combined organic layers were washed with dilute HCl (pH 1) and water (×2), dried (MgSO$_4$) and evaporated. The residue was purified by column chromatography (SiO$_2$, EtOAc:hexane 1:4) to afford the subtitled compound (1.4 g, 7.5 mmol, 50%) as a tan solid: $^1$H NMR (CDCl$_3$) δ 1.8–2.2 (m, 8H), 6.94 (dd, J=7.5, 1.0 Hz, 1H), 7.01 (dd, J=7.5, 1.0 Hz, 1H), 7.14–7.25 (m, 2H), 9.30 (br s, 1H).

5-Bromo-spiro[cyclopentane-1,3'-[3H]indol]-2'(1'H)-one

A solution of spiro[cyclopentane-1,3'-[3H]indol]-2'(1'H)-one (0.27 g, 1.4 mmol) and sodium acetate (0.12 g, 1.46 mmol) in acetic acid (10 cm$^3$) was treated with bromine (0.24 g, 1.51 mmol) in acetic acid (2 cm$^3$). After 30 min. the mixture was poured into sat. sodium hydrogen carbonate solution and extracted with EtOAc (×2), the combined organic layers were washed with water, sat. sodium hydrogen carbonate solution, water, dried (MgSO$_4$), and evaporated to give the subtitled compound (0.37 g, 1.47 mmol, 96%) as an off-white solid which was used without further purification: $^1$H NMR (CDCl$_3$) δ 1.8–2.27 (m, 8H), 6.79 (d, J=8 Hz, 1H), 7.30–7.39 (m, 2H), 8.63 (br s, 1H).

5'-(3-Cyano-5-fluorophenyl)-spiro[cyclopentane-1, 3'-[3H]indol]-2'(1'H)-one

A solution of 3-cyano-5-fluoro-bromobenzene (0.5 g, 2.6 mmol), and tetrakis (triphenylphosphine) palladium(0) (0.2 g) in ethylene glycol dimethyl ether (20 cm$^3$) was stirred under N$_2$ for 20 minutes. To this mixture was then added (spiro[cyclopentane-1,3'-[3H]indol]-2'(1'H)-one-5-yl) boronic acid (0.9 g, 3.9 mmol) and sodium carbonate (0.8 g, 7.8 mmol) in water (5 cm$^3$). The solution was brought to reflux for 18 hours and then cooled to room temperature, poured into 2N NaOH and extracted with EtOAc (×3). The combined extracts were washed with water, brine, dried (MgSO$_4$), and evaporated. The residue was purified by column chromatography (SiO$_2$, EtOAc, hexane) to afford the subtitled compound (0.35 g, 44%) as white needles. mp: 235–237° C.; $^1$H NMR (DMSO-d$_6$) δ 10.5 (s, 1H), 8.1 (s, 1H), 8.0 (dt, 1H, J=1.7, 2.0, 7.0 Hz), 7.8–7.7 (m, 2H), 7.6 (dd, 1H, J=1.8, 6.4 Hz), 6.9 (d, 1H, J=8.1 Hz), 2.0–1.9 (m, 8H); MS (EI) M$^+$@m/z 306.

General Procedure A

The title compound was prepared from 5'-(3-Cyano-5-fluorophenyl)-spiro[cyclopentane-1,3'-[3H]indol]-2'(1'H)-one (40 mg) and Lawesson's reagent (50 mg) in toluene (10 ml) at reflux in a sealed tube for 16 h. The mixture was concentrated and the residue dissolved in a minimal amount of THF, then purified by HPLC (SiO$_2$, 30 cm×2.5 cm, EtOAc-Hexane 2:8 at 20 ml/min.) to afford the title compound (0.022 g) as an off white solid: mp: 236–238° C.; $^1$H NMR (DMSO-d$_6$) δ 12.66 (br s, 1H), 8.11 (s, 1H), 7.97 (dt, 1H, J=10.1 and 2.2 Hz), 7.79–7.76 (m, 2H), 7.68 (dd, 1H, J=8.1 and 1.7 Hz), 7.07 (d, 1H, J=8.1 Hz), 2.10–2.05 (m, 6H) and 1.97–1.88 (m, 2H); MS (EI) m/z 322 [M]$^+$.

EXAMPLE 16

5-(3-Chlorophenyl)-3,3-dimethyl-1,3-dihydro-2H-indole-2-thione 5-(3-Chloro-phenyl)-3,3-dimethyl-1,3-dihydro-indol-2-one
5-bromo-1,3-dihydro-3,3-dimethyl-2H-indol-2-one (0.98 g, 4.07 mol) and tetrakis(triphenylphosphine)palladium(0) (0.239 g) were stirred under an atmosphere of nitrogen in dimethoxyethane (35 cm$^3$). After 15 min., 3-chlorophenylboronic acid (1.27 g, 8.13 mol) was added, followed by potassium carbonate (3.40 g, 45 mmol) in water (15 cm$^3$). The reaction was heated to reflux for 2 hours and then stirred at room temperature overnight. The mixture was diluted with sat. ammonium chloride and extracted with EtOAc (×3). The combined organic layers were dried (MgSO$_4$), filtered, and evaporated. The residue was purified by column chromatography (SiO$_2$, EtOAc:hexane, 1:3) to afford the subtitled compound (0.284 g, 25%): mp 188–189° C.; $^1$H NMR (DMSO-d$_6$) δ 3.34 (s, 6H), 6.93 (d, 1H, J=8.04 Hz), 7.38–7.35 (m, 1H), 7.53–7.43 (m, 2H), 7.61 (d, 1H, J=7.68 Hz), 7.70 (s, 2H), 10.40 (s, 1H); IR (KBr) 3420, 3150, 3050, 1700 cm$^{-1}$; MS (EI) m/z 270 (M−H)$^−$; CHN calculated for C$_{16}$H$_{14}$ClNO+0.1 C$_4$H$_8$O$_2$: C, 70.21; H, 5.32; N, 4.99; Found: C, 70.3; H, 5.44; N, 4.93.

The title compound was prepared from 5-(3-Chlorophenyl)-3,3-dimethyl-1,3-dihydro-indol-2-one (100 mg) and Lawesson's reagent (120 mg) in toluene (10 ml) at reflux, according to General Procedure A, to afford the title compound (0.031 g) as an off white solid: mp. 158–160° C.; $^1$H NMR (CDCl$_3$) δ 9.67 (br s, 1H), 7.55 (s, 1H), 7.47–7.43 (m, 3H), 7.40–7.30 (m, 2H), 7.08 (d, 1H, J=8.7 Hz) and 1.50 (s, 6H); MS (EI) m/z 287/289 [M]$^+$.

EXAMPLE 17

3-Benzyl-5-(3-chlorophenyl)-3-methyl-1,3-dihydro-2H-indole-2-thione

The title compound was prepared from 3-benzyl-5-(3-chloro-phenyl)-3-methyl-1,3-dihydro-indol-2-one (100 mg) and Lawesson's reagent (120 mg) in toluene (10 ml) at reflux, according to General Procedure A, to afford the title compound (0.022 g) as an off white solid: mp. 168–170° C.; $^1$H NMR (CDCl$_3$) δ 9.23 (br s, 1H), 7.49 (s, 1H), 7.49–7.30 (m, 4H), 7.21 (s, 1H), 7.15–7.09 (m, 3H), 6.96–6.94 (m, 2H), 6.89 (d, 1H, J=8.0 Hz), 3.19 (dd, 2H, J=40.5 and 13 Hz) and 1.57 (s, 3H); MS (EI) m/z 363/365 [M]$^+$.

EXAMPLE 18

4-(3,3-Dimethyl-2-thioxo-2,3-dihydro-1H-indol-5-yl)-2-furonitrile 4-(3,3-Dimethyl-2-oxo-2,3-dihydro-1H-indol-5-yl)-furan-2-carbonitrile.

Prepared according to the procedure for Example 5 using (2'-oxo-[2,3-dihydro-3,3-dimethyl-1,3'-[3H]indol]-5'-yl) boronic acid (354 mg, 1.7 mmol) and 4-bromo-furan-2-carbonitrile (200 mg, 1.2 mmol) to afford the subtitled compound (76 mg, 0.3 mmol, 26%) as a white solid: mp. 199.6–201.4° C., $^1$H NMR (DMSO-d$_6$) δ 1.28 (s, 6H), 6.89 (d, J=8.0 Hz, 1H), 7.48 (dd, J=8.0, 1.8 Hz, 1H), 7.65 (d, J=1.5 Hz, 1H), 8.1 (s, 1H), 8.5 (s, 1H), 10.46 (s, 1H); MS (ESI) m/z 251 (M−H)$^−$; Anal. C$_{15}$H$_{12}$N$_2$O$_2$.0.6 H$_2$O.

The title compound was prepared from 4-(3,3-Dimethyl-2-oxo-2,3-dihydro-1H-indol-5-yl)-furan-2-carbonitrile (73 mg) and Lawesson's reagent (120 mg) in toluene (10 ml) at reflux, according to General Procedure A, to afford the title compound (0.003 g) as an off white solid: mp. 188–191° C.; $^1$H NMR (CDCl$_3$) δ 9.63 (br s, 1H), 7.83 (s, 1H), 7.36–7.33 (m, 3H), 7.06 (d, 1H, J=7.9 Hz) and 1.48 (s, 6H), MS (EI) m/z 268 [M]$^+$.

EXAMPLE 19

5-(3-Methoxyphenyl)-3,3-dimethyl-1,3-dihydro-2H-indole-2-thione 5-bromo-1,3-dihydro-3,3-dimethyl-2H-indol-2-one: 3,3-dimethyl-indol-2-one (0.65 g, 4.03 mmol) and sodium acetate (0.33 g, 4.07 mmol) were stirred in acetic acid (5 cm³) then bromine (0.66 g, 4.13 mmol) in acetic acid (5 cm³) was added drop-wise to the reaction mixture. The reaction was stirred for 50 min., then poured into water. The mixture was basified with sodium carbonate, extracted with ethyl acetate (×3), dried (MgSO$_4$), filtered, and evaporated to give the subtitled compound (0.89 g, 92%) $^1$H NMR (DMSO-d$_6$) δ 1.21 (s, 6H), 6.76 (d, 1H, J=8.22 Hz), 7.29 (dd, 1H, J=2.12 Hz, 8.23 Hz), 7.49 (d, 1H, J=2.03 Hz), 10.4 (s, 1H).

5-bromo-1,3-dihydro-3,3-dimethyl-2H-indol-2-one (0.33 g, 1.38 mmol) and tetrakis(triphenylphosphine)palladium(0) (0.094 g) were stirred under an atmosphere of nitrogen in dimethoxyethane (12 cm³). After 15 minutes, 3-methoxyphenylboronic acid (0.42 g, 2.76 mmol) was added, followed by potassium carbonate (1.15 g, 8.34 mmol) in water (5 cm³). The reaction was heated to reflux for 5 hours, and then cooled to room temperature. Saturated aqueous ammonium chloride and EtOAc were added and the mixture was filtered. The aqueous layer was extracted with EtOAc (×2), and the combined organic layers were dried (MgSO$_4$), filtered, and evaporated. The residue was purified by column chromatography (SiO$_2$, EtOAc:hexane 1:3) to afford 5-(3-methoxy-phenyl)-3,3-dimethyl-1,3-dihydro-indol-2-one (0.11 g, 31%), mp=157–158° C.; $^1$H NMR (DMSO-d$_6$) δ 3.34 (s, 6H), 3.82 (s, 3H), 6.87–6.93 (m, 2H), 7.20–7.15 (m, 2H), 7.37–7.32 (m, 1H), 7.49–7.46 (m, 1H), 7.63 (d, 1H, J=1.14 Hz), 10.4 (s, 1H); MS (EI) m/z 266 (M–H)$^-$; CHN calculated for C$_{17}$H$_{17}$NO$_2$: C, 76.38; H, 6.41; N, 5.24; Found: C, 76.02; H, 6.49; N, 5.02.

The title compound was prepared from 5-(3-methoxy-phenyl)-3,3-dimethyl-1,3-dihydro-indol-2-one (100 mg) and Lawesson's reagent (120 mg) in toluene (10 ml) at reflux, according to General Procedure A, to afford the title compound (0.022 as an off white solid: mp. 149–150° C.; $^1$H NMR (CDCl$_3$) δ 9.69 (br s, 1H), 7.49–46 (m, 2H), 7.37 (t, 1H, J=8.0 Hz), 7.16 (d, 1H, J=7.7 Hz), 7.09–7.06 (m, 2H), 6.90 (dd, 1H, J=8.2 and 2.3 Hz), 3.88 (s, 3H) and 1.50 (s, 6H); MS (EI) m/z 283 [M]$^+$.

EXAMPLE 20

3-(1,2-Dihydro-2-thioxospiro[cyclohexane-1,3-[3H]indol]-5-yl)-4-fluorobenzonitrile 3-(1,2-Dihydro-2-oxospiro[cyclohexane-1,3-[3H]indol]-5-yl)-4-fluorobenzonitrile Prepared according to the procedure for Example 5: mp. 205–206° C. $^1$H NMR (DMSO-d$_6$) δ 10.47 (s, 1H), 8.08–8.06 (dd, 1H), 7.89–7.85 (m, 1H), 7.65 (s, 1H), 7.54–7.49 (m, 1H), 7.43–7.40 (tt, 1H), 6.95–6.93 (d, 1H J=7.9 Hz), 1.97–1.83 m, 2H), 1.69–1.55 (m, 8H); MS (EI) m/z 320 (M$^+$).

The title compound was prepared from 3-(1,2-Dihydro-2-oxospiro[cyclohexane-1,3-[3H]indol]-5-yl)-4-fluorobenzonitrile (100 mg) and Lawesson's reagent (120 mg) in toluene (10 ml) at reflux, according to General Procedure A, to afford the title compound (0.037 g) as an off white solid: mp. 230–233° C.; $^1$H NMR (CDCl$_3$) δ 9.82 (br s, 1H), 7.86 (s, 1H), 7.77 (dd, 1H, J=7.0 and 1.8 Hz), 7.68–7.63 (m, 1H), 7.45 (d, 1H, J=8.0 Hz), 7.31 (d, 1H, J=9.0 Hz), 7.15 (d, 1H, J=8.1 Hz), 2.17–1.84 (m, 7H) and 1.60–1.54 (m, 3H); MS (EI) m/z 336 [M]$^+$.

EXAMPLE 21

5-(1,2-Dihydro-2-thioxospiro[cyclohexane-1,3-[3H]indol]-5-yl)-3-pyridinecarbonitrile A solution of 3-bromopyridine-5-carbonitrile (2.79 g, 15.26 mmol), hexamethylditin (5.00 g, 15.26 mmol) and tetrakis(triphenylphosphine)palladium(0) (0.20 g, 0.17 mmol) in anhydrous dimethoxyethane (30 cm³) under N$_2$ was heated under reflux. After 16 h the mixture was concentrated and purified by column chromatography (SiO$_2$, EtOAc:hexane 5:95) to afford 3-cyanopyridine-5-trimethylstannane (2.82 g, 10.55 mmol, 69%): $^1$H NMR (CDCl$_3$) δ 0.40 (s, 9H), 8.01 (m, 1H), 8.80 (m, 2H); MS ((+) APCI) m/z 269 (M+H)$^+$.

A solution of 5'-bromospiro[cyclohexane-1,3'-[3H]indol]-2'(1'H)-one (1.97 g, 7.05 mmol), 3-cyanopyridine-5-trimethylstannane (2.26 g, 8.46 mmol), bis(triphenylphosphine)palladium(II)chloride (0.33 g, 0.47 mmol) and lithium chloride (1.48 g, 35 mmol) in anhydrous toluene (30 cm³) was heated under reflux. After 16 h the mixture was cooled, partitioned between EtOAc and water, the aqueous layer was re-extracted with EtOAc (×2), the combined organic extracts were washed with water, dried (MgSO$_4$) and evaporated. The residue was subjected to column chromatography (SiO$_2$, EtOAc:hexane, 1:2) and then further purified by preparative LC (Primesphere C18, 10 micron, 50×250 mm, MeCN:H$_2$O 1:1, 100 cm³/min., RT 7.92 min.) to afford 3-(1',2'-dihydro-2'-oxospiro[cyclohexane-1,3'-[3H]indol-5'-yl)pyridine carbonitrile as white crystals (0.56 g, 1.84 mmol, 26%): mp. 232–234° C., $^1$H NMR (CDCl$_3$) δ 1.68–1.89 (m, 6H), 1.93–2.13 (m, 4H), 7.12 (d, 1H, J=8 Hz), 7.49 (dd, 1H, J=8, 2 Hz), 7.66 (d, 1H, J=2 Hz), 8.15 (t, 1H, J=2 Hz), 8.39 (s, 1H, br), 8.89 (d, 1H, J=2 Hz), 9.06 (d, 1H, J=2 Hz); MS ((+)-ESI) m/z 304 (M+H)$^+$; Anal. C$_{19}$H$_{17}$N$_3$O CHN.

The title compound was prepared from 3-(1',2'-Dihydro-2'-oxospiro[cyclohexane-1,3'-[3H]indol]-5'-yl)pyridine carbonitrile (100 mg) and Lawesson's reagent (120 mg) in toluene (10 ml) at reflux, according to General Procedure A, to afford the title compound (0.004 g) as. a yellow solid: mp. 237–238° C.; $^1$H NMR (CDCl$_3$) δ 9.56 (br s, 1H), 9.03 (d, 1H, J=1.9 Hz), 8.87 (d, 1H, J=1.4 Hz), 8.12 (s, 1H), 7.87 (s, 1H), 7.50 (d, 1H, J=8.1 Hz), 7.17 (d, 1H, J=8.1 Hz), 2.19–1.85 (m, 7H) and 1.59–1.54 (m, 3H); MS ((–)-APCI) m/z 318 [M–H]$^-$.

EXAMPLE 22

5-(3,4-Difluorophenyl)spiro[cyclohexane-1,3-[3H]indole]-2(1H)-thione

5'-(3,5-Difluorophenyl)spiro[cyclohexane-1,3'-[3H]indol]-2'(1'H)-one

Prepared according to the procedure for Example 5: mp 180–183° C.; $^1$H-NMR (CDCl$_3$) δ 8.35 (s, 1H), 7.59 (d, 1H, J=2.0 Hz), 7.40 (dd, 1H, J=6.2, 2.0 Hz), 7.10–7.03 (m, 2H), 6.99 (d, 1H, J=8.1 Hz), 7.76 (tt, 1H, J=4.3, 2.3 Hz), 2.05–1.62 (m, 10H); MS ((+)APCI) m/z 314 [M+H]$^+$.

The title compound was prepared from 5'-(3,5-difluorophenyl)spiro[cyclohexane-1,3'-[3H]indol]-2'(1'H)-one (100 mg) and Lawesson's reagent (120 mg) in toluene (10 ml) at reflux, according to General Procedure A, to afford the product (0.020 g) as a yellow solid: mp. 232–233° C.; $^1$H NMR (CDCl$_3$) δ 10.05 (br s, 1H), 7.83 (s, 1H), 7.44 (dd, 1H, J=8.1 and 1.4 Hz), 7.38–7.30 (m, 1H), 7.26–7.19 (m, 3H), 7.11 (d, 1H, J=8.1 Hz), 2.17–1.82 (m, 7H) and 1.66–1.53 (m, 3H); MS ((–)-APCI) m/z 328 [M–H]$^-$.

EXAMPLE 23

5-(5-Chloro-2-thienyl)spiro[cyclohexane-1,3-[3H]indole]-2(1H)-thione 5-(5-Chloro-2-thienyl)spiro[cyclohexane-1,3-[3H]indol]-2(1H)-one:

Prepared according to the procedure for Example 5: m.p. 191–192° C., $^1$H NMR (CDCl$_3$) δ 1.6–2.1 (m, 10H), 6.85–6.95 (m, 2H), 6.98 (d, J=4.0 Hz, 1H), 7.36 (dd, J=7.5, 1.6 Hz, 1H), 7.53 (d, J=0.9 Hz, 1H), 7.80 (br s, 1H); $^{13}$C-NMR (THF-d$_8$) δ 21.35, 25.33, 33.12 (t), 48.32 (s), 110.40, 121.66, 121.96, 125.44, 127.25 (d), 128.17, 128.43, 136.92, 140.20, 143.43, 183.72 (s); MS (EI) m/z 318 (M+H)$^+$; Anal. (C$_{17}$H$_{16}$ClNOS) C, H, N.

The title compound was prepared from 5-(5-Chloro-2-thienyl)spiro[cyclohexane-1,3-[3H]indol]-2(1H)-one (100 mg) and Lawesson's reagent (120 mg) in toluene (10 ml) at reflux, according to General Procedure A, to afford the product (0.041 g) as a yellow solid: mp. 231–232° C.; $^1$H NMR (CDCl$_3$) δ 9.75 (br s, 1H), 7.82 (d, 1H, J=1.2 Hz), 7.43 (dd, 1H, J=8.1 and 1.6 Hz), 7.04–7.02 (m, 2H), 6.89 (d, 1H, J=3.8 Hz), 2.15–1.84 (m, 7H) and 1.59–1.52 (m, 3H); MS ((−)-APCI) m/z 332/334 [M−H]$^-$.

EXAMPLE 24

5-(1,2-Dihydro-2-thioxospiro[cyclohexane-1,3-[3H]indol]-5-yl)-3-furancarbonitrile 5-(1',2'-Dihydro-2'-oxospiro[cyclohexane-1,3'-[3H]indol]-5'-yl)-3-furancarbonitrile Prepared according to the procedure for Example 5: m.p. 243–245° C. $^1$H-NMR (DMSO-d$_6$) δ 10.48 (s, 1H), 8.62 (d, 1H, J=0.7 Hz), 7.76 (d, 1H, J=1.5 Hz), 7.58–7.55 (dd, 1H), 7.33 (d, 1H, J=0.7 Hz), 6.92–6.90 (d, 1H, J=8.1 Hz), 1.87–1.83 (m, 2H), 1.73–1.53 (m, 8H). MS ((+)EI) m/z 292 (M$^+$).

The title compound was prepared from 5-(1',2'-dihydro-2'-oxospiro[cyclohexane-1,3'-[3H]indol]-5'-yl)-3-furancarbonitrile (100 mg) and Lawesson's reagent (120 mg) in toluene (10 ml) at reflux, according to General Procedure A, to afford the product (0.020 g) as a yellow solid: mp. 264–268° C.; $^1$H NMR (CDCl$_3$) δ 9.66 (br s, 1H), 7.98 (s, 2H), 7.59 (dd, 1H, J=8.2 and 1.5 Hz), 7.08 (d, 1H, J=8.2 Hz), 6.78 (s, 1H), 2.16–1.85 (m, 7H) and 1.56–1.52 (m, 2H): MS ((−)-APCI) m/z 307 [M−H]$^-$.

EXAMPLE 25

5-(3-Chloro-4-fluorophenyl)spiro[cyclohexane-1,3-[3H]indol]-2(1H)-thione

5'-(3-Chloro-4-fluorophenyl)spiro[cyclohexane-1,3'-[3H]indol]-2'(1'H)-one

Prepared according to the procedure for Example 5: mp 188–189° C.; $^1$H-NMR (CDCl$_3$) δ 7.97 (s, 1H), 7.57–7.54 (m, 2H), 7.41–7.34 (m, 2H), 7.20 (t, 1H, J=8.7 Hz), 9.96 (d, 1H, J=8.1 Hz), 2.04–1.65 (m, 10H); MS ((+)APCI) m/z 330 [M+H]$^+$.

The title compound was prepared from 5'-(3-Chloro-4-fluorophenyl)spiro[cyclohexane-1,3'-[3H]indol]-2'(1'H)-one (100 mg) and Lawesson's reagent (100 mg) in toluene (10 ml) at reflux, according to General Procedure A, to afford the product (0.036 g) as an off white solid: $^1$H NMR (DMSO-d$_6$) δ 12.74 (br s, 1H), 7.92 (d, 1H, J=1.4 Hz), 7.87 (dd, 1H, J=7.1 and 2.3 Hz), 7.70–7.65 (m, 1H), 7.61 (dd, 1H, J=7.1 and 1.5 Hz), 7.49 (t, 1H, J=8.9 Hz), 7.14 (d, 1H, J=8.1 Hz), 1.99–1.82 (m, 7H) and 1.40–1.37 (m, 3H): MS ((−)-APCI) m/z 344/346 [M−H]$^-$.

EXAMPLE 26

5-(3-Chloro-5-fluorophenyl)spiro[cyclohexane-1,3-[3H]indol]-2(1H)-thione

5'-(3-Chloro-5-fluorophenyl)spiro[cyclohexane-1,3'-[3H]indol]-2'(1'H)-one

Prepared according to the procedure for Example 5: mp 178–180° C.; $^1$H-NMR (CDCl$_3$) δ 8.50 (s, 1H), 7.57 (d, 1H, J=1.8 Hz), 7.39 (dd, 1H, J=6.2, 1.9 Hz), 7.33–7.32 (m, 1H), 7.15 (dq, 1H, J=5.7, 1.7, 0.7 Hz), 7.06 (dq, 1H, J=4.2, 1.9, 0.4 Hz), 7.00 (d, 1H, J=8.1 Hz), 2.05–1.64 (m, 10H); MS ((−)ESI) [M−H]$^-$ @m/z 328.

The title compound was prepared from 5'-(3-chloro-5-fluorophenyl)spiro[cyclohexane-1,3'-[3H]indol]-2'(1'H)-one (100 mg) and Lawesson's reagent (100 mg) in toluene (10 ml) at reflux, according to General Procedure A, to afford the product (0.039 g) as an off white solid: $^1$H NMR (DMSO-d$_6$) δ 12.76 (br s, 1H), 7.97 (d, 1H, J=1.1 Hz), 7.67 (dd, 1H, J=8.1 and 1.4 Hz), 7.60–7.54 (m, 2H), 7.40 (dt, 1H, J=8.65 and 2.0 Hz), 7.14 (d, 1H, J=8.1 Hz), 1.99–1.83 (m, 7H) and 1.41–1.38 (m, 3H): MS ((−)-APCI) m/z 344/346 [M−H]$^-$.

EXAMPLE 27

5-(3,5-Difluorophenyl)spiro[cyclohexane-1,3-[3H]indole]-2(1H)-thione

5'-(3,5-Difluorophenyl)spiro[cyclohexane-1,3'-[3H]indol]-2'(1'H)-one

Prepared according to the procedure for Example 5: mp 180–183° C.; $^1$H-NMR (CDCl$_3$) δ 8.35 (s, 1H), 7.59 (d, 1H, J=2.0 Hz), 7.40 (dd, 1H, J=6.2, 2.0 Hz), 7.10–7.03 (m, 2H), 6.99 (d, 1H, J=8.1 Hz), 7.76 (tt, 1H, J=4.3, 2.3 Hz), 2.05–1.62 (m, 10H); MS ((+)APCI) m/z 314 [M+H]$^+$.

The title compound was prepared from 5'-(3,5-difluorophenyl)spiro[cyclohexane-1,3'-[3H]indol]-2'(1'H)-one (100 mg) and Lawesson's reagent (100 mg) in toluene (10 ml) at reflux, according to General Procedure A, to afford the title compound 0:029 g as an off white solid: $^1$H NMR (DMSO-d$_6$) δ 12.76 (br s, 1H), 7.84 (s, 1H), 7.64–7.56 (m, 1H), 7.46 (d, 1H, J=8.1 Hz), 7.40–7.32 (m, 1H), 7.22–7.15 (m, 2H), 1.99–1.80 (m, 7H) and 1.38–1.35 (m, 3H); MS ((−)-APCI) m/z 328 [M−H]$^-$.

EXAMPLE 28

5-(1,2-Dihydro-2-thioxospiro[cyclohexane-1,3-[3H]indol]-5-yl)-4-propyl-2-thiophenecarbonitrile 5-(1,2-Dihydro-2-oxospiro[cyclohexane-1,3-[3H]indol]-5-yl)-4-propyl-2-thiophenecarbonitrile. The title compound was prepared in a manner similar to Example 5 from 5-bromo-4-n-propyl thiophene-2-carbonitrile (1.17 g, 5 mmol), (1,2-dihydro-2-oxospiro[cyclohexane-1,3-[3H]indol)-5-boronic acid (1.24 g, 5 mmol), tetrakis(triphenylphosphine)palladium, potassium carbonate (2.75 g, 21 mmol), water (10 mL), and dimethoxyethane (50 mL) heated at reflux over night, to afford the product (0.7 g, 40%): m.p.168–171° C.; $^1$H NMR (DMSO-d$_6$) δ 10.56 (s, 1H), 7.93 (s, 1H), 7.52–7.51 (d, 1H, J=1.5 Hz), 7.33–7.29 (dd, 1H, J=1.6 Hz), 7.00–6.96 (d, 1H, J=8.0 Hz), 2.62–2.57 (t, 2H), 1.86 (m, 2H), 1.70–1.56 (m, 11H), 0.88–0.84 (t, H); MS m/z (APCI (+)) 351 [M+H]$^+$. IR (KBr) 1620, 1700, 2200 cm$^{-1}$. Anal. calc. for C$_{21}$H$_{22}$N$_2$OS.1/2 H$_2$O C, 70.2; H, 6.39; N, 7.79. Observed. C, 70.67; H, 6.34; N, 7.62.

The title compound was prepared from 5-(1,2-dihydro-2-oxospiro[cyclohexane-1,3-[3H]indol]-5-yl)-4-propyl-2-thiophenecarbonitrile (90 mg) and Lawesson's reagent (90 mg) in toluene (10 ml) at reflux, according to General Procedure A, to afford the title compound (0.037 g) as an orange solid: $^1$H NMR (DMSO-$d_6$) δ 12.83 (br s, 1H), 7.96 (s, 1H), 7.77 (s, 1H), 7.44 (d, 1H, J=7.7 Hz), 7.19 (d, 1H, J=8.0 Hz), 2.60 (t, 2H, J=8.0 Hz), 1.98–1.79 (m, 7H), 1.64–1.56 (m, 2H), 1.39–1.35 (m, 2H) and 0.87 (t, 3H, J=7.3 Hz):MS ((−)-APCI) m/z 365 [M−H]$^-$.

EXAMPLE 29

5-(3-Fluoro-4-nitrophenyl)spiro[cyclohexane-1,3-[3H]indol]-2(1H)-thione 5-(3-Fluoro-4-nitrophenyl)spiro[cyclohexane-1,3-[3H]indol]-2(1H)-one: Prepared from (2'-oxo-2,3-dihydrospiro[cyclohexane-1,3'-[3H]indol]-5'-yl)boronic acid (3.2 g, 12.5 mmol) and 4-bromo-2-fluoro-nitrobenzene (3 g, 13.6 mmol) as described for example 5, to afford the title compound (0.7 g, 16%) as a yellow solid: mp. 213–215° C.; $^1$H NMR (DMSO-$d_6$) δ 1.5–1.8 (m, 8H), 1.8–2.0 (m, 2H), 6.96 (d, 1H, J=8.13 Hz), 7.68 (dd, 1H, J=8.13, 1.76 Hz), 7.74 (dd, 1H, J=8.68, 1.76 Hz), 7.86 (d, 1H, J=1.98 Hz), 7.92 (dd, 1H, J=13.4, 1,76 Hz), 8.18 (t, 1H, J=8.46 Hz) and 10.52 (s, 1H); MS (EI) m/z=340 (M$^+$).

The title compound was prepared from 5-(3-fluoro-4-nitrophenyl)spiro[cyclohexane-1,3-[3H]indol]-2(1H)-one (90 mg) and Lawesson's reagent (90 mg) in toluene (10 ml) at reflux, according to General Procedure A, to afford the product (0.021 g) as a yellow solid: $^1$H NMR (DMSO-$d_6$) δ 12.82 (br s, 1H), 8.21 (t, 1H, J=8.4 Hz), 8.07 (d, 1H, J=1 Hz), 7.98 (dd, 1H, J=13.1 Hz), 7.79 (dt, 1H, J=8.1 and 2.6 Hz), 7.19 (1H, J=8.2 Hz), 1.99–1.83 (m, 7H) and 1.42–1.39 (m, 3H): MS ((−)-APCI) m/z 355 [M−H]$^-$.

EXAMPLE 30

4-(1,2-Dihydro-2-thioxospiro[cyclohexane-1,3-[3H]indol-5-yl)-2-furancarbonitrile 4-(1,2-Dihydro-2-oxospiro[cyclohexane-1,3-[3H]indol]-5-yl)-2-furancarbonitrile: A solution of 3-bromo-5-cyanofuran (0.75 g, 4.4 mmol), and tetrakis(triphenylphosphine)palladium(0) (0.4 g) in ethylene glycol dimethyl ether (20 cm$^3$) was stirred under $N_2$ for 20 minutes. To this mixture was then added (spiro[cyclohexane-1,3'-[3H]indol]-2'(1'H)-one-5-yl) boronic acid (1.6 g, 6.5 mmol) and sodium acetate (1.4 g, 13.1 mmol) in water (5 cm$^3$). The solution was brought to reflux for 18 hours and then cooled to room temperature, poured into 2N NaOH and extracted with EtOAc (×3). The combined extracts were washed with water, brine, dried (MgSO$_4$), and evaporated. The residue was purified by column chromatography (SiO$_2$, EtOAc, hexane) to afford the product (0.45 g, 36%) as an off-white solid. mp: 240–242° C.; $^1$H NMR (DMSO-$d_6$) δ 10.4 (s, 1H), 8.5 (s, 1H), 8.2 (s, 1H), 7.7 (s, 1H), 7.5 (dd, 1H, J=1.5 6.5 Hz), 6.9 (d, 1H, J=8.0 Hz), 2.0–1.6 (m, 10H); MS (EI) M$^+$ @m/z292.

The title compound was prepared from 4-(1,2-dihydro-2-oxospiro[cyclohexane-1,3-[3H]indol]-5-yl)-2-furancarbonitrile (67 mg) and Lawesson's reagent (67 mg) in toluene (10 ml) at reflux, according to General Procedure A, to afford the title compound (0.018 g) as a yellow solid: $^1$H NMR (DMSO-$d_6$) δ 12.74 (s, 1H), 8.68 (s, 1H), 8.26 (s, 1H), 7.96 (s, 1H), 7.62 (dd, 1H, J=8.0 and 1.0 Hz), 7.10 (s, 1H, J=8.1 Hz), 1.94–1.78 (m, 7H) and 1.35–1.32 (m, 3H): MS ((−)-APCI) m/z 307 [M−H]$^-$.

EXAMPLE 31

5''-(3-Chlorophenyl)spiro[cyclobutane-1,3''-[3H]indol]-2''(1''H)-thione

5-Bromospiro[cyclobutane-1,3-[3H]indol]-2(1H)-one: To a stirred solution of spiro[cyclobutane-1,3'-[3H]indol]-2'(1'H)-one (*J. Med. Chem.* 1987, 824–9) (1.0 g, 6 mmol) in glacial acetic acid (10 mL) was added dropwise at room temperature a solution of bromine (0.30 mL, 6 mmol) in glacial acetic acid (6 mL). After stirring for 10 min, anhydrous sodium acetate (0.47 g, 6 mmol) was added and the solution was concentrated in vacuo. The residue was dissolved in ethyl ether (50 mL) and washed sequentially with water (50 mL), aqueous saturated sodium bicarbonate solution (50 mL), water (50 mL) and brine (30 mL). The organic layer was dried over magnesium sulfate, filtered and concentrated in vacuo. Crystallization from ethyl ether yielded the product as a white fluffy solid (1.1 g, 73%), mp 235–7° C. $^1$H NMR (DMSO-$d_6$, 300 MHz) δ 2.15–2.41 (m, 6H), 6.74 (d, 1H, J=8.2 Hz), 7.33 (dd, 1H, J=2, 8.2 Hz), 7.75 (d, 1H, J=2 Hz), 10.36 (bs, 1H). MS (EI) m/z 251 [M$^+$]. Anal. Calcd for $C_{11}H_{10}BrNO$: C, 52.41; H, 4.00; N, 5.56. Found: C, 51.98; H, 4.24; N, 5.42.

To a solution of 5-bromospiro[cyclobutane-1,3-[3H]indol]-2(1H)-one (0.6 g, 2 mmol) in ethylene glycol dimethyl ether (50 mL) under a nitrogen atmosphere was added tetrakis(triphenylphosphine)palladium(0) (140 mg, 0.1 mmol). To the solution was added sequentially 3-chlorophenyl boronic acid (0.48 g, 3 mmol) and potassium carbonate (0.76 g, 5 mmol) in water (5 mL). The mixture was heated to 80° C. for 3 h and allowed to cool. The reaction mixture was poured into water (100 mL) and extracted with ethyl acetate (3×100 mL). The organic layers were combined, washed with brine (50 mL) and dried over magnesium sulfate. The solution was filtered, concentrated in vacuo, and the residue was purified by HPLC (Zorbax PRO, C18, 10u, 15A, 50×250 mm, 35% Water/65% AcCN; 254 NM; AMB. temp.) to give 5-(3-chlorophenyl)spiro[cyclobutane-1,3-[3H]indole]-2(1H)-one (200 mg, 35%) as a white powder, mp 199.5–201° C. $^1$H NMR (DMSO-$d_6$, 300 MHz) δ 2.21–2.28 (m, 2H), 2.40–2.45 (m, 4H), 6.87 (d, 1H, J=8.1 Hz), 7.37 ('d', 1H), 7.44–7.52 (m, 2H), 7.65 (bd, 1H, J=7.8 Hz), 7.76 (bs, 1H), 7.92 (bs, 1H), 10.35 (s, 1H). MS (EI) m/z 283 [M$^+$]. Anal. Calcd for $C_{17}H_{14}ClNO$: C, 71.96; H, 4.97; N, 4.94. Found: C, 70.75; H, 5.07; N, 4.68.

The title compound was prepared from 5-(3-Chlorophenyl)spiro[cyclobutane-1,3-[3H]indole]-2(1H)-one (55 mg) and Lawesson's reagent (55 mg) in toluene (10 ml) at reflux, according to General Procedure A, to afford the title compound 0.016 g as an orange solid: $^1$H NMR (DMSO-$d_6$) δ 12.58 (br s, 1H), 8.07 (d, 1H, J=1.5 Hz), 7.82 (t, 1H, J=1.7 Hz), 7.70 (d, 1H, J=7.74 Hz), 7.60 (dd, 1H, J=8.12 and 1.71 Hz), 7.49 (t, 1H, J=7.9 Hz), 7.41 (d, 1H, J=8.32 Hz), 7.05 (d, 1H, J=8.14 Hz) and 2.57–2.27 (m, 6H); MS ((−)-APCI) m/z 298/300 [M−H]$^-$.

EXAMPLE 32

5''-(2-Chlorophenyl)spiro[cyclohexane-1,3''-[3H]indol]-2''(1''H)-thione

The title compound was prepared from 5''-(2-Chlorophenyl)spiro[cyclohexane-1,3''-[3H]indole]-2''(1''H)-thione (90 mg) and Lawesson's reagent (90 mg) in toluene (10 ml) at reflux, according to General Procedure A, to afford the product 0.042 g as an off white solid: $^1$H NMR (DMSO-$d_6$) δ 12.75 (br s, 1H), 7.80 (d, 1H, J=1.1 Hz), 7.58–7.55 (m, 1H), 7.48–7.36 (m, 4H), 7.16 (d, 1H, J=8.0 Hz); MS ((−)-APCI) m/z 326/328 [M−H]$^-$.

EXAMPLE 33

5''-(4-Chlorophenyl)spiro[cyclohexane-1,3''-[3H]indole]-2''(1''H)-thione

The title compound was prepared from 5-(4-chlorophenyl)spiro[cyclohexane-1,3-[3H]indol]-2(1H)-one (90 mg) and Lawesson's reagent (90 mg) in toluene (10 ml) at reflux, according to General Procedure A, to afford the product 0.035 g as an off white solid: $^1$H NMR (DMSO-$d_6$) δ 12.74 (br s, 1H), 7.91 (d, 1H, J=1.3 Hz), 7.69 (d, 2H, J=5.5 Hz), 7.60 (dd, 1H, J=8.1 and 1.4 Hz), 7.50 (d, 2H, J=8.5 Hz), 7.15 (d, 1H, J=8.1 Hz), 1.99–1.83 (m, 7H) and 1.50–1.36 (m, 3H); MS ((−)-APCI) m/z 326/328 [M−H]$^-$.

EXAMPLE 34

5-(1",2"-Dihydro-2"-thioxospiro[cyclohexane-1,3"-[3H]indol]-5"-yl)-4-methyl-2-thiophenecarbonitrile 5-Bromo-4-methyl-2-thiophene carboxaldehyde: To a solution of diethylamine (28 g, 0.383 mol) in anhydrous THF (400 mL) was added at −40° C. under nitrogen a solution of n-BuLi (2.5 M, 153 mL, 0.383 mol) in hexane. After addition, the solution was stirred at −40° C. under nitrogen for 30 minutes, cooled to −78° C. and treated dropwise with a solution of 2-bromo-3-methylthiophene (45 g, 0.254 mol) in anhydrous THF (450 mL). The reaction solution was stirred at −78° C. for 30 minutes and treated with anhydrous DMF (100 mL). The mixture was allowed to warm to ambient temperature and was quenched with 1N aqueous hydrochloride solution (1 L). The solution was extracted with ethyl acetate (3×450 mL) and the extracts washed with water, brine and dried (MgSO$_4$). After removal of solvent in vacuo, the title compound was obtained as a white solid (46 g, 88.3%). A sample of the product was crystallized from hexane: mp 63–65° C.; IR (KBr) 1654 cm$^{-1}$. $^1$H-NMR (CDCl$_3$) δ 9.75 (s, 1H), 7.45 (s, 1H), 2.26 (s, 3H); MS (EI) m/z 204/206 (M$^+$). Anal. Calc. For $C_6H_5BrOS$: C, 35.14; H, 2.46. Found: C, 35.00; H, 2.44.

5-Bromo-4-methyl-2-thiophenecarbonitrile: Prepared from 5-bromo-4-methyl-2-thiophene carboxaldehyde using the procedure of Example 5. White solid: mp 40–42° C.; IR (KBr) 2200 cm$^{-1}$; $^1$H-NMR (CDCl$_3$) δ 7.29 (s, 1H), 2.21 (s, 3H). MS (EI) m/z 201/203 (M$^+$, 98%/100%); Anal. Calc. For $C_6H_4BrNS$: C, 35.66; H, 1.99; N, 6.93. Found: C, 36.00; H, 2.14; N, 6.76.

Prepared according to the procedure for Example 5 using (2'-oxo-[2,3-dihydro-3,3-dimethyl-1,3'-[3H]indol]-5'-yl) boronic acid (357 mg, 1.7 mmol) and 5-bromo-4-methylthiophene-2-carbonitrile (295 mg, 1.5 mmol) to afford 5-(3,3-Dimethyl-2-oxo-2,3-dihydro-1H-indol-5-yl)-4-methyl thiophene-2-carbonitrile (227 mg, 0.8 mmol, 55%) as a white solid: mp. 192.3–193° C., $^1$H NMR (DMSO-$d_6$) δ 1.29 (s, 6H), 2.29 (s, 3H), 6.97 (d, J=8.0 Hz, 1H), 7.34 (dd, J=8.0, 1.8 Hz, 1H), 7.49 (d, J=1.7 Hz, 1H), 7.84 (s, 1H), 10.57 (s, 1H); MS (EI) m/z 282 (M)$^+$; Anal. $C_{16}H_{14}N_2OS$.

The title compound was prepared from 5-(3,3-dimethyl-2-oxo-2,3-dihydro-1H-indol-5-yl)-4-methyl thiophene-2-carbonitrile (0.77 g, 2.39 mmol) and phosphorous pentasulfide (0.42 g, 0.96 mmol) in toluene (20 ml) at reflux. After 3 h, the reaction was cooled and partitioned between water and EtOAc, the organic layer was separated, dried (MgSO$_4$) and evaporated. The residue was purified by column chromatography (SiO$_2$, EtOAc-hexane gradient elution) to afford the product (0.25 g, 0.73 mmol, 30%) as an orange solid: $^1$H NMR (DMSO-$d_6$) δ 12.82 (br s, 1H), 7.88 (s, 1H), 7.82(d, 1H, J=2 Hz), 7.49 (dd, 1H, J=8.1, 1.6 Hz), 7.18 (d, 1H, J=8.1 Hz), 1.99–1.80 (m, 7H) and 1.40–1.36 (m, 3H); MS ((−)-APCI) m/z 321 [M−H]$^-$.

EXAMPLE 35

5-(1",2"-Dihydro-2"-thioxospiro[cyclohexane-1,3"-[3H]indol]-5"-yl)-2-thiophenecarbonitrile 5-Bromo-2-thiophenecarbonitrile: A mixture of 5-bromo-2-thiophene carboxaldehyde (96.0 g, 500 mmol), hydroxylamine hydrochloride (111.9 g, 500 mmol), pyridine (500 mL), and ethanol (500 mL) was heated under nitrogen at reflux for two hours. The reaction mixture was cooled to ambient temperature and concentrated in vacuo to give an oil. The crude product was triturated twice with ice water and the solid obtained was collected on a filter. A mixture of a portion of the above solid (44.31 g, 215 mmol), copper (II) acetate monohydrate (4.2 g, 21 mmol) in acetonitrile (1.4 L) was heated at reflux for three hours. The solvent was removed in vacuo and the residue was dissolved in ethyl acetate. The solution was washed with 5% aqueous sulfuric acid (2×30 mL), water (2×30 mL), brine (20 mL), and dried (MgSO$_4$). The solvent was removed in vacuo and the residue was dissolved in a minimum amount of chloroform (1 L) and allowed to crystallize. The crystals obtained were collected on a filter and the filtrate was concentrated and purified by a chromatography (silica gel, chloroform) to give the subtitled compound as an off-white solid (31.5 g combined, 58%). IR (film) 2200 cm$^{-1}$. $^1$H-NMR (CDCl$_3$) δ 7.39–7.38 (d, 1H, J=4.1 Hz), 7.10 (d, 1H, J=4.0 Hz); MS (EI) m/z 187 (M$^+$, 98%) 189 (M$^+$, 100%).

5-(2'-Oxo-2',3'-dihydrospiro[cyclohexane-1,3'-[3H]indol]-5'yl-2-thiophenecarbonitrile was prepared according to the procedure for Example 5 using 5-bromo-2-thiophenecarbonitrile and (2'-oxo-2',3'-dihydrospiro[cyclohexane-1,3'-[3H]indol]-5'-yl) boronic acid: mp. 225–228° C.; $^1$H NMR (DMSO-$d_6$) δ 1.63 (m, 8H), 1.90 (m, 2H), 6.91 (d, 1H, J=8.13 Hz), 7.55 (dd, 1H, J=8.13, 1.76 Hz), 7.60 (d, 1H, J=4.17 Hz), 7.75 (d, 1H, J=1.76 Hz), 7.93 (d, 1H, J=4.17 Hz), 10.51 (s, 1H); MS ((+)APCI) m/z 309 [M+H]$^+$.

The title compound was prepared from 5-(2'-oxo-2',3'-dihydrospiro[cyclohexane-1,3'-[3H]indol]-5'yl-2-thiophenecarbonitrile (0.69 g) and phosphorous pentasulfide (0.4 g) in toluene (20 ml) at reflux. After 3 h. the reaction was cooled, poured into sat. aqueous sodium hydrogen carbonate solution, and extracted with EtOAc. The organic layer was separated, dried (MgSO$_4$) and evaporated. The residue was purified by column chromatography (SiO$_2$, EtOAc-hexane gradient elution) to afford the title compound (0.215 g) as an orange solid: $^1$H NMR (DMSO-$d_6$) δ 12.82 (br s, 1H), 8.00–7.98 (m, 2H), 7.74 (d, 1H, J=4.1 Hz), 7.69 (dd, 1H, J=8.2 and 1.6 Hz), 7.14 (d, 1H, J=8.1 Hz), 1.99–1.83 (m, 7H) and 1.40–1.37 (m, 3H); MS ((−)-APCI) m/z 323 [M−H]$^-$.

EXAMPLE 36

5"-(3-Fluorophenyl)spiro[cyclohexane-1,3"-[3H]indol]-2"(1"H)-thione

5'-(3-Fluorophenyl)spiro[cyclohexane-1,3'-[3H]indol]-2'(1"H)-one: Prepared according to the procedure for Example 5: mp 171–172° C.; $^1$H-NMR (CDCl$_3$) δ 8.43 (s, 1H), 7.62 (d, 1H, J=1.8 Hz), 7.42 (dt, 1H, J=6.2, 2.0 Hz), 7.39–7.37 (m, 1H), 7.33 (dt, 1H, J=5.1, 1.3 Hz), 7.26 (dq, 1H, J=5.9, 2.1 Hz), 7.05–6.99 (m, 2H), 2.03–1.64 (m, 10H); MS ((+)APCI) m/z 296 [M+H]$^+$.

The title compound was prepared from 5'-(3-fluorophenyl)spiro[cyclohexane-1,3'-[3H]indol]-2'(1'H)-one (0.70 g) and phosphorous pentasulfide (0.4 g) in toluene (20 ml) at reflux. After 3 h. the reaction was cooled, poured into sat. aqueous sodium hydrogen carbonate solution, and extracted with EtOAc, the organic layer was separated, dried (MgSO$_4$) and evaporated. The residue was purified by column chromatography (SiO$_2$, EtOAc-hexane gradient elution) to afford the product (0.42 g) as an off white solid: $^1$H NMR (DMSO-$d_6$) δ 12.75 (br s, 1H), 7.95 (d, 1H, J=1.5

Hz), 7.64 (dd, 1H, J=8.13 and 1.5 Hz), 7.53–7.48 (m, 3H), 7.21–7.14 (m, 2H), 1.99–1.83 (m, 7H) and 1.40–1.37 (m, 3H); MS ((-)-APCI) m/z 310 [M-H]⁻.

EXAMPLE 37

5-(3-Hydroxyphenyl)spiro[cyclohexane-1,3-[3H]indol]-2(1H)-thione

5'-(3-Hydroxyphenyl)spiro[cyclohexane-1,3'-[3H]indol]-2'(1'H)-one: Prepared according to the procedure for example 5: mp. 213–216° C.; $^1$H NMR (CDCl$_3$) δ 1.60–1.96 (m, 10H), 6.78–6.82 (m, 1H), 6.94 (d, 1H, J=8 Hz), 7.01–7.04 (m, 2H), 7.23 (t, 1H, J=7.7 Hz), 7.38 (d, 1H, J=8 Hz), 7.61 (s, 1H), 8.91 (s, 1H) and 9.73 (s, 1H, br); MS ((+)-APCI) m/z 294 [M+H]⁺.

The title compound was prepared from 5'-(3-hydroxyphenyl)spiro[cyclohexane-1,3'-[3H]indol]-2'(1'H)-one (100 mg) and Lawesson's reagent (110 mg) in toluene (10 ml) at reflux, according to General Procedure A, to afford the title compound (0.0045 g) as an off white solid: $^1$H NMR (CDCl$_3$) δ 9.59 (br s, 1H), 7.89 (s, 1H), 7.49 (dd, 1H, J=8.1 and 1.5 Hz), 7.33 (t, 1H, J=7.9 Hz), 7.15–7.10 (m, 3H), 6.84 (dd, 1H, J=8.0 and 2.2 Hz), 2.17–2.05 (m, 2H), 1.98–1.88 (m, 5H) and 1.57–1.53 (m, 3H): MS ((-)-APCI) m/z 308 [M-H]⁻.

EXAMPLE 38

5-(3-Chlorophenyl)-3,3-diethyl-1,3-dihydro-2H-indole-2-thione

A solution of oxindole (40 g, 0.3 mol) in dry THF (400 ml) under N$_2$ was cooled to -25° C. and treated drop wise with n-butyl lithium (2.5M in hexanes, 240 ml, 0.6 mol). To the resulting solution was added N,N,N',N'-tetramethylethylenediamine (90.4 ml, 0.6 mol). After 30 min. iodoethane (48 ml, 0.6 mol) was added and the reaction mixture was allowed to warm to room temperature and stirred over night. The reaction mixture was poured into aqueous NH$_4$Cl solution, extracted with EtOAc (2×) and the combined organic layers were washed with dil. HCl, water, brine, dried (MgSO$_4$) and concentrated. The residual oil was triturated with hexane to afford the crude product (24.5 g, 51%). A sample (3 g) was recrystallized from EtOAc/hexane to obtain 3-ethyl-indol-2-one (1.4 g), m.p. 100–101° C.; $^1$H-NMR (DMSO-d$_6$) δ 0.76 (t, 3H, J=7.5 Hz), 1.8–2.0 (m, 2H), 3.38 (t, 3H, J=5.7 Hz), 6.8 (dt, 1H, J=7.69, 0.45 Hz), 6.93 (dt, 1H, J=7.45, 1.10 Hz), 7.15 (m, 1H), 7.22 (m, 1H), 10.3 (s, 1H); MS (ESI) m/z 270 [M+H].

A solution of 3-ethyl-indol-2-one (16 g, 0.1 mol) in dry THF (200 ml) under N$_2$ was cooled to -25° C. and treated drop wise with n-butyllithium (2.5M in hexanes, 80 ml, 0.2 mol). To the resulting solution was added N,N,N',N'-tetramethylethylenediamine (30 ml, 0.2 mol). After 30 min. iodoethane (8 ml, 0.1 mol) was added and the reaction mixture was allowed to warm to RT and stirred over night. The reaction mixture was poured into an aqueous NH$_4$Cl solution, extracted with EtOAc (2×) and the combined organic layers were washed with dil. HCl, water, brine, dried (MgSO$_4$) and concentrated. The residual oil was triturated with hexane to afford 3,3-diethylindol-2-one (9 g, 45%), mp. 156–159° C.; $^1$H NMR (DMSO-d$_6$) δ 10.44 (s, 1H), 7.70–7.69 (t, 1H), 7.62–7.59 (m, 1H), 7.58 (d, 1H J=1.7 Hz), 7.53–7.50 (m, 1H), 7.45–7.41 (t, 1H), 7.36–7.35 (m, 1H), 7.34–7.33 (m, 1H), 6.91–6.89 (d, 1H J=8.2 Hz), 1.87–1.80 (m, 2H), 1.77–1.70 (m, 2H), 0.54–0.50 (t, 6H); MS (+ESI) m/z 190 (M+H).

A solution of 3,3-diethylindol-2-one (8 g, 40 mmol) and sodium acetate (4 g, 48 mmol) in acetic acid (100 ml) was treated with bromine (6.4 g, 40 mmol). After 30 min. the mixture was diluted with water and extracted with EtOAc (2×); the combined organic layers were washed with water, sat. sodium hydrogen carbonate solution, then brine, dried (MgSO$_4$) and evaporated-to afford the crude product (7.6 g, 75%). A sample was recrystallized from EtOAc/hexane to obtain 5-bromo-1,3-dihydro-3,3-diethyl-[2H]-indol-2-one, m. p. 164–165° C.; $^1$H-NMR (DMSO-d$_6$) δ 10.45 (s, 1H), 7.41–7.40 (d, 1H, J=2.2 Hz), 7.34–7.31 (m, 1H), 6.78–6.76 (d, 1H, J=8.2 Hz), 1.78–1.65 (m, 4H), 0.50–0.46 (m, 6H); MS (-ESI) m/z 266/268 (M-H).

A solution of 5-bromo-1,3-dihydro-3,3-diethyl-[2H]-indol-2-one (2.7 g, 10 mmol), 3-chlorophenylboronic acid (1.6 g, 10 mmol), potassium carbonate (4 g, 30 mmol) and tetrakis(triphenylphosphine)palladium(0) (0.5 g, 0.4 mmol) in dimethoxyethane (100 ml), ethanol (25 ml), and water (25 ml) was heated to reflux for 6 hours. After cooling to room temperature, the mixture was diluted with water and extracted with EtOAc (2×). The combined organic extracts were washed with water, then brine, dried (MgSO$_4$) and evaporated. The residue was purified by column chromatography (SiO$_2$, EtOAc:hexane 1:3) to afford 5-(3-chlorophenyl)-3,3-diethyl-1,3-dihydro-indol-2-one compound (0.8 g, 27%), tmp. 195–197° C.; $^1$H-NMR (DMSO-d$_6$) δ 7.70 (t, 1H, J=2 Hz), 7.62–7.60 (m, 1H), 7.58 (d, 1H, J=1.7 Hz), 7.52 (dd, 1H, J=8.1, 2 Hz), 7.43 (t, 1H, J=7.9 Hz), 7.36–7.33 (m, 1H), 6.90 (d, 1H, J=8.1 Hz), 1.87–1.70 (m, 4H) and 0.52 (t, 6H, J=7.4 Hz); MS (+APCI) m/z 300/302 (M-H).

The title compound was prepared from 5-(3-chlorophenyl)-3,3-diethyl-1,3-dihydro-indol-2-one compound (100 mg) and Lawesson's reagent (100 mg) in toluene (10 ml) at reflux, according to General Procedure A, to afford the product (0.023 g) as a yellow solid: $^1$H NMR (DMSO-d$_6$) δ 12.73 (br s, 1H), 7.77 (t, 1H, J=1.8 Hz), 7.75 (d, 1H, J=1.6 Hz), 7.68–7.62 (m, 2H), 7.48 (t, 1H, J=7.9 Hz), 7.40 (d, 1H, J=8.3 Hz), 7.09 (d, 1H, J=8.1 Hz), 2.07–2.00 (m, 2H), 1.86–1.79 (m, 2H) and 0.37 (t, 6H, J=7.3 Hz): MS ((-)-APCI) m/z 314/316 [M-H]⁻.

EXAMPLE 39

5-[4-Fluoro-3-(trifluoromethyl)phenyl]spiro[cyclohexane-1,3-[3H]indol]-2(1H)-thione 5-[4-Fluoro-3-(trifluoromethyl)phenyl]spiro[cyclohexane-1,3-[3H]indol]-2(1H)-one was prepared from (2'-oxo-2,3-dihydrospiro[cyclohexane-1,3'-[3H]indol]-5'-yl)boronic acid (2.5 g, 10 mmol) and 5-bromo-2-fluoro-trifluoromethylbenzene (2 g, 8 mmol) as described for Example 5, to afford the title compound (0.87 g, 30%) as a solid: mp. 222° C.; $^1$H NMR (DMSO-d$_6$) δ 1.5–1.8 (m, 8H), 1.8–2.0 (m, 2H), 6.92 (d, 1H, J=8.13 Hz), 7.51 (dd, 1H, J=8.13, 1.76 Hz), 7.55 (dd, 1H, J=10.54, 9.01 Hz), 7.72 (d, 1H, J=1.76 Hz), 7.90 (dd, 1H, J=7.03, 2.20 Hz), 7.98 (m, 1H) and 10.39 (s, 1H); MS (EI) m/z 363 (M⁺).

The title compound was prepared from 5-[4-Fluoro-3-(trifluoromethyl)phenyl]spiro[cyclohexane-1,3-[3H]indol]-2(1H)-one (90 mg) and Lawesson's reagent (90 mg) in toluene (10 ml) at reflux, according to General Procedure A, to afford the product (0.016 g) as a yellow solid: $^1$H NMR (DMSO-d$_6$) δ 12.75 (br s, 1H), 8.06–8.00 (m, 1H), 7.96–7.92 (m, 2H), 7.66–7.56 (m, 2H), 7.16 (d, 1H, J=8.1 Hz), 1.99–1.83 (m, 7H) and 1.41–1.38 (m, 3H): MS ((-)-APCI) m/z 378 [M-H]⁻.

EXAMPLE 40

4-(1,2-Dihydro-2-thioxospiro[cyclohexane-1,3-[3H]indol]-5-yl)-2-fluorobenzonitrile The title compound was prepared from 4-(1,2-dihydro-2-oxospiro[cyclohexane-1,3-[3H]indol]-5-yl)-2- fluorobenzonitrile (90 mg) and Lawesson's reagent (90 mg) in toluene (10 ml) at reflux, according to General Procedure A, to afford the title compound (0.050 g) as an orange solid: $^1$H NMR (DMSO-$d_6$) δ 12.80 (br s, 1H), 8.04 (d, 1H, J=1.3 Hz), 7.98 (t, 1H, J=7.5 Hz), 7.92 (dd, 1H, J=11.3 and 1.3 Hz), 7.76 (d, 2H, J=8.0 Hz), 7.18 (d, 1H, J=8.2 Hz), 1.99–1.82 (m, 7H) and 1.40–1.38 (m, 3H); MS ((−)-APCI) m/z 335 [M−H]$^-$.

EXAMPLE 41

5-(1,2-Dihydro-2-thioxospiro[cyclohexane-1,3-[3H]indol]-5-yl)4-n-butyl-2-thiophenecarbonitrile The title compound was prepared in a manner similar to Example 5 from 5-bromo-4-n-butyl thiophenecarbonitrile (1.24 g, 5.1 mmol), (1,2-dihydro-2-oxospiro[cyclohexane-1,3-[3H]indol)-5-boronic acid (1.24 g, 5.05 mmol), tetrakis (triphenylphosphine) palladium (0.25 g), potassium carbonate (2.75 g, 21 mmol), water (10 mL),and dimethoxyethane (50 mL) heated at reflux for 5 hours to afford 5-(1,2-dihydro-2-oxospiro[cyclohexane-1,3-[3H]indol]-5-yl) 4-n-butyl-2-thiophenecarbonitrile (1 g, 54%), mp. 130–1320 C. $^1$H NMR (DMSO-$d_6$) δ 10.56 (s, 1H), 7.92 (s, 1H), 7.52–7.51 (d, 1H, J=1.2 Hz), 7.32–7.29 (dd, 1H, J=1.5 Hz), 6.98–6.96 (d, 1H, J=8.0 Hz), 2.64–2.59 (t, 2H), 1.99–1.86 (m, 2H), 1.70–1.50 (m, 11H), 1.32–1.22 (m, 2H), 0.86–0.82 (t, 3H); MS (APCI (+)) m/z 365 [M+H]$^+$; IR (KBr) 1620, 1700, 2200 cm$^{-1}$; Anal. calc. $C_{22}H_{24}N_2OS.1/4H_2O$. C, 71.61; H, 6.69; N, 7.59. observed C, 71.13; H, 6.61; N, 6.91.

The title compound was prepared from 5-(1,2-dihydro-2-oxospiro[cyclohexane-1,3-[3H]indol]-5-yl) 4-n-butyl-2-thiophenecarbonitrile (90 mg) and Lawesson's reagent (90 mg) in toluene (10 ml) at reflux, according to General Procedure A, to afford the product (0.050 g) as an orange solid: $^1$H NMR (DMSO-$d_6$) δ 12.83 (brs, 1H), 7.95 (s, 1H), 7.77 (s, 1H), 7.44 (d, 1H, J=8.1 Hz), 7.18 (d, 1H, J=8.1 Hz), 2.63 (t, 1H, J=8.0 Hz), 1.99–1.77 (m, 7H), 1.60–1.50 (m, 2H), 1.39–1.35 (m, 3H), 1.29–1.22 (m, 2H) and 0.81 (t, 3H, J=7.3 Hz): MS ((−)-APCI) m/z 379 [M−H]$^-$.

EXAMPLE 42

5-(3-Fluoro-5-methoxyphenyl)spiro[cyclohexane-1,3-[3H]indol]-2(1H)-thione

The title compound was prepared from 5-(3-Fluoro-5-methoxyphenyl)spiro[cyclohexane-1,3-[3H]indol]-2(1H)-one (90 mg) and Lawesson's reagent (90 mg) in toluene (10 ml) at reflux, according to General Procedure A, to afford the product (0.043 g) as an off-white solid: $^1$H NMR (DMSO-$d_6$) δ 12.74 (br s, 1H), 7.90 (s, 1H), 7.63 (dd, 1H, J=8.1 and 1.2 Hz), 7.13 (d, 1H, J=8.1 Hz), 7.08 (d, 1H, J=10 Hz), 7.01 (s, 1H), 6.83 (dt, 1H, J=11 and 2.0 Hz), 1.99–1.83 (m, 7H) and 1.40–1.37 (m, 3H): MS ((−)-APCI) m/z 340 [M−H]$^-$.

EXAMPLE 43

5-(3-Chlorophenyl)-n-hydroxyspiro[cyclohexane-1,3'-[3H]indol]-2-amine

To a solution of 5'-(3-Chlorophenyl)spiro[cyclohexane-1,3'-[3H]indol]-2'(1'H)-thione (0.74 g, 2.25 mmol) in dry THF (15 ml) was added sodium hydride (60% in oil, 0.1 g, 2.5 mmol) at room temperature. After 15 min., methyl iodide (0.18 ml, 2.88 mmol) was added. After 1 h, the reaction mixture was partitioned between water and EtOAc, the organic layer was washed with brine, dried (MgSO$_4$) and evaporated to give 5-(3-chlorophenyl)-2-(methylthio)spiro[cyclohexane-1,3'-[3H]indole] (0.80 g, 100%) which was used without further purification:

To a solution of the last cited compound (1.96 g, 5.73 mmol) in DMSO (20 ml) was added hydroxylamine (60% in water, 5 ml) and the mixture was heated to 120° C. After 1 h., the reaction was cooled, partitioned between diethyl ether and saturated aqueous ammonium chloride solution. The organic layer was washed with water and brine and then dried (MgSO$_4$) and evaporated. The crude product was then crystallized from MeOH to afford the title compound (1.67 g, 5.08 mmol, 89%) as a white solid: $^1$H NMR (CDCl$_3$) δ 7.52 (t, 1H, J=1.7 Hz), 7.43–7.28 (m, 7H), 6.83 (d, 1H, J=8 Hz) and 1.98–1.51 (m, 10H); MS (ESI (+)) m/z 327/329 [M+H]$^+$.

EXAMPLE 44

N-(Acetyoxy)-5'-(3-chlorophenyl)spiro[cyclohexane-1,3'-[3H]indol]-2"-amine

To a solution of 5-(3-Chlorophenyl)-N-hydroxyspiro[cyclohexane-1,3'-[3H]indol]-2-amine (0.23 g, 0.71 mmol) in methylene chloride-methanol (9:1, 10 ml) was added acetic anhydride (0.08 ml, 0.8 mmol) and 4-dimethylaminopyridine (catalytic amount) under a nitrogen atmosphere. After 20 min., the reaction was evaporated and the product purified by column chromatography (SiO$_2$, methanol:methylene chloride 5:95). The product was then triturated with di-iso-propylether to afford the title compound (0.12 g, 0.32 mmol, 45%): $^1$H NMR (CDCl$_3$) δ 7.52–7.51 (m, 2H), 7.43–7.27 (m, 5H), 6.88 (d, 1H, J=8 Hz), 2.27 (s, 3H), 2.04–1.92 (m, 4H), 1.84–1.74 (m, 4H) and 1.72–1.57 (m, 2H); MS (ESI (+)) m/z 369/371 [M+H]$^+$; $C_{21}H_{21}ClN_2O_2.0.5 H_2O$ requires C, 66.98: H, 5.64: N, 7.34. Found C, 66.74: H, 5.86: N, 7.41.

EXAMPLE 45

5'-(3-Fluorophenyl)spiro[cyclohexane-1,3'-[3H]indol]-2'(1'H)-one Oxime

Prepared according to the method for Example 42 from 5'-(3-fluorophenyl)spiro[cyclohexane-1,3'-[3H]indole]-2' (140 H)-thione (0.59 g, 1.90 mmol) to afford the title compound (0.053 g, 0.17 mmol, 10%): $^1$H NMR (DMSO-$d_6$) δ 9.59 (s, 1H), 9.40 (s, 1H), 7.57 (d, 1H, J=1.5 Hz), 7.46–7.39 (m, 4H), 7.11–7.05 (m, 1H), 6.80 (d, 1H, J=8.1 Hz), 2.04–1.97 (m, 2H), 1.82–1.74 (m, 2H) and 1.66–1.42 (m, 6H): MS (ESI (−)) m/z 309 [M−H]$^-$, $C_{19}H_{19}FN_2O$ requires C: 73.53, H: 6.17, N: 9.03. Found C: 73.33, H: 6.07, N: 8.83.

EXAMPLE 46

5'-(2-Fluorophenyl)spiro[cyclohexane-1,3'-[3H]indol]-2'(1'H)-one Oxime

5'-bromospiro{cyclohexane-1,3'-[3H]indol}-2' (1'H)-one 2'(O-benzyloxime). 5'-Bromo-2'-(methylthio)spiro[cyclohexane-1,3'-[3H]indole] (9.0 g, 28.98 mmol) and O-benzylhydroxylamine hydrochloride (13.8 g, 86.9 mmol) were combined in methanol (150 mL) and heated to 45° C. for 6 hours. Methanol was evaporated in vacuo. Ethyl acetate was added to the residue and this mixture was washed with ammonium chloride solution. Ethyl acetate was dried over magnesium sulfate, ethyl acetate collected evaporated in vacuo and the residue was flash chromatographed on alumina 90 (9:1 Hexane/EtOAc) to the desired product (6.5 g, 60%). $^1$H NMR (DMSO-$d_6$, 300 MHz) δ 1.38–1.70 (m, 8H), 1.92–2.06 (m, 2H), 5.06 (s, 2H), 6.71 (d, 1H, J=8.26 Hz), 7.22–7.43 (m, 7H), 9.62 (s, 1H).

Procedure A

5'-(2-Fluorophenyl)-spiro[cyclohexane-1,3'-[3H]indol]-2' (1H)-one 2(O-benzyloxime). 5'-Bromospiro{cyclohexane-1,3'-[3H]indol}-2' (1'H)-one 2(O-benzyloxime) (1.0 g, 2.6 mmol), and tetrakistriphenyl phosphine Pd (0) (0.14 g, 0.12 mmol) were stirred under an atmosphere of nitrogen in ethylene glycol dimethyl ether (23 mL). After 15 minutes, 2-flurophenyl boronic acid (0.72 mg, 5.2 mmol) was added, followed by sodium carbonate (1.6 g, 15.6 mmol) in water (6.0 mL). The reaction was heated to reflux overnight, cooled to room temperature and filtered through a Celite plug. Saturated ammonium chloride was added. The water layer was extracted with ethyl acetate (3×100 mL). The combined organic layers were dried (MgSO$_4$), filtered, and the solvent removed in vacuo. The product was purified by flash silica gel chromatography; (eluant: 10:0.5 hexane:ethyl acetate) to give the desired target compound (0.75 g, 1.8 mmol, 72%) as a viscous oil. $^1$H NMR (500 MHz, DMSO-d$_6$) δ 1.44–1.73 (8H, m), 1.93–2.06 (2H, q), 5.00 (2H, s), 6.88 (1H, d, J=8.1 Hz), 7.24–7.38 (6H, m), 7.44–7.56 (5H, m), 9.64 (1H, s); MS (ESI(+ve)) m/z 399 (M–H)$^-$.

Procedure B

A solution of 5'-(2-Fluorophenyl)-spiro [cyclohexane-1,3'-[3H]indol-2'(1H)-one 2(O-benzyloxime) (0.55 g, 1.37 mmol) in ethanol(15 mL) was added to Palladium on carbon (10%, 0.11 g) in ethanol (10 mL). The mixture was stirred under an atmosphere of hydrogen (balloon) for 24 h at room temperature. The reaction mixture was filtered through a Celite plug and the filtrate was concentrated in vacuo. The product was purified by flash silica gel chromatography (hexane:ethyl acetate, gradient elutions) to give the title compound (0.45 g, 1.12 mmol, 82%), mp. 200–203° C.; $^1H$ NMR (500 MHz, DMSO-d$_6$) δ 1.45–1.73 (8H, m) 1.96–2.00 (2H, q) 6.83 (1H, d, J=7.9 Hz), 7.23–7.50 (6H, m), 9.42 (1H, s), 9.58 (1H, s); MS (ESI(+ve)) m/z 311 (M+H)$^+$.

EXAMPLE 47

5'-(4-Fluorophenyl)spiro[cyclohexane-1,3'-[3H]indol]-2'(1'H)-one Oxime

5'-(4-Fluorophenyl)-spiro[cyclohexane-1,3'-[3H]indol]-2' (1'H)-one 2'(O-benzyloxime). Prepared from 5'-bromospiro{cyclohexane-1,3'-[3H]indol}-2'(1'H)-one 2'(O-benzyloxime) (1.0 g, 2.6 mmol), and 4-fluorophenyl boronic acid (0.72 g, 5.2 mmol) according to Example 45 procedure A. The product was purified by flash silica gel chromatography; (eluant: 10:0.5 hexane:ethyl acetate) to give the desired product (0.70 g, 1.7 mmol, 67%) as a viscous oil. $^1$H NMR (500 MHz, DMSO-d$_6$) δ 1.42–1.77 (8H, m), 1.95–1.99 (2H, q), 5.00 (2H, s), 6.84 (1H, d, J=8.1 Hz), 7.21–7.63 (1H, m), 9.58 (1H, s); MS (ESI(–ve)) m/z 399 (M–H)$^-$.

The product was synthesized using 5'-(4-Fluorophenyl)-spiro[cyclohexane-1,3'-[3H]indol]-2'(1'H)-one 2'-(O-benzyloxime) (0.70 g, 1.74 mmol), according to Example 45 procedure B. The product was purified by flash silica gel chromatography; (hexane:ethyl acetate, gradient elution) to give the title compound (0.44 g, 1.4 mmol, 81%), Mp. 205–208° C.; $^1$H NMR (500 MHz, DMSO-d$_6$) δ 1.43–1.77 (8H, m), 2.00–2.05 (2H, q), 6.80 (1H, d, J=8.2 Hz), 7.21–7.24 (2H, m), 7.33–7.35 (1H, dd, J=1.9 Hz), 7.49 (1H, s), 7.60–7.63 (2H, m), 9.35 (1H, s), 9.56 (1H, s); MS (ESI(+ve)) m/z 311 (M+H)$^+$.

EXAMPLE 48

5'-(3,4-Difluorophenyl)spiro[cyclohexane-1,3'-[3H]indol]-2'(1'H)-one Oxime

5'-(3,4-Difluorophenyl)-spiro[cyclohexane-1,3'-[3H]indol]-2'(1'H)-one 2'(O-benzyloxime). Prepared from 5'-bromospiro{cyclohexane-1,3'-[3H]indol}-2' (1'H)-one 2'(O-benzyloxime) (1.0 g, 2.6 mmol) and 3,4-diflurophenyl boronic acid (1.6 g, 5.2 mmol of a 50% solution of acid in THF/water) according to Example 45 procedure A. The product was purified by flash silica gel chromatography (eluant: 10:0.5 hexane:ethyl acetate) to give the desired product (0.75 g, 1.7 mmol, 69%) as a viscous oil. $^1$H NMR (500 MHz, DMSO-d$_6$) δ 1.41–1.78 (8H, m), 1.95–1.99 (2H, q), 5.00 (2H, s), 6.82 (3H, d), 7.28–7.46 (8H, m), 7.58 (1H, q), 7.67–7.71 (1H, s ), 9.61 (1H, s); MS (ESI(–ve)) m/z 417 (M–H)$^-$.

Reaction of the last cited compound (0.70 g, 1.6 mmol) according to Example 45 procedure B, afforded the title compound (0.44 g, 1.3 mmol, 80%), $^1$H NMR (500 MHz, DMSO-d$_6$) δ 1.42–1.79 (8H, m), 2.01–2.05 (2H, q), 6.78–6.80 (1H, d), 7.39–7.46 (3H, m), 7.55 (1H, s), 7.70 (1H, m), 9.10 (1H, s), 9.59 (1H, s); MS (ESI(+ve)) m/z 329 (M+H)$^+$.

EXAMPLE 49

5'-(3-Methoxyphenyl)spiro[cyclohexane-1,3'-[3H]indol]-2'(1'H)-one Oxime

5'-(3-Methoxyphenyl)-spiro[cyclohexane-1,3'-[3H]indol]-2'(1'H)-one 2'-(O-benzyloxime). Prepared from 5'-bromospiro{cyclohexane-1,3'-[3H]indol}-2'(1'H)-one 2'(O-benzyloxime) (1.0 g, 2.6 mmol) and 3-methoxyphenyl boronic acid (0.79 g, 5.2 mmol) according to Example 45 procedure A. The product was purified by flash silica gel chromatography; (eluant: 10:0.5 hexane:ethyl acetate) to give the desired product (0.80 g, 1.9 mmol, 75%) as a viscous oil. $^1$H NMR (500 MHz, DMSO-d$_6$) δ 1.43–1.78 (8H, m), 1.95–2.00 (2H, q), 3.80 (3H, s), 5.00 (2H, s), 6.82–6.86 (2H, m), 7.10–7.16 (2H, m), 7.28–7.53 (10H, m), 9.57 (1H, s); MS (ESI(–ve)) m/z 411 (M–H)$^-$.

Reaction of the last cited compound (0.80 g, 1.9 mmol) according to Example 45 procedure B, afforded the title compound (0.48 g, 1.4 mmol, 77%), as a white solid. Mp. 101–104° C.; $^1$H NMR (500 MHz, DMSO-d$_6$) δ 1.44–1.78 (8H, m), 1.99–2.03 (2H, q), 3.81 (3H, s), 6.78 (1H, d), 6.85 (1H, d), 7.10–7.16 (2H, m), 7.30–7.38 (2H, m), 7.50 (1H, d), 9.35 (1H, s), 9.56 (1H, s); MS (ESI(+ve)) m/z 323 (M+H)$^+$.

EXAMPLE 50

5'-(3-Nitrophenyl)spiro[cyclohexane-1,3'-[3H]indol]-2'(1'H)-one Oxime

5'-(3-Nitrophenyl)-spiro[cyclohexane-1,3'-[3H]indol]-2' (1'H)-one 2'(O-benzyloxime). Prepared from 5'-bromospiro{cyclohexane-1,3'-[3H]indol}-2'(1'H)-one 2'(O-benzyloxime) (1.0 g, 2.6 mmol) and 3-Nitrophenyl boronic acid (0.86 g, 5.2 mmol) according to Example 45 procedure A. Purification by flash silica gel chromatography (eluant: 10:0.5 hexane:ethyl acetate) afforded the desired compound (0.60 g, 1.4 mmol, 55%) as a viscous oil. $^1$H NMR (500 MHz, DMSO-d$_6$) δ 1.42–1.82 (8H, m), 2.02–2.04 (2H, q), 5.01 (2H, s), 6.88 (1H, d), 7.28–7.71 (8H, m), 8.08–8.13 (2H, m), 8.38 (1H, d), 9.69 (1H, s); MS (ESI(–ve)) m/z 426 (M–H)$^-$.

Procedure C

The last cited compound (0.54 g, 1.26 mmol) was dissolved in dry methylene chloride (25 mL) and cooled to −78° C. under nitrogen. Boron tribromide (3.8 mL, 3.8 mmol, 1.0 M in methylene chloride) was added drop-wise over 5 minutes. After 30 minutes the reaction was quenched with saturated sodium bicarbonate (5 mL). The reaction mixture was allowed to warm to room temperature, the layers were separated and the aqueous layer was extracted with methylene chloride. The combined organic layers were dried ($Na_2SO_4$), filtered, and the solvent removed in vacuo. The product was purified by flash silica gel chromatography (eluant: 8:1 hexane:ethyl acetate) to give afford the title compound (0.33 g, 0.9 mmol, 78%). Mp. 221–224° C.; $^1$H NMR (500 MHz, DMSO-$d_6$) δ 1.42–1.83 (8H, m), 1.99–2.07 (2H, q), 6.84–6.85 (1H, dd), 7.50–7.52 (1H, m), 7.67–7.71 (2H, m), 8.08–8.12 (2H, m), 8.37–8.38 (1H, d), 9.48 (1H, s), 9.64 (1H, s); MS (ESI(+ve)) m/z 338 (M+H)$^+$.

EXAMPLE 51

5'-(3-Cyanophenyl)spiro[cyclohexane-1,3'-[3H]indol]-2'(1'H)-one Oxime

3-[Spiro[cyclohexane-1,3'-[3H]indol]-(1'H)-one-2'-(O-benzyloxime)]benzonitrile[3H]indol]-5-yl]benzonitrile. Prepared from 5'-bromospiro{cyclohexane-1,3'-[3H]indol}-2'(1'H)-one 2'(O-benzyloxime) (1.0 g, 2.6 mmol) and 3-cyanophenyl boronic acid (0.76 g, 5.2 mmol) according to Example 45 procedure A. The product was purified by flash silica gel chromatography (eluant: 10:0.5 hexane:ethyl acetate) to give the desired product (0.75 g, 1.8 mmol, 71%) as a viscous oil. $^1$H NMR (500 MHz, DMSO-$d_6$) δ 1.41–1.81 (8H, m), 1.96–2.03 (2H, q), 5.01 (2H, s), 6.86 (1H, d), 7.28–7.33 (9H, m), 7.95–7.97 (1H, d), 8.12 (1H, s), 9.65 (1H, s); MS (ESI(−ve)) m/z 406 (M−H)$^-$.

Reaction of the last cited compound (0.17 g, 0.43 mmol) and boron tribromide (1.2 mL, 1.2 mmol) according to Example 49 procedure C afforded the title compound (0.06 g, 0.2 mmol, 47%) as a white solid, Mp. 198–200° C.; $^1$H NMR (500 MHz, DMSO-$d_6$) δ 1.41–1.80 (8H, m), 1.97–2.04 (2H, q), 6.80 (1H, q), 7.45–7.69 (4H, m), 7.93–7.95 (1H, dd), 8.10 (1H, s), 9.42 (1H, s), 9.59 (1H, s); (ESI(+ve)) m/z 318 (M+H)$^+$.

EXAMPLE 52

3-[1',2'-Dihydro-2'-(hydroxyimino)spiro[cyclohexane-1,3'-[3H]indol]-5'yl]-5-fluorobenzonitrile To a solution of 3-fluoro-5-cyano-bromobenzene (0.4 g, 2.0 mmol) in dry DMF (10 ml) was added diboron pinacolate ester (0.63 g, 2.5 mmol), potassium acetate (0.65 g, 6.7 mmol) and $PdCl_2$ (dppf) (0.2. g) and the reaction was heated to 80° C. under a nitrogen atmosphere. After 8 h. from 5'-bromospiro{cyclohexane-1,3'-[3H]indol}-2'(1'H)-one 2'(O-benzyloxime) (0.2 g, 0.5 mmol), $PdCl_2$ (dppf) (0.05 g) and sodium carbonate (1.30 g, 12.5 mmol) were added and heating at 80° C. was continued. After 8 h. the reaction was cooled and partitioned between water and ethyl acetate, the organic layer was washed with brine, dried ($MgSO_4$) and evaporated. The residue was purified by column chromatography ($SiO_2$, EtOAc:hexane 1:20) to give the desired product (0.14 g, 0.33 mmol, 66%).

Reaction of the last cited compound (0.14 g, 0.33 mmol) and boron tribromide (1.0 ml, 1.0 mmol) according to Example 49 procedure C afforded the title compound (0.019 g, 0.05 mmol, 17%): $^1$H NMR (300 MHz, DMSO-$d_6$) δ 9.65 (s, 1H), 9.49 (s, 1H), 8.04 (m, 1H), 7.89 (dt, 1H, J 10.5 and 2 Hz), 7.72–7.68 (m, 2H), 7.54 (d, 1H, J=8.1 Hz), 6.80 (d, 1H, J=8.1 Hz), 2.05–1.99 (m, 2H), 1.84–1.76 (m, 2H) and 1.65–1.44 (m, 6H): MS (ESI(+ve)) m/z 336 (M+H)$^+$.

EXAMPLE 53

5-(Spiro[cyclohexane-1,3'-[3H]indol]-2'-(hydroxtimino)-5'-yl)-4-methyl-2-thiophenecarbonitrile 4-Methyl-5-trimethylstannanyl-thiophene-2-carbonitrile. Prepared from 5-bromo-4-methyl-thiophene-2-carbonitrile (3.08 g, 15.2 mmol), tetrakistriphenyl phosphine Pd (0) (0.82 g, 0.71 mmol), hexamethylditin (5.0 g, 15.2 mmol) and ethylene glycol dimethyl ether (20 mL) under nitrogen. The mixture was heated to reflux for 14 hours. The reaction mixture was concentrated in vacuo and purified using flash silica gel chromatography (eluant: 2% MeOH: methylene chloride) to recover the desired product (2.8 g, 0.01 mmol, 67%) as a runny oil. $^1$H NMR (300 MHz, DMSO-$d_6$) δ 0.41 (9H, s), 2.28 (3H, s), and 7.83 (1H, s).

The last cited compound (0.20 g, 0.50 mmol), dichlorobis(triphenylphosphine) palladium(II) (0.02 g, 0.03 mmol) and triphenylarsine (0.03 g, 0.13 mmol) in DME (8.0 mL) were stirred under nitrogen for 20 minutes. 5'-Bromospiro{cyclohexane-1,3'-[3H]indol}-2'(1')-one 2'-(O-benzyloxime) (0.18 g, 0.64 mmol) was added in a solution of DME (2.0 mL). The solution was heated to reflux overnight. The reaction solution was concentrated in vacuo and purified by flash silica gel chromatography (eluant 12:1 hexane:ethyl acetate) to give the crude product (0.10 g, 0.25 mmol, 50%) which was used without further purification.

Boron tribromide (2.6 mL, 2.6 mmol of a 1.0 M solution in methylene chloride) was added to a solution of the last product (0.37 g, 0.86 mmol) in dry methylene chloride (1.7 mL) at −78° C. The solution was stirred for 30 minutes and quenched with saturated sodium bicarbonate (10 mL). The mixture was allowed to warm to room temperature and the layers were separated. The organic layer was dried ($Na_2SO_4$), filtered and concentrated in vacuo to give crude product which was purified by flash silica gel chromatography (eluant: 6:1 hexane:ethyl acetate) to give the title compound (0.02 g, 24%): Mp. 173–176° C.; $^1$H NMR (500 MHz, DMSO-$d_6$) δ 1.44–1.73 (8H, m), 1.96–2.00 (2H, m), 2.28 (3H, s), 6.82–6.84 (1H, m), 7.24–7.26 (1H, dd, J=1.7 Hz), 7.38 (1H, m), 7.82 (1H, m), 9.51 (1H, m), 9.66 (1H, m); MS (ESI(+ve)) m/z 338 (M+H)$^+$.

EXAMPLE 54

5-(Spiro[cyclohexane-1,3'-[3H]indol]-2'(hydroxyimino)-5'-yl)-2-thiophenecarbonitrile To a solution of 2-cyanothiophene (1.0 g, 9.16 mmol) and tri-iso-propylborate (2.3 ml, 10 mmol) in dry THF (30 ml) under nitrogen at −78° C. was added, dropwise, lithium hexamethyldisilazide (1M in THF, 10 ml, 10 mmol). After 30 min., the reaction was quenched with 1N HCl, then extracted with ethyl acetate, the organic layer was washed with water, dried ($Na_2SO_4$) and evaporated to the product (1.25 g, 8.17 mmol, 89%) which was used without further purification: $^1$H NMR (500 MHz, DMSO-$d_6$) δ 8.75 (br s, 2H), 7.97 (d, 1H, J=8 Hz) and 7.73 (d, 1H, J=8 Hz): MS (ESI(−ve)) m/z 152 (M−H)$^-$.

Prepared from the last cited product (0.91 g, 5.95 mmol) and 5'-bromospiro{cyclohexane-1,3'-[3H]indol}-2'(1'H)-one 2'(O-benzyloxime) (1.53 g, 3.97 mmol) according to Example 45 procedure A. Purification by flash silica gel chromatography (eluant: 5:1 hexane:THF) gave the desired product (0.66 g, 1.59 mmol) which was used without further purification: MS (ESI(–ve)) m/z 412 (M–H)⁻.

Reaction of the last cited compound (0.60 g, 1.45 mmol) and boron tribromide (1M in dichloromethane, 5 mL, 5 mmol) according to Example 49 procedure C afforded the title compound (0.036 g, 0.11 mmol, 8%): $^1$H NMR (300 MHz, DMSO-$d_6$) δ 9.71 (s, 1H), 9.62 (s, 1H), 7.92 (d, 1H, J=3.9 Hz), 7.63 (d, 1H, J=1.5 Hz), 7.54 (d, 1H, J=3.9 Hz), 7.47 (dd, 1H, J=8.1 and 1.6 Hz), 6.78 (d, 1H, J=8.1 Hz), 2.13–1.90 (m, 2H) and 1.78–1.60 (m, 6H): MS (ESI(+ve)) m/z 324 (M+H)⁺.

EXAMPLE 55

4-(Spiro[cyclohexane-1,3'-[3H]indol]-2' (hydroxyimino)-5 '-yl)-2-thiophenecarbonitrile 4-(Trimethylsilyl)-2-thiophenecarbonitrile. A solution of 3-bromo-2-thiophenecarbonitrile (0.8 g, 4.3 mmol), tetrakis (triphenylphosphine)palladium(0) (0.25 g, 0.2 mmol) and hexamethylditin (1.4 g, 4.3 mmol) in dimethoxyethane (5 cm³) was heated under reflux for 14 h then cooled to RT. The reaction mixture was absorbed onto florisil and purified by column chromatography ($SiO_2$, methylene chloride:hexane 1:9) to afford the subtitled compound (1.04 g, 3.8 mmol, 90%) as a clear viscous oil: $^1$H NMR ($CDCl_3$) δ 0.35 (s, 9H), 7.56 (d, J=0.9 Hz, 1H), 7.66 (d, J=0.9 Hz, 1H).

To a solution of 5'-bromospiro{cyclohexane-1,3'-[3H] indol}-2'(1'H)-one 2'(O-benzyloxime) (1.65 g, 4.28 mmol), 4-(trimethylstannyl)-2-thiophenecarbonitrile (1.48 g, 5.44 mmol), triphenylarsine (330 mg) in dry dimethoxy ethane (20 ml), under a nitrogen atmosphere was added bis (triphenylphosphine)palladium (II) chloride, and the mixture was heated under reflux for 16 h. After cooling to room temperature the mixture was evaporated, and the residue purified by column chromatography ($SiO_2$, EtOAc:hexane, gradient elution) to afford the desired product (0.61 g, 1.47 mmol, 56%).

Reaction of the last cited compound (0.61 g, 1.47 mmol) and boron tribromide (1M in dichloromethane, 4.5 mL, 4.5 mmol) according to Example 49 procedure C afforded the title compound (0.084 g, 0.26 mmol, 18%): $^1$H NMR (300 MHz, DMSO-$d_6$) δ 9.61 (s, 1H), 9.42 (s, 1H), 8.41 (s, 1H), 8.18 (s, 1H), 7.65 (s, 1H), 7.48 (dd, 1H, J=8.1 and 0.9 Hz), 6.76 (d, 1H, J=8.1 Hz), 2.03–1.96 (m, 2H) and 1.78–1.42 (m, 6H): MS (ESI(+ve)) m/z 324 (M+H)⁺.

EXAMPLE 56

5-(Spiro[cyclohexane-1,3'-[3H]indol]-2'- (hydroxyimino)-5'-yl)-1H-pyrrole-1-methyl-2- carbonitrile 2-{5'[spiro[cyclohexane-1,3'-[3H]indol]-(1'H)-one-2'(O-benzyloxime)]}-1H-pyrrole-1-carboxylic acid, tert-butyl ester. A solution of 5'-bromospiro{cyclohexane-1,3'-[3H] indol}-2' (1'H)-one 2'(O-benzyloxime) (7.4 g, 19.17 mmol) and tetrakis (triphenylphosphine)palladium (0) (2.5 g, 2.00 mmol) in DME (100 ml) was stirred under nitrogen for 15 minutes. To the solution was added 1-tert-butoxycarbonylpyrrole boronic acid (5.5 g, 26 mmol) and 1M sodium carbonate (50 ml). The mixture was heated to 80° C. for 6 hours and allowed to cool. The reaction mixture was poured into water and extracted with ethyl acetate (3×100 ml). The organic layers were combined and dried over magnesium sulfate. The solution was filtered, concentrated in vacuo, and the residue was purified by flash chromatography on silica gel (4.5:1 Hexane/ethylacetate) to give the product (7.7 g, 88%) as a white solid. $^1$H NMR (DMSO-$d_6$, 300 MHz) δ 1.28 (s, 9H), 1.55–1.66 (m, 8H), 1.83–1.98 (m, 2H), 4.99 (s, 2H), 6.12–6.14 (m, 1H), 6.22 (t, 1H, J=3.26 Hz), 6.76 (d, 1H, J=7.9 Hz), 7.02 (dd, 1H, J=7.98, 1.4 Hz), 7.19 (s, 1H) 7.27–7.31 (m, 2H), 7.35 (t, 1H, J=6.8 Hz), 7.43 (d, 1H, J=8 Hz), 9.55 (s, 1H).

5'-(1-tert-Butoxycarbonyl-1H-pyrrol-2-yl)spiro [cyclohexane-1,3'-[3H]indol]-2'-(1'H)one-2'-(O-benzyloximne)-1'-carboxylic acid, tert-butyl ester. To a solution of 2-{5'[spiro[cyclohexane-1,3'-[3H]indol]-(1'H)-one-2'-(O-benzyloxime)]}-1H-pyrrole-1-carboxylic acid, tert-butyl ester (7.7 g, 16.38 mmol) in THF (anhydrous, 100 mL) was added sodium hydride (0.665 g, 17 mmol) after hydrogen evolution ceased di-tert-butyldicarbonate (10.9 g, 50 mmol) and DMAP(0.20 g) was added and the reaction stirred at 65° C. for 18 hours. The reaction mixture was poured into water and extracted with ethyl acetate. The organic layers were combined, and dried over magnesium sulfate. The solution was filtered, concentrated in vacuo, to give the product (9.0 g, 15.76 mmol) which was taken directly to the next step.

To a solution of 5'-(1-tert-Butoxycarbonyl-1H-pyrrol-2-yl)spiro[cyclohexane-1,3'-[3H]indol]-2'-(1'H)one-2'-(O-benzyloxirne)-1'-carboxylic acid, tert-butyl ester (9.0 g, 15.76 mmol) in THF (anhydrous, 75 mL) at –78° C. was added chlorosulfonyl isocyanate (1.55 mL, 17.54 mmol). After 90 minutes, DMF (21 mL, 275 mmol) was added and the reaction was allowed to warm to room temperature. The reaction was poured into water (200 mL) and extracted with ethyl acetate (2×100 mL). The organic layers combined and dried over magnesium sulfate, filtered and concentrated in vacuo. Purification by flash column chromatography on silica gel (10% ethyl acetate/ Hexane) gave 5'-(5-cyano-1-tert-butoxycarbonyl-1H-pyrrol-2-yl)spiro[cyclohexane-1,3'-[3H]indol]-2'(1'H)one-2'(O-benzyloxime)-1'-carboxylic acid, tert-butyl ester (7.6 g, 82%) as a white powder. $^1$H NMR (DMSO-$d_6$, 300 MHz) δ 1.30 (s, 9H), 1.38 (s, 9H), 1.58–1.83 (m, 8H), 1.72–1.73 (m, 2H), 5.0 (s, 2H), 6.44–6.45 (d, 1H, J=3.76 Hz), 7.25–1.46 (m, 10H).

5'-(5-Cyano-1H-pyrrol-2-yl)spiro[cyclohexane-1,3'-[3H] indol]-2'(1'H)one-2'-(O-benzyloxime)-1'-carboxylic acid, tert-butyl ester. To a solution of 5'-(5-cyano-1-tert-butoxycarbonyl-1H-pyrrol-2-yl)spiro[cyclohexane-1,3'-[3H]indol]-2'(1'H)one-2'(O-benzyloxime)-1'-carboxylic acid, tert-butyl ester (7.6 g, 3.25 g, 48 mmol) in THF (anhydrous, 30 mL) was added a solution of sodium ethoxide in ethanol (120 mL). The reaction mixture was heated to 80° C. and stirred overnight. The mixture was cooled to room temperature and concentrated in vacuo. The residue was dissolved in ethyl acetate and washed with water, brine, and dried over magnesium sulfate. The solvent was evaporated in vacuo to afford the product (6.1 g, 95%). $^1$H NMR (DMSO, 500 MHz) δ 1.38 (s, 9H), 1.63–1.74 (m, 8H), 1.88–1.97 (m, 2H), 5.08 (s, 2H) 6.69–6.7 (d, 1H, J=0.8 Hz), 6.98–6.99 (d, 1H, J=0.7 Hz), 7.29–7.37 (m, 1H), 7.35 (m, 2H), 7.42 (m, 3H), 7.63 (dd, 1H, J=1.8, 0.3 Hz), 7.76 (d, 1H, J=0.4 Hz).

5'-(5-Cyano-1-methyl-1H-pyrrol-2-yl)spiro[cyclohexane-1,3'-[3H]indol]-2'-(O-benzyloxime)-1'-carboxylic acid, tert-butyl ester. To 5'-(5-cyano-1H-pyrrol-2-yl)spiro [cylohexane-1,3'-[3H]indol]-2'(1'H)one-2'-(O-benzyloxime)-1'-carboxylic acid, tert-butyl ester (6.1 g, 12.29 mmol) in DMF (75 mL) was added potassium carbonate (6.5 g, 47 mmol) and MeI (1 mL, 15.4 mmol) and the reaction mixture was stirred at room temperature for 2.5 hours. The reaction mixture was poured into water and extracted with ethyl acetate. The organic layer was washed with brine and the solvent was concentrated in vacuo. To give the desired product (6.1 g, 12.29 mmol) which was carried on to the next step without further purification. $^1$H NMR (DMSO, 300 MHz) δ 1.38 (s, 9H), 1.62–1.98 (m, 10H), 3.71 (s, 3H), 5.08 (s, 2H), 6.34 (d, 1H, J=4.1 Hz), 7.03 (d, 1H, J=3.99 Hz), 7.30–7.53 (m, 8H).

5-{5'-Spiro[cyclohexane-1,3'-[3H]indol]-(1'H)-one-2'-(O-benzyloxime)}-1H-pyrrole-1-methyl-2-carbonitrile. 5'-(5-Cyano-1-methyl-1H-pyrrol-2-yl)spiro[cyclohexane-1,3'-[3H]indol]-2'-(O-benzyloxime)-1'-carboxylic acid, tert-butyl ester (6.1 g, 12.29 mmol) was dissolved in dioxane (5 mL) and 4 M HCl in dioxane (10 mL) was added and the reaction heated to 45° C. for 3.5 hours. The mixture was carefully neutralized with sodium bicarbonate (sat.). The reaction mixture was poured into water and extracted with ethyl acetate. The organic layer was washed with brine and dried over magnesium sulfate. The solvent was evaporated in vacuo. Purification by column chromatography on silica gel (5% ethyl acetate/hexane) gave the product (4.36 g, 94%). $^1$H NMR (DMSO-$d_6$, 300 MHz) δ 1.57–1.7 (m, 8H), 1.9–2.05 (m, 2H), 3.68 (s, 3H), 5.00 (s, 2H), 6.25 (d, 1H, J=3.92 Hz), 6.85 (d, 1H, J=8.03 Hz), 7.00 (d, 1H, J=4.08 Hz), 7.2–7.44 (m, 7H), 9.7 (s, 1H).

To 5-{5'-spiro[cyclohexane-1,3'-[3H]indol]-(1'H)-one-2'-(O-benzyloxime)}-1H-pyrrole-1-methyl-2-carbonitrile (4.36 g, 10.6 mmol) in methylene chloride (50 mL) was added 1M boron tribromide (35 mL, in methylene chloride) at −78° C. The reaction mixture was allowed to warm to room temperature. After 4 hours, the reaction mixture was quenched with saturated sodium bicarbonate (100 mL). The organic layer was collected and the aqueous layer was extracted with ethyl acetate (2×100 mL), organic layers combined, washed with brine, dried over magnesium sulfate, and the solvent evaporated in vacuo. The residue was purified by flashed chromatography on silica gel (7:3 hexane/ethylacetate) to give the title compound (1.35 g, 40%) as a white solid. $^1$H NMR (DMSO-$d_6$, 300 MHz) δ 1.58–1.71 (m, 8H), 1.99–2.00 (m, 2H), 3.69 (s, 3H) 6.24 (d, 1H, J=4.07 Hz), 6.8 (d, 1H, J=8.05 Hz), 6.99 (d, 1H, J=4.01 Hz), 7.20 (dd, 1H, J=8.04, 1.57 Hz), 7.36 (d, 1H, J=1.12 Hz), 9.48 (s, 1H), 9.62 (s, 1H).

EXAMPLE 57

5-(Spiro[cyclohexane-1,3'-[3H]indol]-2'-(hydroxyimino)-5'-yl)-1H-pyrrole-2-carbonitrile 5-(spiro[cyclohexane-1,3'-[3]indole]-2'(1H)-(O-benzyloxime))-1H-pyrrole-2-carbonitrile. Prepared from 5'-(5-Cyano-1H-pyrrol-2-yl)spiro[cyclohexane-1,3'-[3H]indol]-2'(1'H)one-2'-(O-benzyloxime)-1'-carboxylic acid, tert-butyl ester (0.395 g, 0.796 mmol) dissolved in 2 mL of THF and 4M HCl Dioxane/water (10 mL) following the procedure used to prepare 5-{5'-spiro[cyclohexane-1,3'-[3H]indol]-(1'H)-one-2'-(O-benyloxime)}-1H-pyrrole-1-methyl-2-carbonitrile the desired product was obtained (0.220 g, 0.745 mmol, 95%). $^1$H NMR (DMSO-$d_6$, 500 MHz) δ 1.44–1.50 (m, 1H), 1.61–1.70 (m, 7H), 1.94–1.99 (m, 2H), 5.0 (s, 2H), 6.55 (d, 1H, J=4 Hz), 6.79 (d, 1H, J=8.0 Hz), 6.95 (d, 1H, J=4 Hz), 7.27–7.31 (m, 1H), 7.34–7.37 (m, 2H), 7.42–7.43 (m, 2H), 7.47 (dd, 1H, J=8.0, 1.4 Hz), 7.65 (d, 1H, J=1.5 Hz), 9.65 (s, 1H), 12.4 (s, 1H).

The title compound was prepared from 5-(spiro[cyclohexane-1,3'-[3]indole]-2'(1H)-(O-benyloxime))-1H-pyrrole-2-carbonitrile (0.325 g, 0.82 mmol) and 1M Boron tribromide (6 mL in methylene chloride), following the procedure for 5-(spiro[cyclohexane-1,3'-[3H]indole]-2'-(hydroxyimino)-5'-yl)-1H-pyrrole-1-methyl-2-carbonitrile, to obtain the product as an off white solid (0.110 g, 0.326 mmol, 44%). $^1$H-NMR (DMSO-$d_6$, 500 MHz) δ 1.46–1.5 (m, 1H), 1.62–1.71 (m, 7H), 1.95–2.05 (m, 2H), 6.55 (d, 1H, J=4.0 Hz), 6.75 (d, 1H, J=8.0 Hz), 6.94 (d, 1H, J=3.47 Hz), 7.45 (dd, 1H, J=8.1, 1.73 Hz), 7.63 (d, 1H, J=1.73 Hz), 9.42 (s, 1H), 9.59 (s, 1H), 12.39 (s, 1H).

EXAMPLE 58

4-(Spiro[cyclohexane-1,3'-[3H]indole]-2'(acetoxyimino)-5'-yl)-2-thiophenecarbonitrile To a solution of 4-(Spiro[cyclohexane-1,3'-[3H]indole]-2'(hydroxyimino)-5'-yl)-2-thiophenecarbonitrile (2.21 g, 6.83 mmol) and acetic anhydride (1 ml) in dichloromethane-pyridine (30 ml, 9:1) was added 4-dimethylaminopyridine (250 mg) at room temperature. After 3 h., the mixture was diluted with dichloromethane, washed with water, dil. Hydrochloric acid, water, dried (MgSO$_4$), and evaporated. The residue was purified by column chromatography (EtOAc: hexane, gradient elution) to afford the title compound (0.84 g, 2.29 mmol, 33%) as a white solid: MS (ESI (+ve)) m/z 366 [M+H]$^+$.

EXAMPLE 59

3-Fluoro-N'-hydroxy-5-[2'-(hydroxyamino)spiro[cyclohexane-1,3'-[3H]indol]-5'-yl]benzenecarboximidamide 5'-(3-Cyano-5-fluorophenyl)-2-(methylthio)spiro[cyclohexane-1,3'-[3H]indole]. Prepared from 3-(1,2-Dihydro-2-thioxospiro[cyclohexane-1,3'-[3H]indol]-5'-yl)-5-fluorobenzonitrile (0.451 g, 1.34 mmol) according to the procedure described in Example 42 to afford the desired product (0.316 g, 0.90 mmol, 67%): $^1$H NMR (DMSO, 300 MHz) δ 7.74 (d, 1H, J=1.7 Hz), 7.68 (t, 1H, J=1.4 Hz), 7.58 (d, 1H, J=8.0 Hz), 7.54 (t, 1H, J=2.3 Hz), 7.50 (dd, 1H, J=8.0 and 1.9 Hz), 7.33–7.29 (m, 1H), 2.67 (s, 3H), 2.04–1.78 (m, 7H) and 1.58–1.50 (m, 3H); MS (ESI(+ve)) m/z 351 (M+H)$^+$.

To a solution of the last cited product (0.30 g, 0.88 mmol) in DMSO (10 ml) was added hydroxylamine (50% aqueous solution, 1 ml), and the reaction was heated to 120° C. After 1 h., the mixture was cooled, partitioned between saturated aqueous ammonium chloride and ethylacetate. The organic layer was washed with water, brine, dried (MgSO$_4$), and evaporated. The residue was purified by column chromatography (SiO$_2$, 5% MeOH in dichloromethane) to afford the title compound (0.079 g, 0.23 mmol, 26%) as a white foam: $^1$H NMR (DMSO, 300 MHz) δ 9.79 (s, 1H), 9.61 (s, 1H), 9.42 (s, 1H), 7.73 (s, 1H), 7.61 (d, 1H, J=1.3 Hz), 7.46 (dd, 1H, J=8.3 and 1.5 Hz), 7.34 (d, 1H, J=10 Hz), 6.81 (d, 1H, J=8.0 Hz), 6.01 (s, 2H), 2.11–2.02 (m, 2H) and 1.81–1.56 (m, 8H): MS (ESI(+ve)) m/z 369 (M+H)$^+$.

EXAMPLE 60

N'-Hydroxy-5-(spiro[cyclohexane-1,3'-[3H]indol]-2'(hydroxtimino)-5'-yl)-4-methyl-2-thiophenecarboximidamide 4-Methyl-5-(spiro[cyclohexane-1,3'-[3H]indol]2'-(methylthio)-5'-yl)-2-thiophenecarbonitrile. To potassium tert-butoxide (0.32 g, 2.6 mmol) in THF was added 5-(1', 2'-Dihydro-2'-thioxospiro[cyclohexane-1,3'-[3H]indol]-5'-yl)-4-methyl-2-thiophenecarbonitrile (0.84 g, 2.5 mmol). After 15 minutes, methyl iodide (0.50 g, 3.48 mmol) was added. After 3 hours, reaction was poured into ammonium chloride (sat.) and extracted with ethylacetate. The organic layers were combined and dried over magnesium sulfate. The solution was filtered, concentrated in vacuo, and the residue was purified by flash chromatography on silica gel (4:1 Hexane/ethyl acetate) to give the desired product (0.530 g, 85%). (DMSO, 300 MHz) δ 1.48 (m, 3H), 1.70 (m, 2H), 1.81 (m, 5H), 2.32 (s, 3H), 2.62 (s, 3H), 7.48 (dd, 1H, J=7.87 Hz, 1.46 Hz), 7.5 (d, 1H, J=8.05 Hz), 7.77 (d, 1H, J=1.46 Hz), 7.88 (s, 1H).

To 4-methyl-5-(spiro[cyclohexane-1,3'[3H]indol]2'-(methylthio)-5'-yl)-2-thiophenecarbonitrile (0.450 g, 1.3 mmol) in DMSO (1 mL) was added hydroxylamine hydrochloride (2 mL, 50% sol. in water) and heated to 100° C. for 2.5 hours. Water was added until solution became slightly turbid, allowed the mixture to cool to room temperature. The white solid was filtered, collected and dissolved in ethyl acetate and dried over magnesium sulfate. The solution was filtered, concentrated in vacuo, giving (0.320 g, 69%). (DMSO-$d_6$, 500 MHz) δ 1.4–1.74 (m, 8H), 1.94–2.4 (m, 2H), 2.54 (s, 3H), 5.8 (s, 1H), 6.79 (d, 1H, J=8.0 Hz), 7.16(dd, 1H, J=8.12, 1.83 Hz), 7.39 (m, 2H), 9.42 (s, 1H), 9.56 (s, 1H), 9.58 (s, 1H).

EXAMPLE 61

N'-Hydroxy-4-(spiro[cyclohexane-1,3'-[3H]indol]-2' (hydroxyimino)-5'-yl-2-thiophenecarboximidamide 4-(Spiro[cyclohexane-1,3'-[3H]indol]-2'-(methylthio)-5'-yl]-2-thiophenecarbonitrile (0.077 g, 237 mmol) was reacted with 50% solution of hydroxylamine (1 mL) following the procedure for Example 59 to afford the title compound (0.016 g, 0.044 mmol, 20%). MS (ESI, (+ve)) m/z 357 [M+H]$^+$.

EXAMPLE 62

N'-Hydroxy-5-(spiro[cyclohexane-1,3'-[3H]indol]-2'-(hydroxyimino)-5'-yl)-2-thiophenecarboximidamide The title compound was prepared from 5-(spiro[cyclohexane-1,3'-[3H]indol]2'-(methylthio)-5'-yl]-2-thiophenecarbonitrile (0.500 g, 1.5 mmol) and a 50% solution of hydroxylamine (2 mL, excess) following the procedure for Example 59, to afford the product (0.200 g, 0.56 mmol, 56%). $^1$H NMR (DMSO-$d_6$, 500 MHz) δ 1.45–1.75 (m, 8H), 1.97–2.06 (m, 2H), 5.89 (s, 1H), 6.74 (d, 1H, J=8 Hz), 7.3 (d, 1H, J=3.9 Hz), 7.34 (dd, 1H, J=8.06, 1.46 Hz), 7.4 (d, 1H, J=8.0 Hz), 7.5 (d, 1H, J=1.95 Hz), 9.44 (s, 1H), 9.58 (s, 1H), 9.6 (s, 1H).

EXAMPLE 63

5'-(3-Chlorophenyl)spiro[cyclohexane-1,3'-[3H] indol]-2'-cynamide

5'-(3-Chlorophenyl)spiro[cyclohexane-1,3'-[3H]indol]-2'-amine. To a turbid solution of 5'-(3-Chlorophenyl)-N-hydroxyspiro[cyclohexane-1,3-[3H]indol]-2-amine (0.500 g; 1.53 mmol) in 25 mL of ethanol was added hydrazine hydrate (0.600 mL; 12.24 mmol). The solution was warmed to 55° C., where Raney-nickel (50% in water) was added to the reaction to keep a constant evolution of gas. After 45 minutes, the hot reaction mixture was filtered through a Celite plug and rinsed with a copious amount of hot methanol. The filtrate was concentrated in vacuo to give 0.890 g of an opaque solid. The product was purified by flash silica gel chromatography; (eluant, 2% to 8% methanol-methylene chloride with 0.1% ammonium hydroxide) to afford 0.310 g (65%) of the desired product as a white solid. Mp. 118–120° C. $^1$H NMR δ (300 MHz, DMSO-$d_6$) 1.31–1.46 (m, 2H), 1.70–1.93 (m, 8H), 7.0 (d, 1H), 7.1 (br, 2H, 2NH), 7.31–7.34 (dt, 1H, J=8 Hz), 7.41–7.46 (t, 2H), 7.55–7.58 (d, 1H), 7.62 (s, 1H), 7.72 (s, 1H); MS (ECI(+ve)) m/z 311 (M+H)$^+$.

1-tert-butoxycarbonyl-5'-(3-chlorophenyl)spiro [cyclohexane-1,3'-[3H]indol]-2'-amine. To a solution of 5'-(3-chlorophenyl)spiro[cyclohexane-1,3-[3H]indol]-2'-amine (0.310 g; 0.96 mmol) in dry methylene chloride at 0° C. was added Di-tert-butyl dicarbonate (0.252 g; 1.15 mmol) and 4-dimethylaminopyridine (0.117 g; 0.96 mmol). The solution was allowed to warm to room temperature and stir 24 h. The reaction solution was diluted with water(50 mL) and the layers were separated. The organic layer was dried over Na$_2$SO$_4$, filtered and concentrated in vacuo to give 0.355 g of a yellow oil. The product was purified by flash silica gel chromatography; (eluant, 1% to 3% methanol-methylene chloride) to afford the desired product (0.081 g, 20%) as a white solid. $^1$H NMR (300 MHz, DMSO-$d_6$) δ 1.58 (m, 2H), 1.63 (s, 9H, Boc), 1.77–1.79 (m, 8H), 7.42–7.48 (m, 2H), 7.64–7.68 (m, 3H), 7.70–7.80 (m, 2H), 9.72 (s, 1H, NH). MS (ECI(+ve)) m/z 411 (M+H)$^+$.

1'-tert-Butoxycarbonyl-5'-(3-chlorophenyl)spiro [cyclohexane-1,3'-[3H]indol]-2'-amine (0.120 g; 0.29 mmol) in 2.0 mL of dry DMF was added to a solution of 4-dimethylaminopyridine (0.089 g; 0.73 mmol) and cyanogen bromide (0.077 g; 0.73 mmol) in 4.0 mL of dry DMF at 0° C. The yellow solution was heated to 40° C. for 16 h. Work-up included pouring the reaction solution into 0.1 N NaHCO$_3$ (50 mL) and extracting with ethyl acetate (3×50 mL). The combined organic layers were dried over anhydrous Na$_2$SO$_4$, filtered and concentrated in vacuo to give 0.091 g of a yellow residue. The product was purified by flash silica gel chromatography; (stepwise gradient of 5:1 to 3:1 hexane:ethyl acetate) to afford 0.031 g (32%) of the product as a bright yellow solid. Mp. 225° C. (dec.). $^1$H NMR (500 MHz, DMSO-$d_6$) δ 1.46–1.73 (m, 8H), 1.89–1.90 (m, 2H), 7.13–7.16 (d, 1H), 7.38–7.41 (dt, 1H, J=8 Hz), 7.45–7.50 (m, 1H), 7.60–7.63 (dd, 2H, J=6.4 Hz), 7.71 (s, 1H), 7.85 (s, 1H), 12.1 (s, 1H, NH); MS (ECI(−ve)) m/z 336 (M−H)$^−$.

Other desirable compounds, which can be made according to the methods described herein, include 5'-(3-Cyano-5-fluorophenyl)spiro[cyclohexane-1,3'-[3H]indol]-2'-ylidenecyanamide, 5'-(5-Cyano-1H-pyrrol-2-yl)spiro [cyclohexane-1,3'-[3H]indol]-2-ylidenecyanamide, 5'-(5-Cyano-1-methyl-1H-pyrrol-2-yl)spiro[cyclohexane-1,3'-[3H]indol]-2'-ylidenecyanamide, 5'-(5-Cyanothien-2-yl) spiro[cyclohexane-1,3'-[3H]indole]-2'-ylidenecyanamide, 5'-(5-Cyano-3-methyl-thien-2-yl)spiro[cyclohexane-1,3'-[3H]indol]-2'-ylidenecyanamide, 5'-(5-Cyano-thien-3-yl) spiro[cyclohexane-1,3'-[3H]indol]-2'-ylidenecyanamide, 3-(spiro[cyclohexane-1,3'-[3H]indole]-2'-(cyanomethylene)-5'-yl)-5-fluorobenzonitrile, 5-(spiro [cyclohexane-1,3'-[3H]indole]-2'-(Cyanomethylene)-5'-yl)-1-methyl-1H-pyrrole-2-carbonitrile, 5-(spiro[cyclohexane-1,3'-[3H]indole]-2'-(Cyanomethylene)-5'-yl)-thiophene-2-carbonitrile, 5-(spiro[cyclohexane-1,3'-[3H]indole]-2'-(Cyanomethylene)-5'-yl)-4-methyl-thiophene-2-carbonitrile, and 4-(spiro[cyclohexane-1,3'-[3H]indole]-2'-(Cyanomethylene)-5'-yl)-thiophene-2-carbonitrile.

All publications cited in this specification are incorporated herein by reference herein. While the invention has been described with reference to a particularly preferred embodiment, it will be appreciated that modifications can be made without departing from the spirit of the invention.

Such modifications are intended to fall within the scope of the appended claims.

What is claimed:

1. A compound of formula 1:

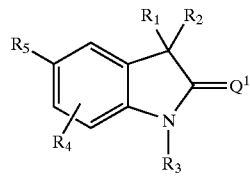

wherein:
R₁ and R₂ are independently selected from the group consisting of H, alkyl, substituted alkyl, OH, O(alkyl), O(substituted alkyl), OAc, aryl, substituted aryl, heteroaryl), substituted heteroaryl, alkylaryl, alkylheteroaryl), 1-propynyl, and 3-propynyl;
or R₁ and R₂ together form a double bond to one of the following: CMe₂, C(cycloalkyl), O, or C(cycloether);
R₃ is selected from the group consisting of H, OH, NH₂, $C_1$ to $C_6$ alkyl, substituted $C_1$ to $C_6$ alkyl, $C_3$ to $C_6$ alkenyl, alkynyl, substituted alkynyl, and $COR^A$;
$R^A$ is selected from the group consisting of H, $C_1$ to $C_3$ alkyl substituted $C_1$ to $C_3$ alkyl, $C_1$ to $C_3$ alkoxy, substituted $C_1$ to $C_3$ alkoxy, $C_1$ to $C_3$ aminoalkyl, and substituted $C_1$ to $C_3$ aminoalkyl;
R₄ is selected from the group consisting of Hi halogen, CN, NH₂, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, and substituted $C_1$ to $C_6$ aminoalkyl;
R₅ is selected from the group consisting of a), b) and c):
a) a substituted benzene ring containing the substituents X, Y and Z as shown below:

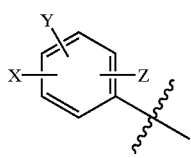

X is selected from the group consisting of H, halogen, OH, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, S(O)alkyl, S(O)₂alkyl, $C_1$ to $C_3$ aminoalkyl, substituted $C_1$ to $C_3$ aminoalkyl, NO₂, $C_1$ to $C_3$ perfluoroalkyl, 5 or 6 membered heterocyclic ring consisting of 1 to 3 heteroatoms, CONH₂, CSNH₂, CONHalkyl, CSNHalkyl, CON(alkyl)₂, CSN(alkyl)₂, $COR^B$, $OCOR^B$, and $NR^C COR^B$;
$R^B$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;
$R^C$ is H, $C_1$ to $C_3$ alkyl, or substituted $C_1$ to $C_3$ alkyl;
Y and Z are independently selected from the group consisting of H, halogen, CN, NO₂, $C_1$ to $C_3$ alkoxy, $C_1$ to $C_3$ alkyl, and $C_1$ to $C_3$ thioalkyl;
b) R₅ is a five or six membered heterocyclic ring consisting of 1, 2, or 3 heteroatoms selected from the group consisting of O, S, SO, SO₂ and NR⁶ and containing one or two independent substituents selected from the group consisting of H, halogen, CN, NO₂, $C_1$ to $C_4$ alkyl, $C_1$ to $C_3$ alkoxy, $C_1$ to $C_3$ aminoalkyl, $COR^D$, and $NR^E COR^D$;
wherein:
$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^E$ is H, $C_1$ to $C_3$ alkyl, or substituted $C_1$ to $C_3$ alkyl;
R⁶ is H or $C_1$ to $C_3$ alkyl; and
c) R₅ is an indol-4-yl, indol-7-yl or benzo-2-thiophene moiety, the moiety being optionally substituted by from 1 to 3 substituents selected from the group consisting of halogen, lower alkyl, CN, NO₂, lower alkoxy, and CF₃;
$Q^1$ is NR₇;
R₇ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, acyl, substituted acyl, aroyl, substituted aroyl, SO₂CF₃, $OR^{11}$ and $NR^{11}R^{12}$.
$R^{11}$ and $R^{12}$ are independently selected from the group consisting of H, $C_1$ to $C_6$ alkyl, substituted $C_1$ to $C_6$ alkyl, aryl, substituted aryl, heteroaryl, substituted heteroaryl, acyl, substituted acyl, aroyl, substituted aroyl, and sulfonyl;
or a pharmaceutically acceptable salt thereof.

2. The compound according to claim 1, wherein R₅ is the benzene ring of the formula:

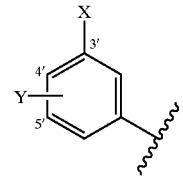

X is selected from the group consisting of halogen, CN, CONH₂, CSNH₂, CONHalkyl, CSNHalkyl, CON(alkyl)₂, CSN(alkyl)₂, $C_1$ to $C_3$ alkoxy, $C_1$ to $C_3$ alkyl, NO₂, $C_1$ to $C_3$ perfluoroalkyl, 5 membered heterocyclic ring consisting of 1 to 3 heteroatoms, and $C_1$ to $C_3$ thioalkoxy;
Y is on the 4' or 5' position and is selected from the group consisting of H, halogen, CN, NO₂, $C_1$ to $C_3$ alkoxy, $C_1$ to $C_4$ alkyl, and $C_1$ to $C_3$ thioalkyl.

3. The compound according to claim 1, wherein R₅ is the five membered ring having the structure shown below

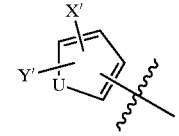

wherein:
U is O, S, or NR₆;
X' is selected from the group consisting of halogen, CN, NO₂, CONH₂, CSNH₂, CONHalkyl, CSNHalkyl, CON(alkyl)₂, CSN(alkyl)₂, $C_1$ to $C_3$ alkyl, and $C_1$ to $C_3$ alkoxy;

Y' is selected from the group consisting of H, F and $C_1$ to $C_4$ alkyl.

4. The compound according to claim 1, wherein $R_5$ is the six membered ring having the structure shown

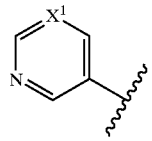

wherein
$X^1$ is N or $CX^2$;
$X^2$ is halogen, CN, $CONH_2$, $CSNH_2$, CONHalkyl, CSNHalkyl, $CON(alkyl)_2$, $CSN(alkyl)_2$, or $NO_2$;
$R_7$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, and $SO_2CF_3$.

5. The compound according to claim 1, wherein $R_5$ is a thiophene or furan ring.

6. A pharmaceutical composition comprising a compound according to claim 1, or a pharmaceutically acceptable salt thereof, and a pharmaceutically acceptable carrier or excipient.

7. A method of inducing contraception in a mammal, the method comprising administering to a mammal in need thereof a pharmaceutically effective amount of a compound of claim 1, or a pharmaceutically acceptable salt thereof.

8. A method of treatment of dysfunctional uterine bleeding in a mammal, the method comprising administering to a mammal in need thereof a pharmaceutically effective amount of a compound of claim 1, or a pharmaceutically acceptable salt thereof.

9. A method of treatment of carcinomas and adenocarcinomas of the endometrium, ovary, breast, colon, or prostate in a mammal, the method comprising administering to a mammal in need thereof a pharmaceutically effective amount of a compound of claim 1, or a pharmaceutically acceptable salt thereof.

10. A method of treatment of carcinomas and adenocarcinomas of uterine leiomyomata, endometriosis or polycystic ovary syndrome in a mammal, the method comprising administering to a mammal in need thereof a pharmaceutically effective amount of a compound of claim 1, or a pharmaceutically acceptable salt thereof.

11. A method of hormone replacement therapy, the method comprising administering to a mammal in need thereof a pharmaceutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 6,583,145 B1
APPLICATION NO. : 10/253380
DATED : June 24, 2003
INVENTOR(S) : Fensome et al.

It is certified that error appears in the above-identified patent and that said Letters Patent is hereby corrected as shown below:

(1) Col. 4, line 64, insert --R = various-- under the drawing;

(2) Col. 7, line 29, delete "C1" and insert -- $C_1$ --;

(3) Col. 10, line 12, delete "CONalky$_2$" and insert -- CONalkyl$_2$ --;

(4) Col. 15, line 18, delete "$C_{02}$alkyl" and insert -- $CO_2$alkyl --;

(5) Col. 17, line 40, delete "alkylamnino" and insert -- alkylamino --;

(6) Col. 17, line 62, delete "multicychic" and insert -- multicyclic --;

(7) Col. 18, line 36, delete "atom" and insert -- atom. --;

(8) Col. 19, line 56, delete "though" and insert -- through --;

(9) Col. 23, line 25, delete "hexamethyldisdazide" and insert -- hexamethyldisilazide --;

(10) Col. 27, line 5, delete "hydrobrornide" and insert -- hydrobromide --;

(11) Col. 29, line 56, delete "medium" and insert -- medium. --;

(12) Col. 32, line 62, delete "Trimethylsilyl" and insert -- Trimethylstannyl --;

(13) Col. 33, line 39, delete "J=6,4" and insert -- J = 6.4 --;

(14) Col. 36, line 6, delete "streptomycin" and insert -- streptomycin --;

(15) Col. 37, line 35, delete "streptomyrcin" and insert -- streptomycin --;

(16) Col. 37, line 44, delete "medium" and insert -- medium. --;

(17) Col. 38, line 59, delete "U/mil" and insert -- U/ml --;

(18) Col. 43, line 54, delete "8.3" and insert -- 8.33 --;

(19) Col. 43, line 59, delete
"[cyclohexane-1,3'-[3H]indol]-5-yl)-1H-pyrrole-1-" and insert
-- [cyclohexane-1,3'-[3H]indol]-5'-yl)-1H-pyrrole-1- --;

UNITED STATES PATENT AND TRADEMARK OFFICE
CERTIFICATE OF CORRECTION

PATENT NO.       : 6,583,145 B1
APPLICATION NO.  : 10/253380
DATED            : June 24, 2003
INVENTOR(S)      : Fensome et al.

It is certified that error appears in the above-identified patent and that said Letters Patent is hereby corrected as shown below:

(20)  Col. 44, line 8, delete "6.3" and insert -- 6.38 --;

(21)  Col. 49, line 34, insert -- g -- after "0.022";

(22)  Col. 50, line 39, delete "as." and insert -- as --;

(23)  Col. 52, line 37, delete "0:029" and insert -- 0.029 --;

(24)  Col. 53, line 19, delete "1,76" and insert -- 1.76 --;

(25)  Col. 53, line 33, delete "indol-5-yl)-2-furancarbonitrile" and insert -- indol]-5-yl)-2-furancarbonitrile --;

(26)  Col. 56, line 52, delete "(1"H)-one" and insert -- (1'H)-one --;

(27)  Col. 58, line 24, delete "tmp." and insert -- m.p. --;

(28)  Col. 59, line 22, delete "130-1320" and insert -- 130-132° --;

(29)  Col. 60, line 18, delete "N-(Acetyoxy)-5'-(3-chlorophenyl)spiro" and insert -- N-(Acetyloxy)-5'-(3-chlorophenyl)spiro --;

(30)  Col. 60, line 43, delete "(140 H)-thione" and insert -- (1'H)-thione --;

(31)  Col. 62, line 14, delete "(3H, d)" and insert -- (1H, d) --;

(32)  Col. 62, line 15, delete "(1H, s )" and insert -- (1H, m) --;

(33)  Col. 64, line 7, delete "(hydroxtimino)-5'-yl)-4-methyl-2-" and insert -- (hydroxyimino)-5'-yl)-4-methyl-2- --;

(34)  Col. 64, line 24, delete "5-Bromospiro{cyclohexane-1,3'-[3H]indol}-2'(1')-one" and insert -- 5-Bromospiro{cyclohexane-1,3'-[3H]indol}-(1'H)-one --;

(35)  Col. 65, line 17, delete "4-(Trimethylsilyl)-2-thiophenecarbonitrile" and insert -- 4-(Trimethylstannyl)-2-thiophenecarbonitrile --;

(36)  Col. 68, line 59, delete "(hydroxtimino)-5'-yl)-4-methyl-2-" and insert -- (hydroxyimino)-5'-yl)-4-methyl-2- --;

UNITED STATES PATENT AND TRADEMARK OFFICE
CERTIFICATE OF CORRECTION

| | | |
|---|---|---|
| PATENT NO. | : 6,583,145 B1 | |
| APPLICATION NO. | : 10/253380 | |
| DATED | : June 24, 2003 | |
| INVENTOR(S) | : Fensome et al. | |

It is certified that error appears in the above-identified patent and that said Letters Patent is hereby corrected as shown below:

(37)  Col. 69, line 30, delete "237" and insert -- .237 --; and

(38)  Claim 1, col. 71, line 30, delete "Hi" and insert -- H, --.

Signed and Sealed this

Thirtieth Day of January, 2007

JON W. DUDAS
*Director of the United States Patent and Trademark Office*